US011607502B2

(12) United States Patent
Waller et al.

(10) Patent No.: US 11,607,502 B2
(45) Date of Patent: Mar. 21, 2023

(54) COMPACT INJECTOR SYSTEMS AND METHODS

(71) Applicant: LynJohnston, LLC, Kalispell, MT (US)

(72) Inventors: Linda J. Waller, Kalispell, MT (US); Paul C. Henninge, Burlington, VT (US)

(73) Assignee: LYNJOHNSTON, LLC, Kalispell, MT (US)

( * ) Notice: Subject to any disclaimer, the term of this patent is extended or adjusted under 35 U.S.C. 154(b) by 0 days.

(21) Appl. No.: 16/961,636

(22) PCT Filed: Jan. 10, 2019

(86) PCT No.: PCT/US2019/013017
§ 371 (c)(1),
(2) Date: Jul. 10, 2020

(87) PCT Pub. No.: WO2019/140067
PCT Pub. Date: Jul. 18, 2019

(65) Prior Publication Data
US 2020/0338276 A1    Oct. 29, 2020

Related U.S. Application Data

(60) Provisional application No. 62/621,506, filed on Jan. 24, 2018, provisional application No. 62/615,924, filed on Jan. 10, 2018.

(51) Int. Cl.
*A61M 5/32*            (2006.01)
*A61M 5/31*            (2006.01)
(Continued)

(52) U.S. Cl.
CPC ........ *A61M 5/3234* (2013.01); *A61M 5/3148* (2013.01); *A61M 5/31513* (2013.01);
(Continued)

(58) Field of Classification Search
CPC .............. A61M 5/3234; A61M 5/3148; A61M 5/31513; A61M 5/3202; A61M 5/3213;
(Continued)

(56) References Cited

U.S. PATENT DOCUMENTS

| 1,436,707 | A | 11/1922 | Gaschke |
| 2,833,280 | A | 5/1958 | Hein, Jr. |

(Continued)

FOREIGN PATENT DOCUMENTS

| CN | 101862490 A | 10/2010 |
| WO | 2009017277 A1 | 2/2009 |

(Continued)

OTHER PUBLICATIONS

International Search Report and Written Opinion received in PCT/US2019/013017 dated May 16, 2019.

(Continued)

*Primary Examiner* — Theodore J Stigell
*Assistant Examiner* — Rachel T. Smith
(74) *Attorney, Agent, or Firm* — Dorsey & Whitney LLP

(57) ABSTRACT

Devices and methods for a compact injector are provided with a compact configuration for ease of carrying or storage, and an activated configuration ready for injection. In the compact configuration, a plunger and a needle are both retracted into the injector housing, and upon actuation to the activated configuration, the plunger extends proximally and the needle extends distally, ready for injection. An extendable needle shield is also provided to block visibility of the needle during injection, and to reduce the risk of inadvertent needle stick at other times, including disposal.

50 Claims, 57 Drawing Sheets

(51) Int. Cl.
*A61M 5/315* (2006.01)
*A61M 5/50* (2006.01)

(52) U.S. Cl.
CPC ........ *A61M 5/3202* (2013.01); *A61M 5/3213* (2013.01); *A61M 5/3245* (2013.01); *A61M 5/5086* (2013.01); *A61M 2005/3208* (2013.01); *A61M 2005/3241* (2013.01); *A61M 2005/3247* (2013.01)

(58) Field of Classification Search
CPC .............. A61M 5/3245; A61M 5/5086; A61M 2005/3208; A61M 2005/3241; A61M 2005/3247; A61M 2005/31518; A61M 5/31511; A61M 2005/3261; A61M 5/46; A61M 5/3204
See application file for complete search history.

(56) References Cited

U.S. PATENT DOCUMENTS

| | | |
|---|---|---|
| 3,043,304 A | 7/1962 | Higgins |
| 3,534,734 A | 10/1970 | Budreck |
| 3,605,744 A | 9/1971 | Dwyer |
| 3,783,997 A | 1/1974 | Brown |
| 3,820,652 A | 6/1974 | Thackston |
| 3,841,329 A | 10/1974 | Killinger |
| 3,916,893 A | 11/1975 | De Felice |
| 4,011,868 A | 3/1977 | Friend |
| 4,221,218 A | 9/1980 | Pfleger |
| 4,493,704 A | 1/1985 | Beard et al. |
| 4,581,023 A | 4/1986 | Kuntz |
| 4,583,973 A | 4/1986 | Humphrey et al. |
| 4,601,708 A | 7/1986 | Jordan |
| 4,710,171 A | 12/1987 | Rosenberg |
| 4,863,433 A | 9/1989 | Payne et al. |
| 5,048,684 A | 9/1991 | Scott |
| 5,141,496 A | 8/1992 | Dalto et al. |
| 5,873,856 A | 2/1999 | Hjertman et al. |
| 5,876,380 A | 3/1999 | Manganini et al. |
| 6,213,977 B1 | 4/2001 | Hjertman et al. |
| 7,011,649 B2 | 3/2006 | De et al. |
| 7,357,790 B2 * | 4/2008 | Hommann ............ A61M 5/326 604/198 |
| 7,462,169 B2 | 12/2008 | Follman et al. |
| 7,931,618 B2 | 4/2011 | Wyrick |
| 8,337,472 B2 | 12/2012 | Edginton et al. |
| 8,535,278 B2 | 9/2013 | Mudd |
| 8,597,245 B2 | 12/2013 | Jeter et al. |
| 8,636,702 B2 | 1/2014 | Schiller et al. |
| 8,647,303 B2 | 2/2014 | Cowe |
| 8,657,793 B2 | 2/2014 | Pellegrini et al. |
| 8,882,719 B2 | 11/2014 | Manke et al. |
| 9,078,974 B2 | 7/2015 | Manke et al. |
| 9,078,975 B2 | 7/2015 | Manke et al. |
| 9,101,719 B2 | 8/2015 | Vernizeau et al. |
| 9,144,446 B2 | 9/2015 | Bogert et al. |
| 9,220,843 B2 | 12/2015 | Mudd |
| 9,333,146 B2 | 5/2016 | Perot et al. |
| 9,333,288 B2 | 5/2016 | Hilliard et al. |
| 9,339,606 B2 | 5/2016 | Evans et al. |
| 9,440,026 B2 | 9/2016 | Wozencroft |
| D772,409 S | 11/2016 | Buell et al. |
| 9,629,961 B2 | 4/2017 | Manke et al. |
| D787,673 S | 5/2017 | Buell et al. |
| 9,681,889 B1 | 6/2017 | Greenhalgh et al. |
| 9,724,660 B2 | 8/2017 | Bogert et al. |
| 10,898,658 B2 | 1/2021 | Waller et al. |
| 2005/0240159 A1 | 10/2005 | Kito et al. |
| 2006/0178641 A1 | 8/2006 | Reynolds |
| 2006/0229568 A1 | 10/2006 | Koopman |
| 2007/0060885 A1 | 3/2007 | Wu |
| 2008/0221529 A1 | 9/2008 | Kiehne |
| 2009/0318880 A1 | 12/2009 | Janish |
| 2010/0179487 A1 | 7/2010 | Woehr |
| 2010/0191184 A1 | 7/2010 | Choi |
| 2010/0280410 A1 | 11/2010 | Moos et al. |
| 2012/0226233 A1 | 9/2012 | Schraga |
| 2012/0277685 A1 | 11/2012 | Limaye |
| 2013/0082057 A1* | 4/2013 | Schiff ................ A61M 5/31511 604/218 |
| 2013/0085457 A1 | 4/2013 | Schiff et al. |
| 2015/0088067 A1 | 3/2015 | Limaye et al. |
| 2017/0182254 A1 | 6/2017 | Heinsbergen et al. |
| 2017/0368267 A1 | 12/2017 | Woloschuk et al. |
| 2018/0028765 A1 | 2/2018 | Waller et al. |
| 2021/0268197 A1 | 9/2021 | Waller et al. |

FOREIGN PATENT DOCUMENTS

| | | |
|---|---|---|
| WO | 2010033782 A2 | 3/2010 |
| WO | 2010033782 A3 | 6/2010 |
| WO | 2015117131 A1 | 8/2015 |
| WO | 2017066886 A1 | 4/2017 |

OTHER PUBLICATIONS

Invitation to Pay Additional Fees and, Where Applicable, Protest Fee dated Mar. 22, 2019 for PCT Application No. PCT/US2019/013017.

English translation of Office Action received in CN App. No. 201980012788.9 dated Nov. 2, 2021.

Extended European Search Report received in EP App No. 19738322.7 dated Sep. 23, 2021.

* cited by examiner

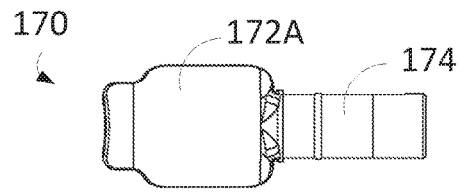
FIG. 3H
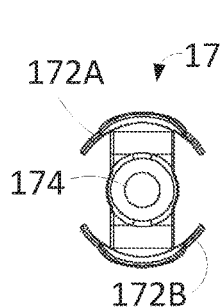
FIG. 3I
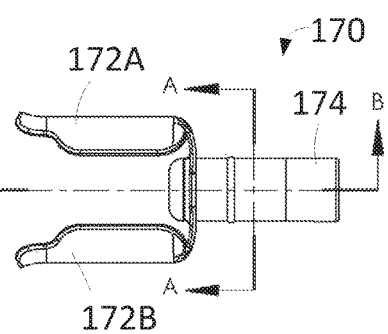
FIG. 3J
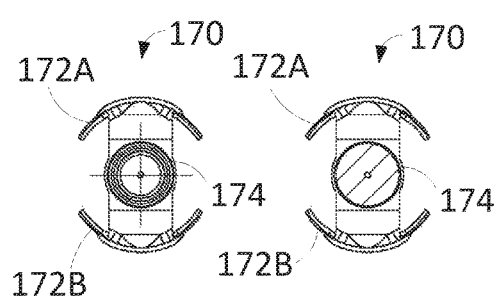
FIG. 3K
FIG. 3L
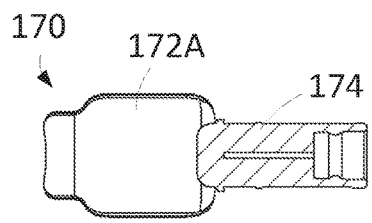
FIG. 3M
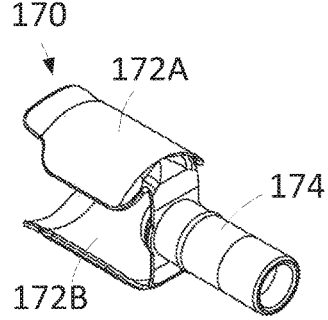
FIG. 3N

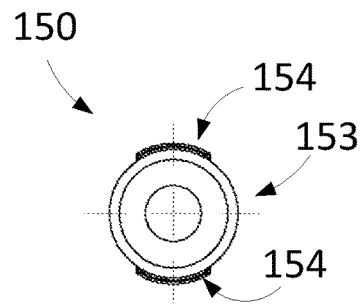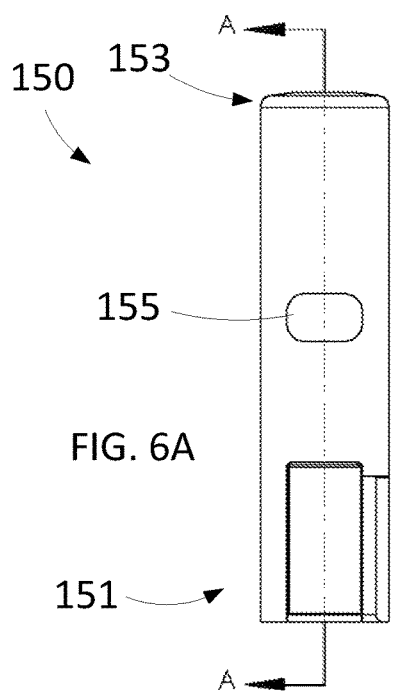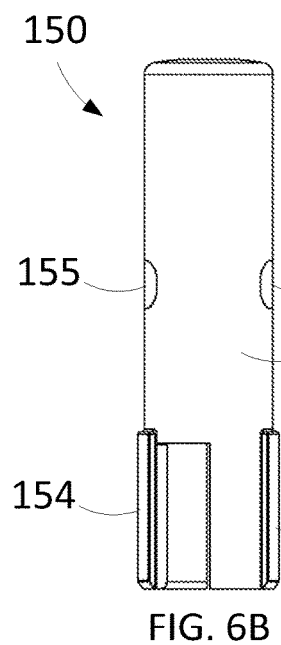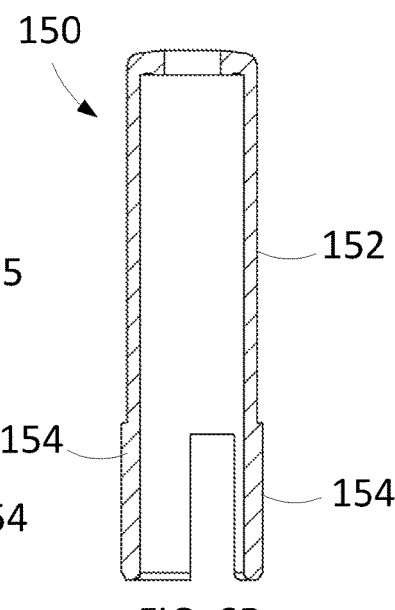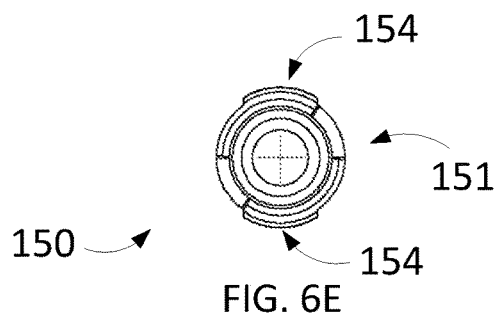

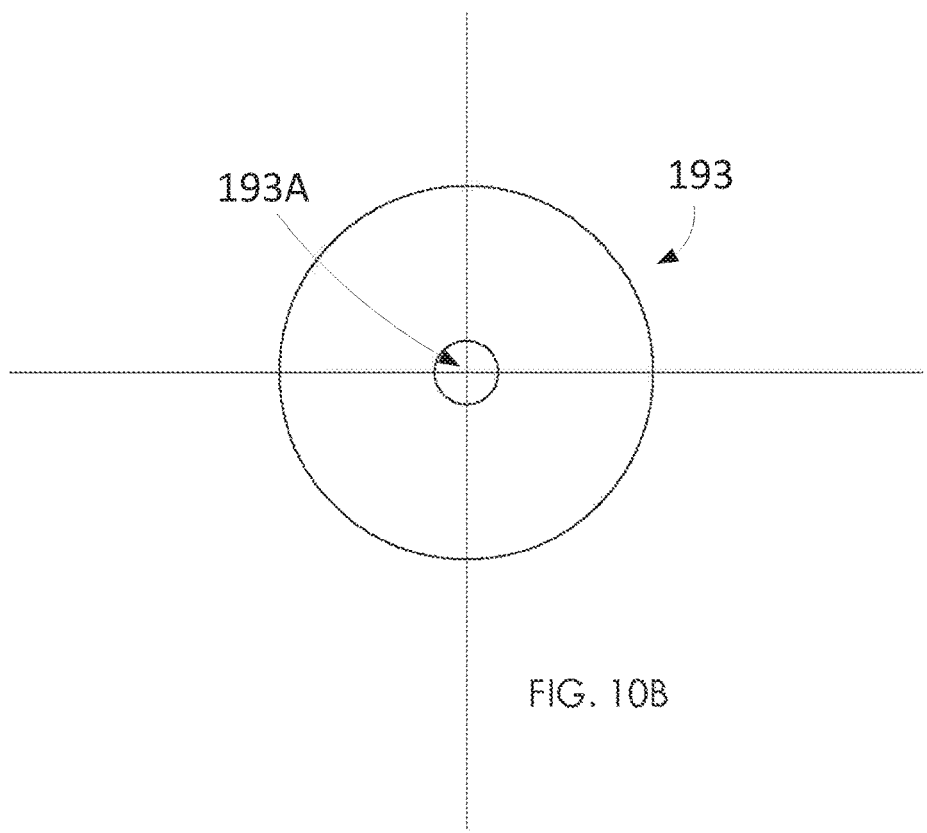
FIG. 10B
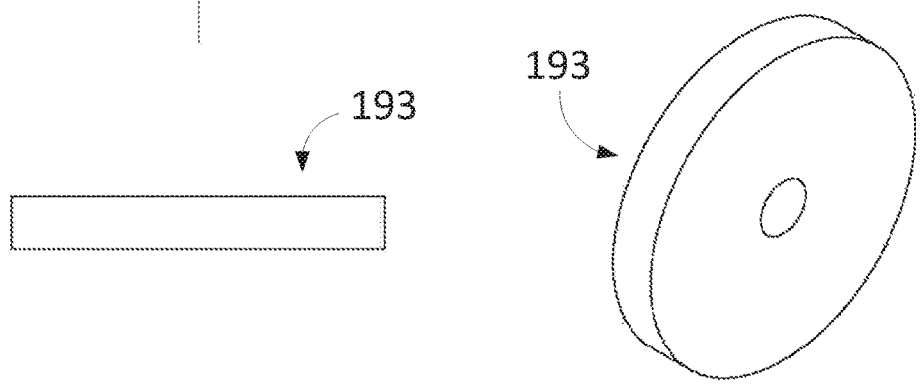
FIG. 10A
FIG. 10C

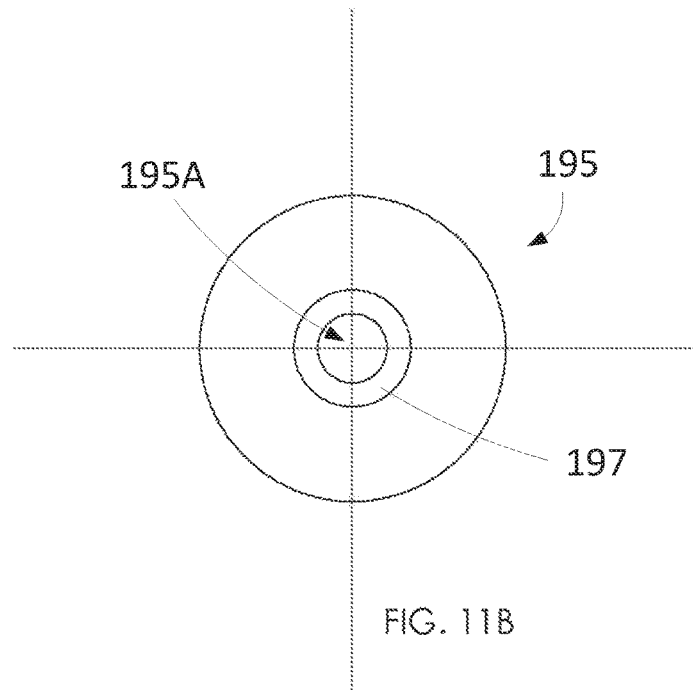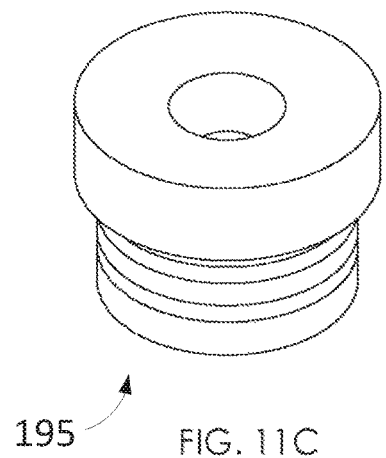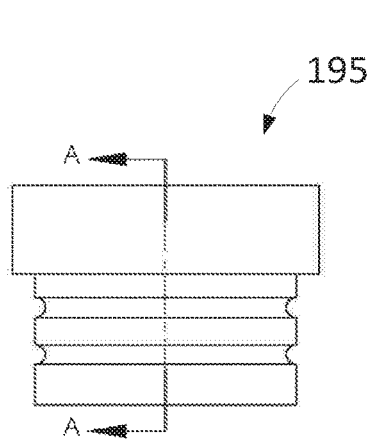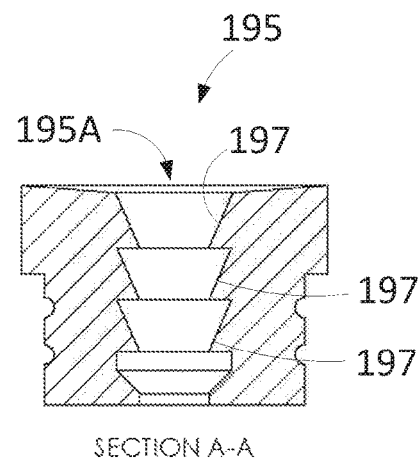
FIG. 11B
FIG. 11C
FIG. 11A
FIG. 11D

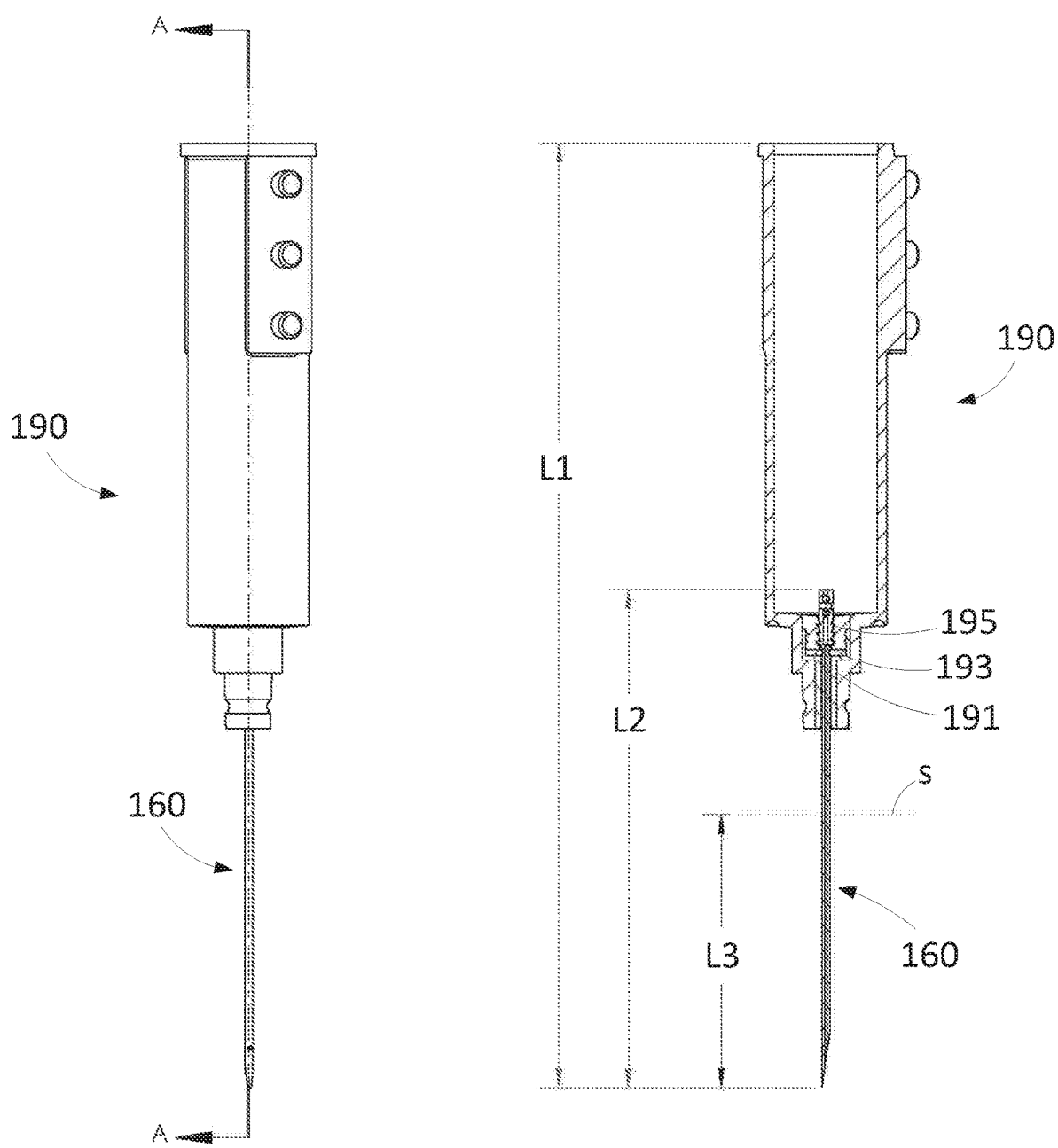

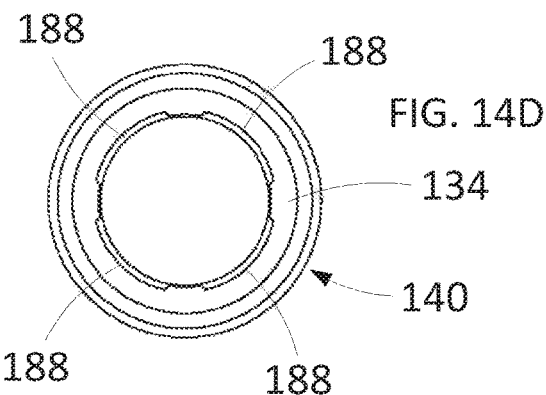
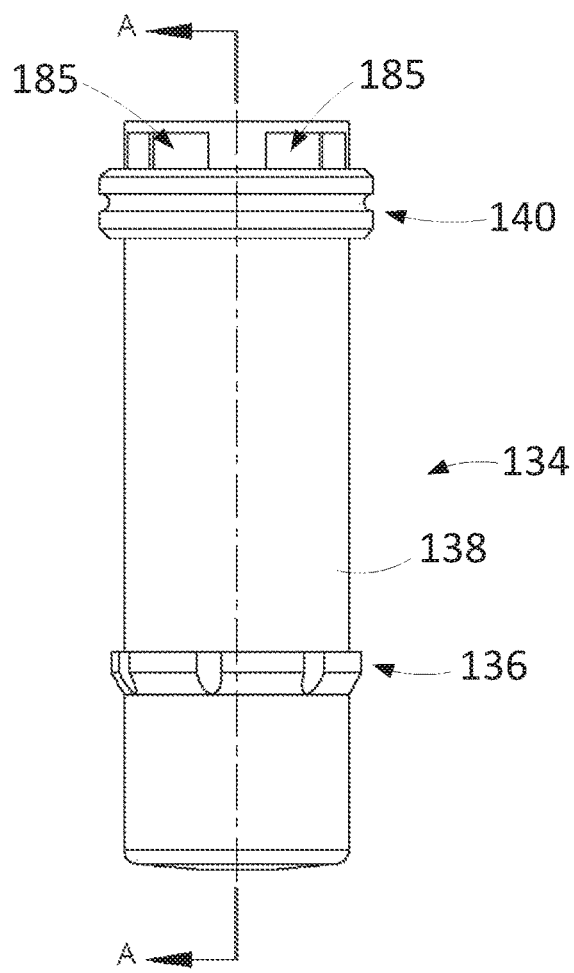
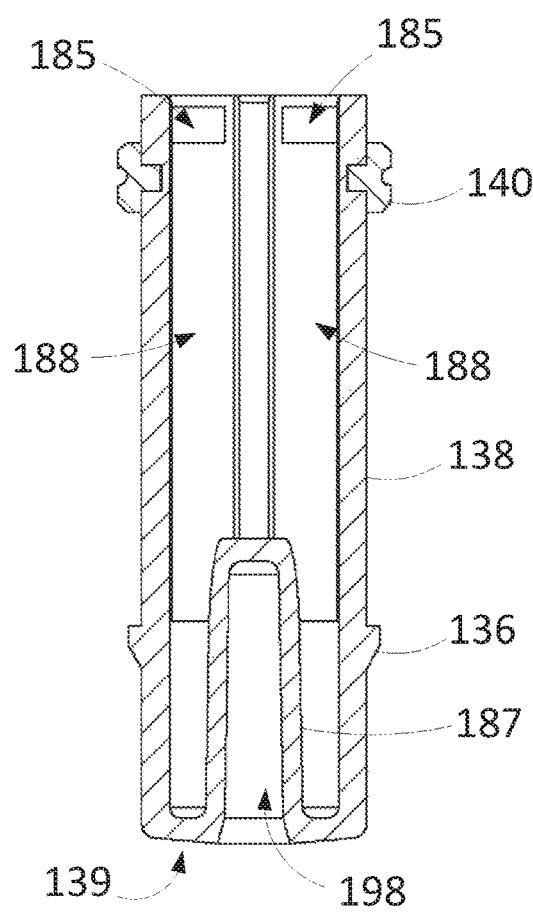
FIG. 14B
FIG. 14C

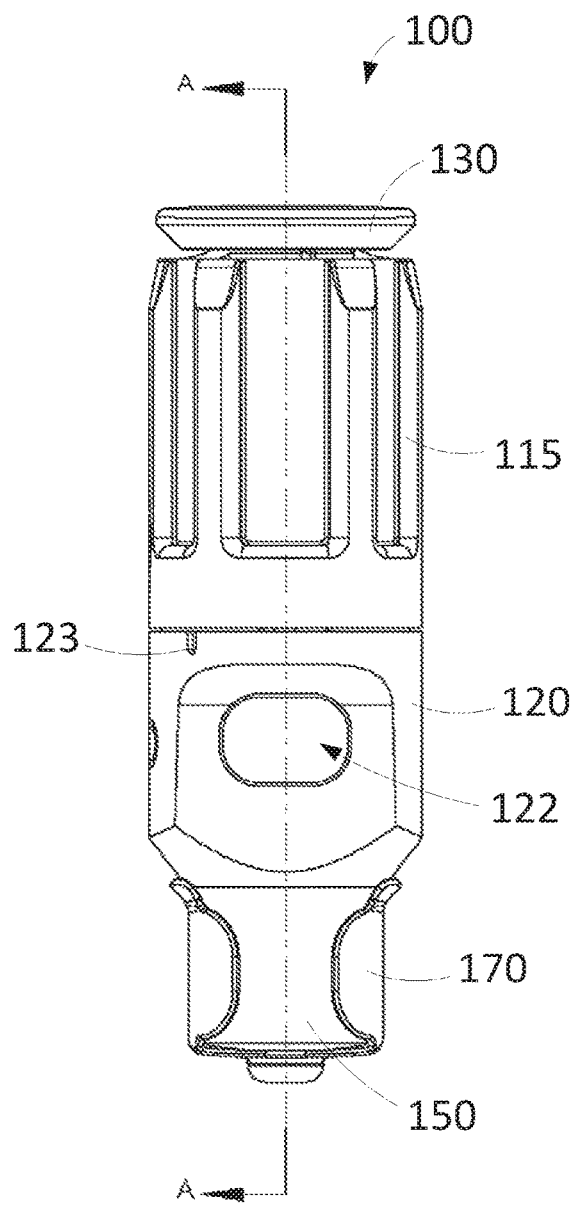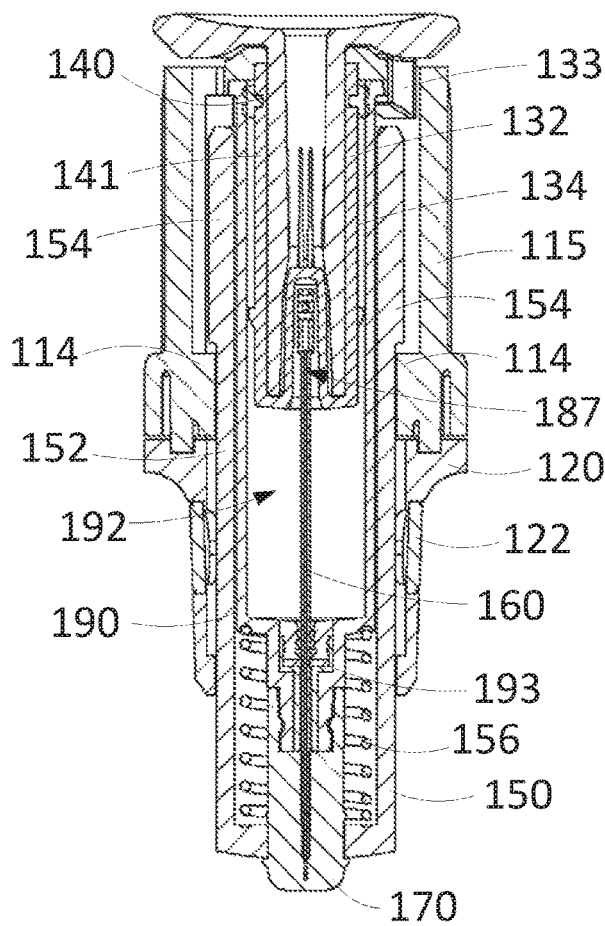
FIG.18A
FIG.18B

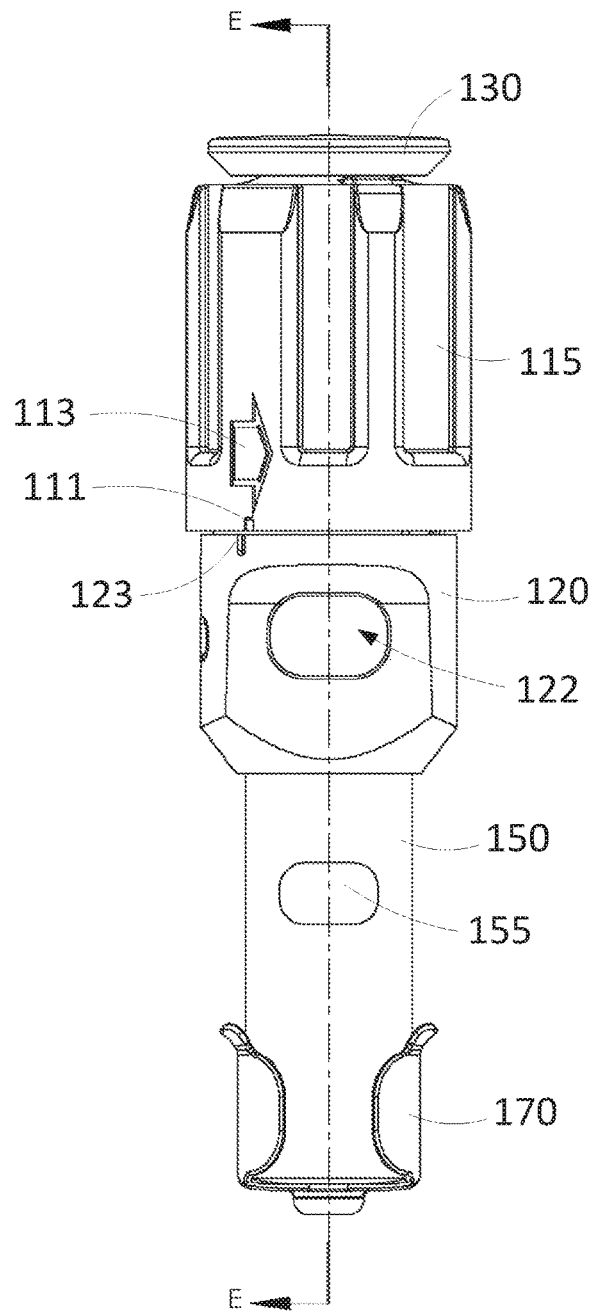
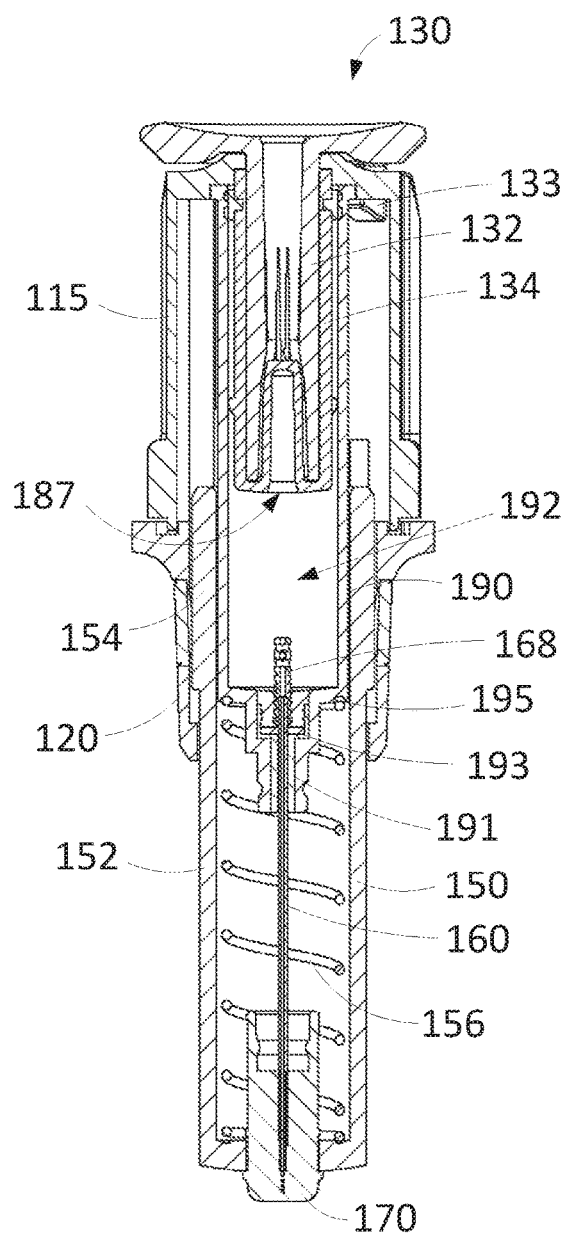
FIG. 19A
FIG. 19B

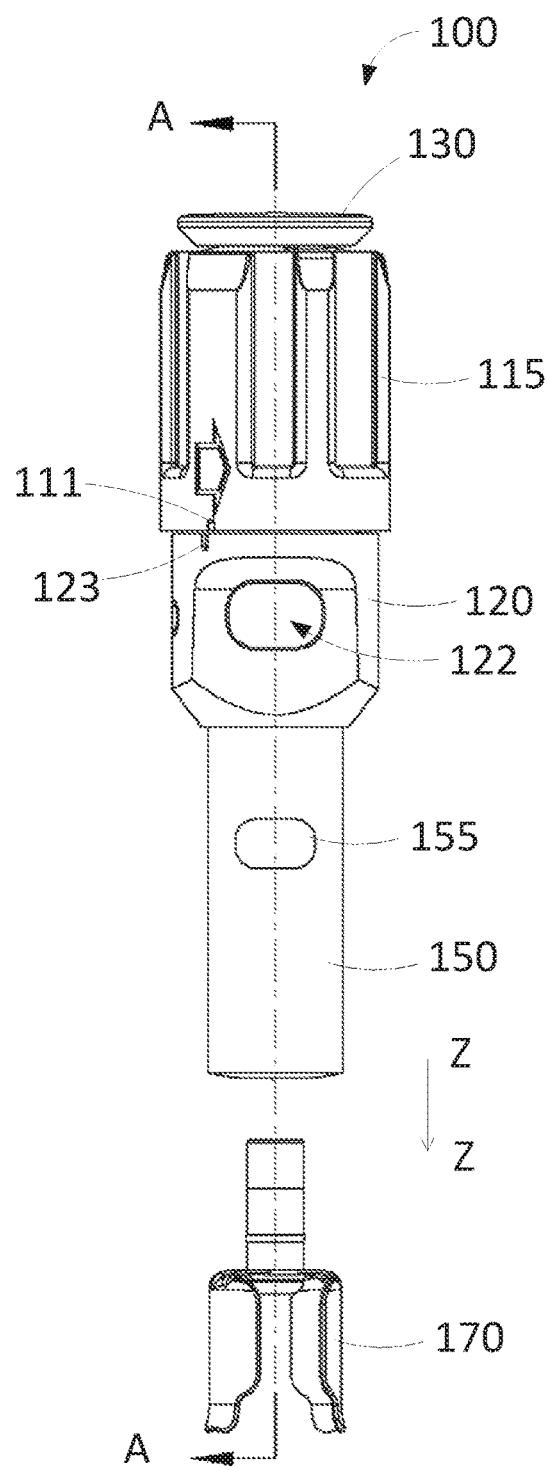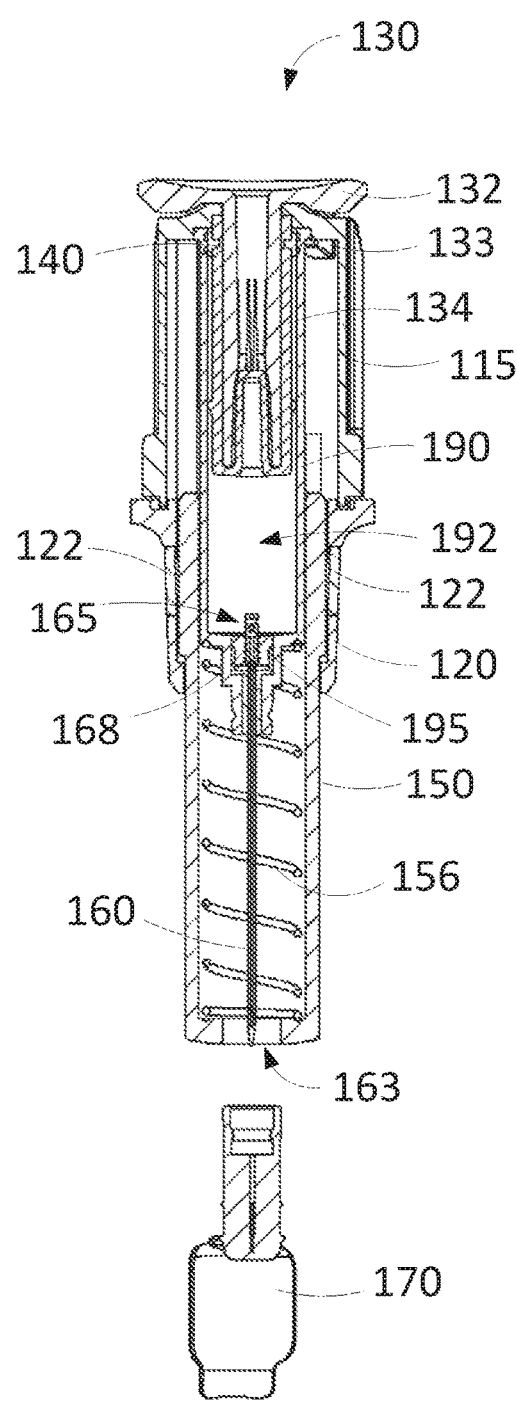
FIG. 20A
Section A-A
FIG. 20B

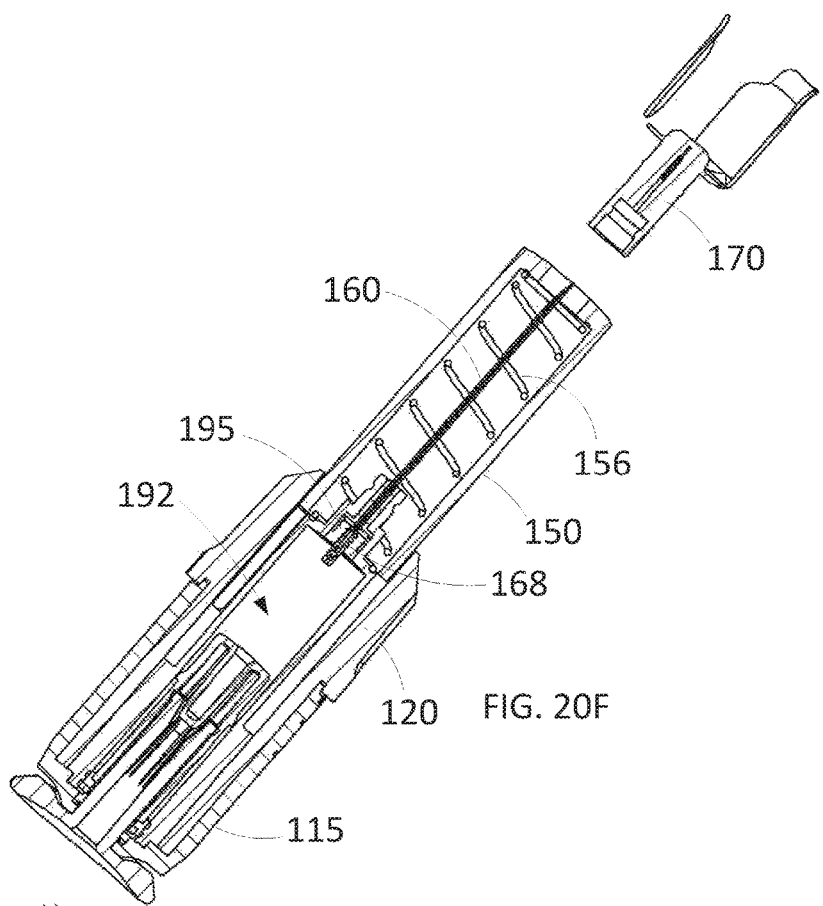
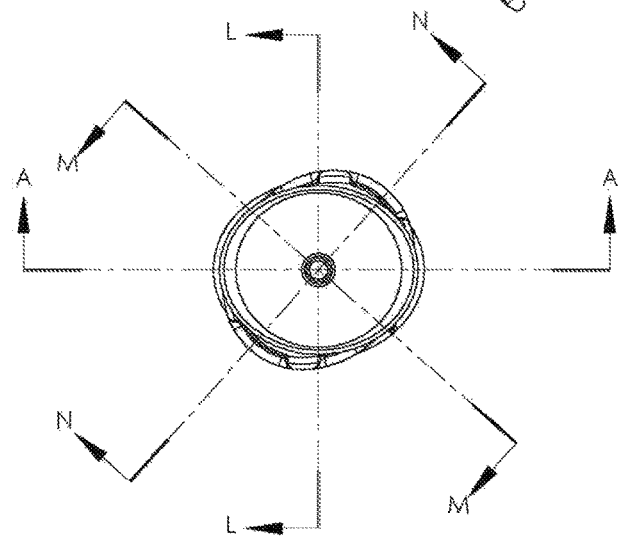
FIG. 20E

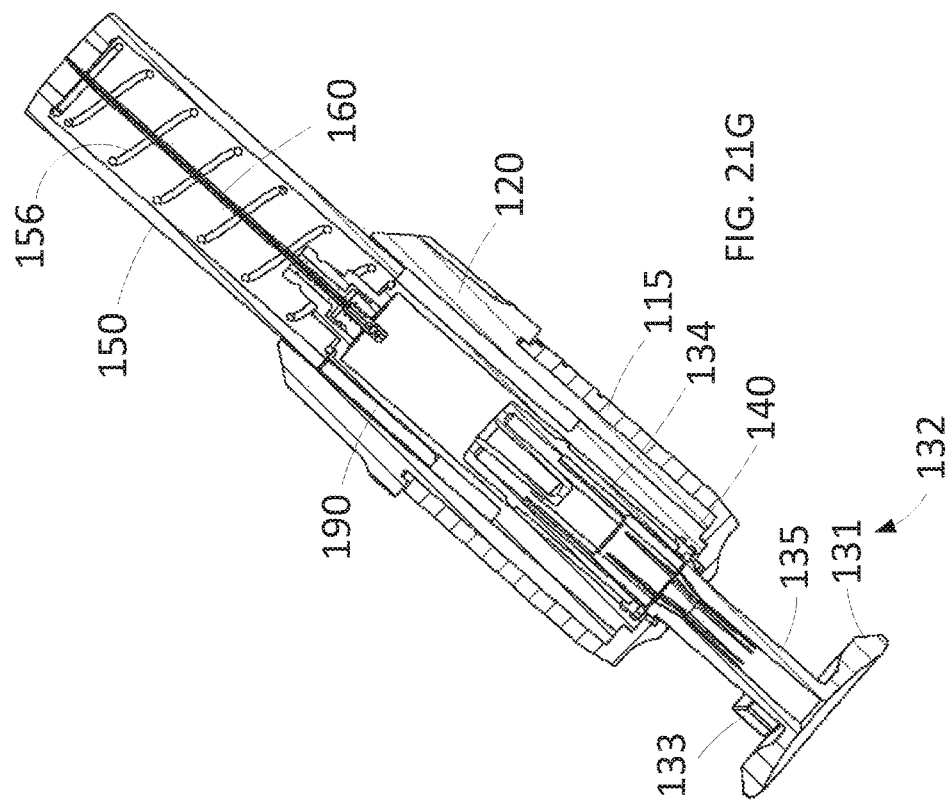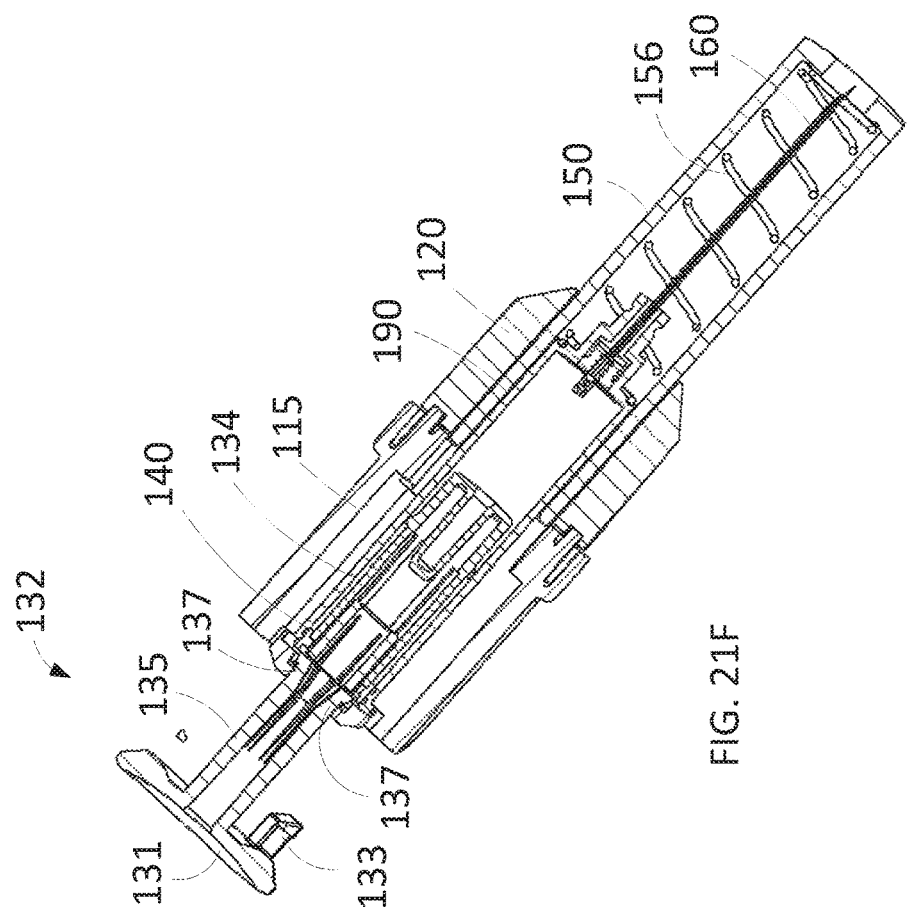

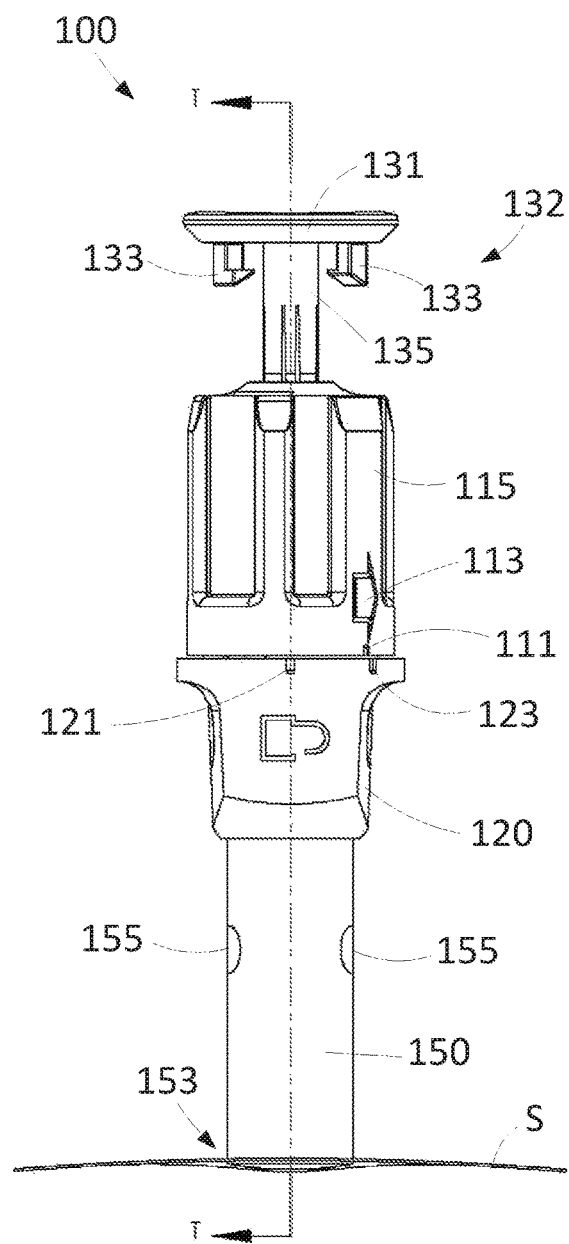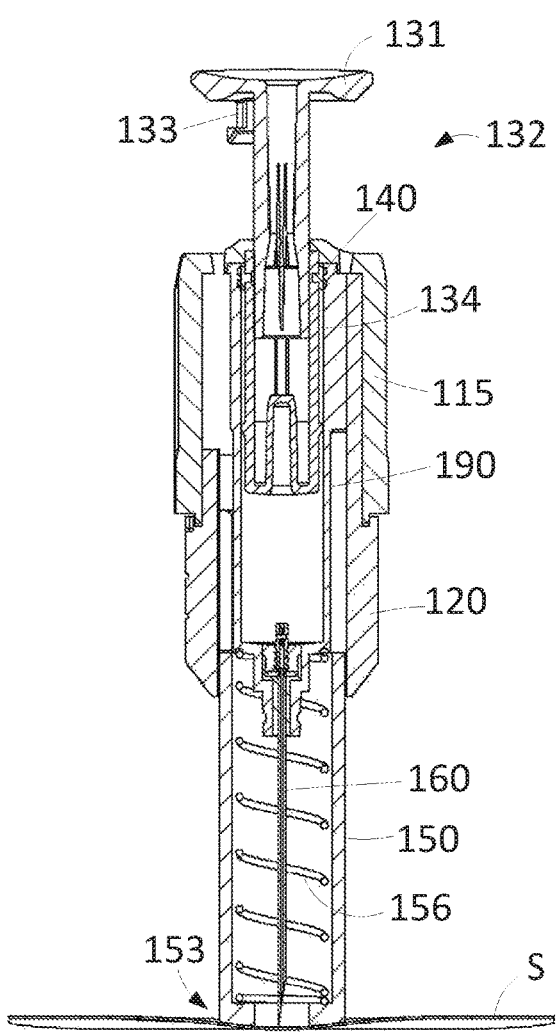
FIG. 22C
FIG. 22D

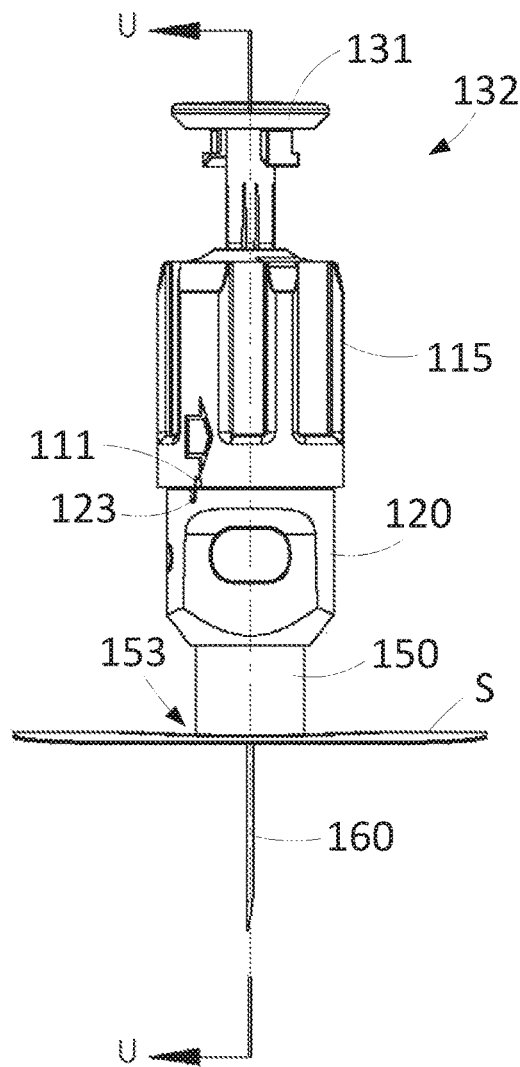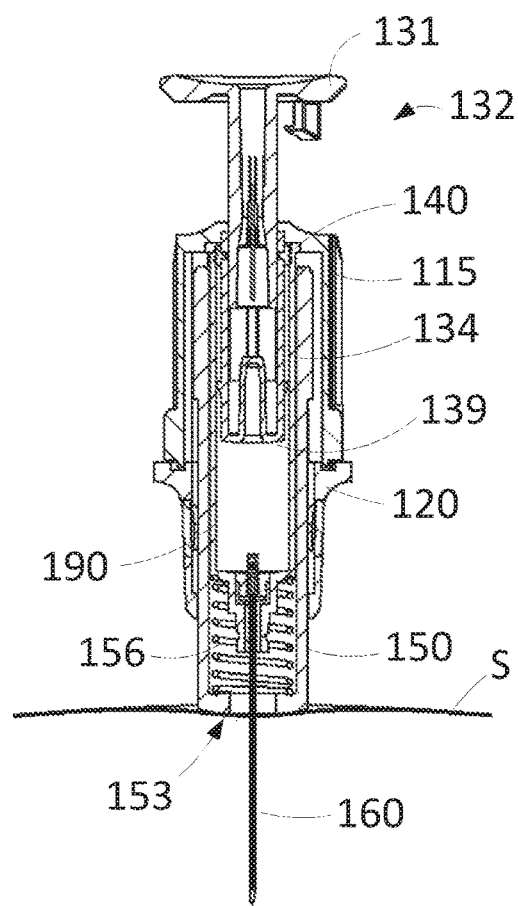
FIG. 23A
FIG. 23B

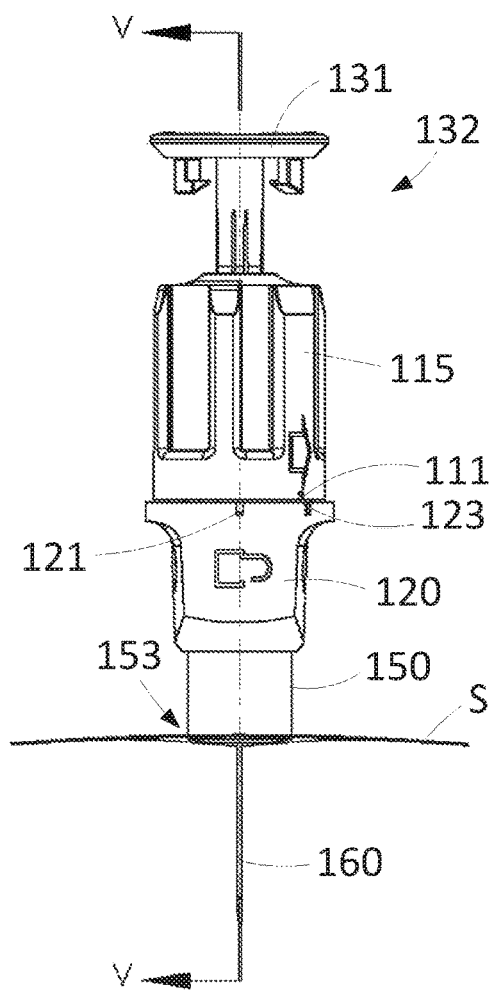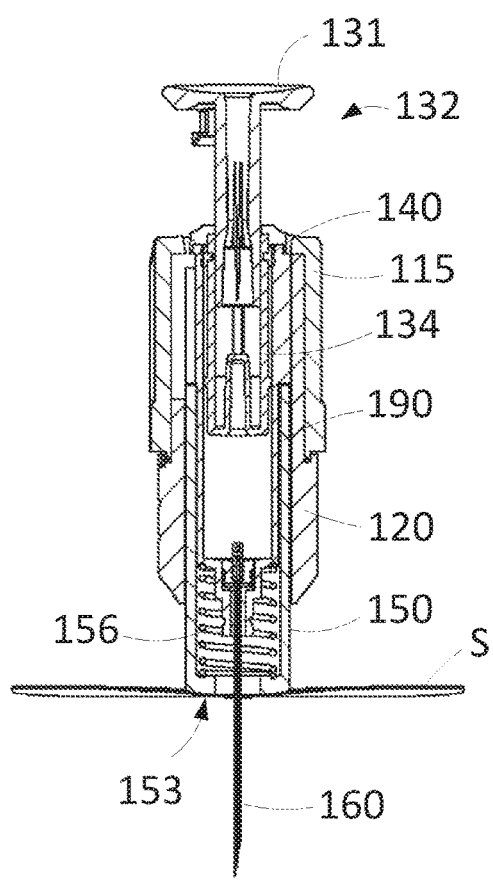
FIG. 23C
FIG. 23D

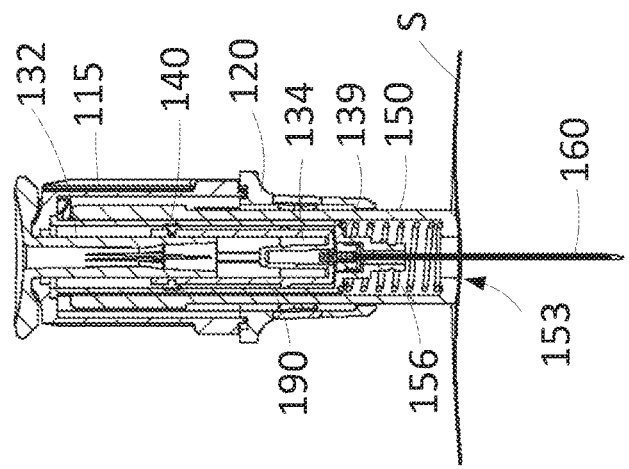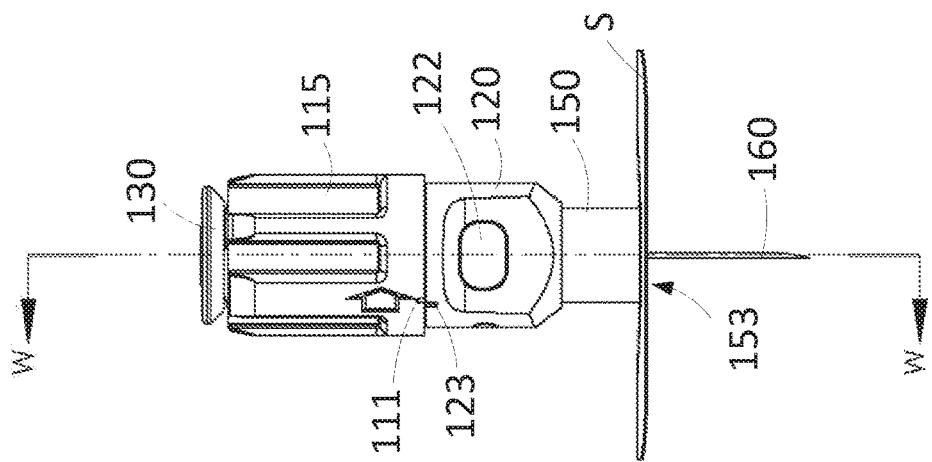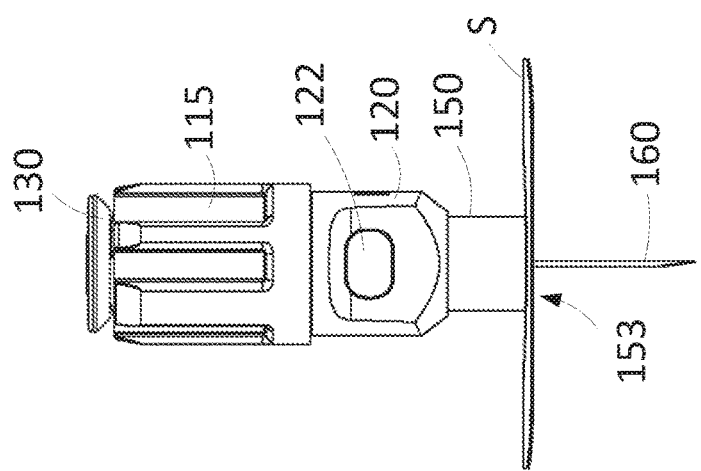

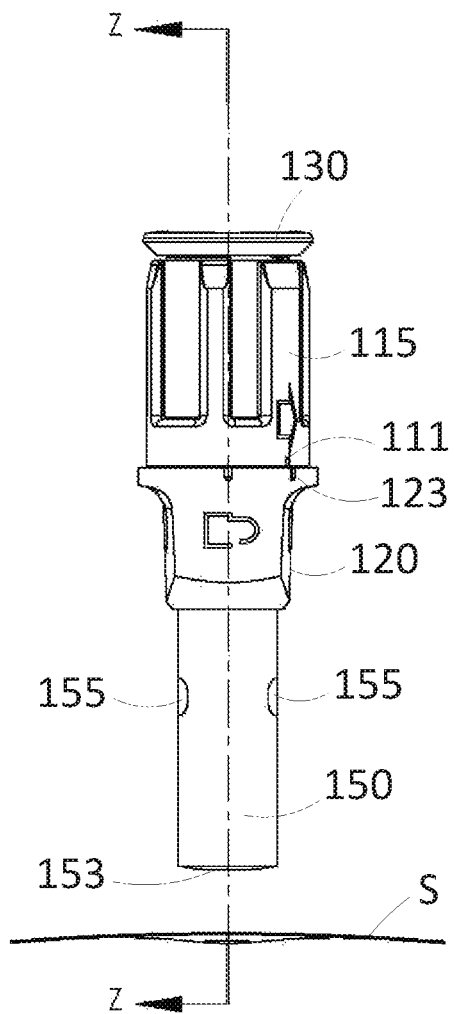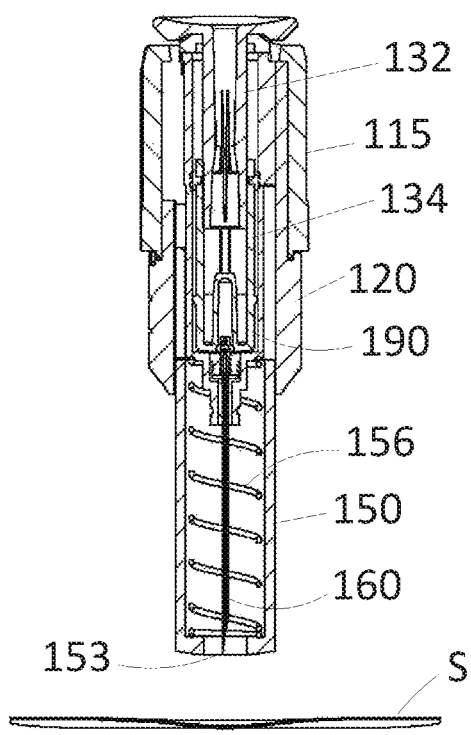
FIG. 25D
FIG. 25E

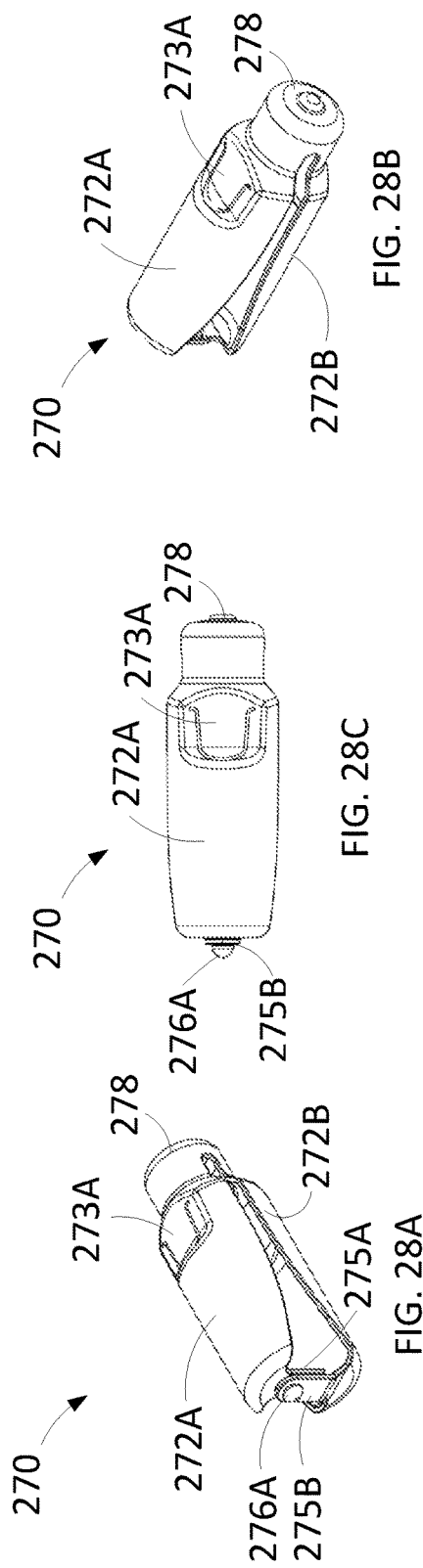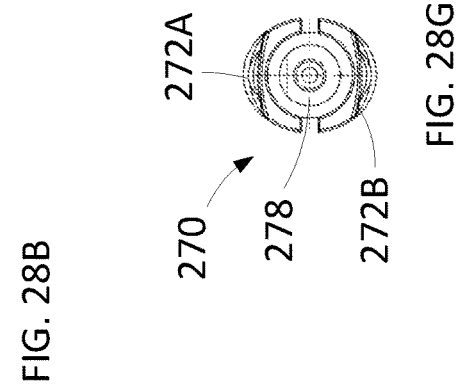

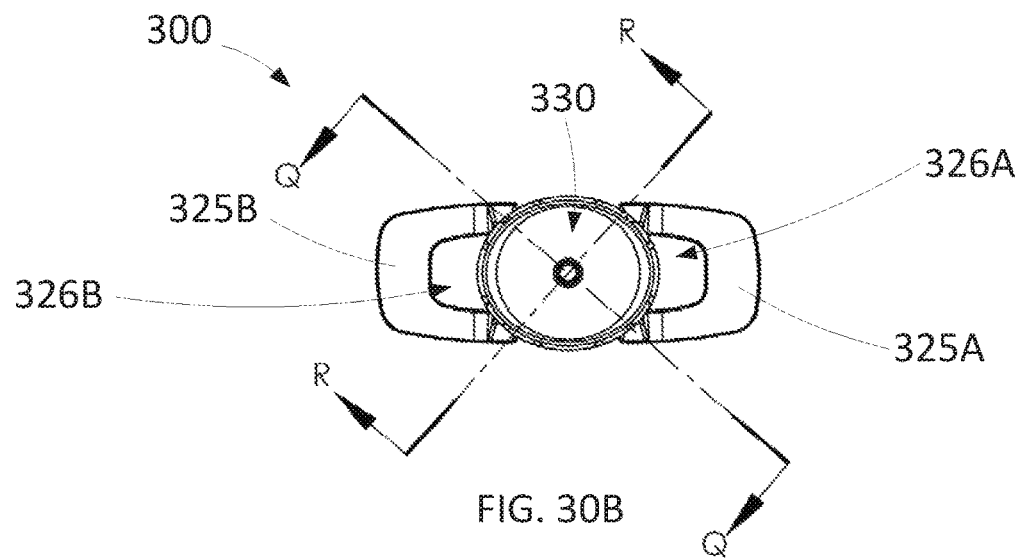
FIG. 30B
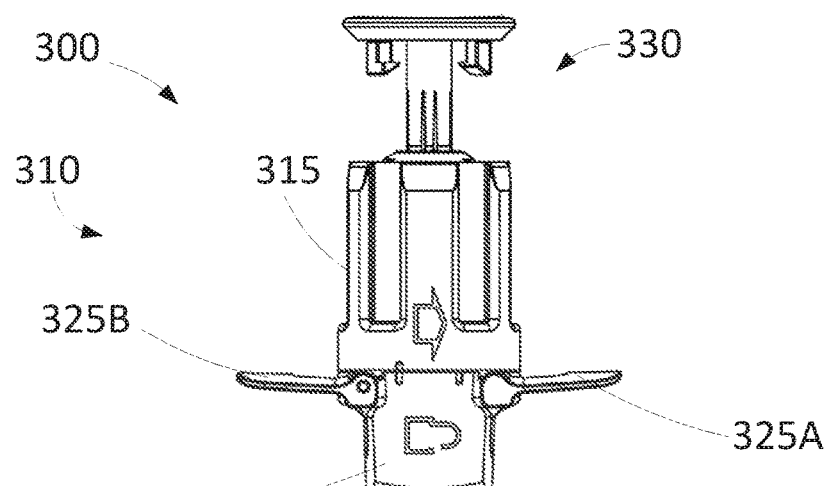
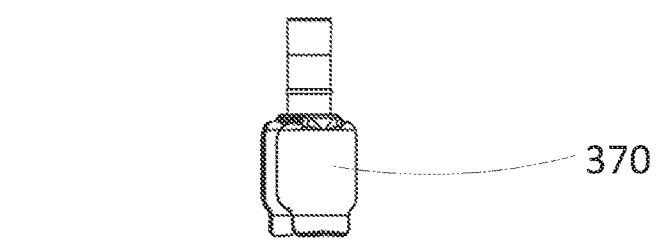
FIG. 30C

COMPACT INJECTOR SYSTEMS AND METHODS

CROSS-REFERENCE TO RELATED APPLICATION(S)

This application is a National Stage Entry of International Application No. PCT/US2019/013017 filed Jan. 10, 2019 which in turn claims priority to U.S. Provisional Application No. 62/615,924 filed Jan. 10, 2018, and U.S. Provisional Application No. 62/621,506 filed Jan. 24, 2018, which are incorporated herein by reference, in their entirety, for any purpose.

BACKGROUND

Embodiments described herein relate to compact injector systems, apparatus, and methods. According to a 2015 survey conducted by the National Institute of Health, 1.6-5.1% of American adults are at risk for anaphylaxis, or roughly 4-12.75 million (Altman, Ashley M., et al. "Anaphylaxis in America: A national physician survey." *The Journal of Allergy and Clinical Immunology*, U.S. National Library of Medicine, March 2015). This does not include the 4 to 6% of American children at risk, a percentage that is on the rise (Sifferlin, Alexandra. "What food allergies are costing families—and the economy" CNN, Cable News Network, 21 Mar. 2014). Allergenic triggers vary, but of the population of Americans at risk for anaphylaxis: 34% are allergic to medications like penicillin and non-steroid anti-inflammatories, 31% are allergic to foods—most commonly peanuts, tree nuts, dairy, soy, eggs, and shellfish, and 20% of those at risk for anaphylaxis are allergic to bees or other insect stings ("Anaphylaxis in America|AAAAI." The American Academy of Allergy, Asthma & Immunology, 15 Oct. 2013). The average person with a life-threatening allergic reaction has ninety seconds to be delivered a life-saving dose of epinephrine before the throat closes and suffocation begins (anaphylaxis). Less commonly, the reaction can be delayed for several hours before rapid onset of symptoms and throat closure. Risk of death increases when patients are not carrying their EPIPEN® or are unable to communicate where the EPIPEN® is before throat closure. From 1999-2009 (latest available data), mortality rates ranged from 186-225 deaths per year ("Facts and Statistics—Food Allergy Research & Education." *Facts and Statistics—Food Allergy Research & Education*. https://www-.foodallergy.org/life-food-allergies/food-allergy-101/facts-and-statistics, 22 Mar. 2017).

Currently, as a first line of treatment for extreme allergic reactions, patients are often prescribed an EPIPEN® two-pack: auto-injection devices to be carried at all times and renewed each year. Although EPIPENS® dominate the market, they are unwieldy. When encased, they are each six inches long and over an inch wide. As a result, it is estimated that two-thirds of EPIPEN® users do not carry them on their person ("Sanofi Announces Auvi-Q™, the First and Only Voice-Guided Epinephrine Auto-Injector, is Now Available in the U.S." Sanofi. 28 Jan. 2013). Further, the EPIPEN® is intended to be exclusively administered in the upper thigh, and the spring inside an EPIPEN® delivers twenty pounds of force to ensure the needle can get through jeans. They are very painful and incite fear of use.

SUMMARY

Systems, apparatus, and methods for compact injection are described herein. Devices and methods may comprise a compact injector with a compact configuration for ease of carrying or storage, and an activated configuration ready for injection. In some examples, the compact configuration may be approximately the size of a lip balm stick, such as a CHAPSTICK®, with a diameter of less than 20 mm and a length of less than 90 mm, 80 mm, or 70 mm, for example, though other diameters and lengths, including larger device, are also contemplated. In the compact configuration, a plunger and a needle are both retracted into the injector housing, and upon actuation to the activated configuration, the plunger extends proximally and the needle extends distally, ready for injection. An extendable needle shield is also provided to block visibility of the needle during injection, and to reduce the risk of inadvertent needle stick at other times, including disposal.

In one exemplary embodiment, an apparatus is provided, comprising a housing assembly, including a first housing portion and a second housing portion, the first housing portion and the second housing portion collectively defining a first interior cavity, an internal cartridge defining a reservoir, the internal cartridge at least partially disposed within the interior cavity, and a plunger assembly which includes a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element, wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position. wherein the first housing portion may further comprise a slot in the proximal end of the first housing portion and a retaining tab extending into the slot and the first plunger portion includes a latch, the latch being disposed within the slot and engaged with the retaining tab when the first housing portion is in the first position, the latch being disengaged from the retaining tab and translatable through the slot when the first housing portion is in the second position. In some further variations, when the first housing portion is in the first position, the second plunger portion may be disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space. The second plunger portion may comprise a guide extending from the sidewall, the guide disposed between the distal end wall of the second plunger portion and the sealing element, the guide contacting an inner surface of the internal cartridge. The first plunger portion may further comprise at least one tab biased to expand axially from a first compressed configuration to a second projecting configuration relative to a central longitudinal axis of the first plunger portion when the first housing portion is in the second position and the first plunger portion has been longitudinally translated proximally relative to the first housing portion, and at least one tab may be configured to extend through a recess of the second plunger portion in the second projecting configuration. The apparatus may further comprise a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position. The needle sheath may include a projecting portion, the projecting portion engaged with a retaining surface of the second housing portion when the first housing portion is in the first position, and the projecting portion disengaged from the retaining surface of the second housing portion when the first housing portion is in the second position. The apparatus may also further comprise a spring having a first end and a second end, the first end of the spring coupled to the internal cartridge and a second end of the internal cartridge coupled to the needle sheath such that the needle sheath is biased toward an expanded position relative to the internal cartridge. The apparatus may also further comprise a needle cover, the needle sheath including a proximal end and a distal end, the needle including a proximal end and a distal end, the proximal end of the needle being disposed within the reservoir, the distal end of the needle and the distal end of the needle sheath coupled to the needle cover. The needle may comprise a hole proximate the distal end of the needle, the needle cover being coupled to the needle via a wire threaded through the hole. The apparatus may further comprise a catch disposed within the internal cartridge, the needle including an engagement portion, the engagement portion configured to engage with the catch upon distal translation of the needle relative to the internal cartridge. A distance from a distalmost portion of the needle cover to a proximalmost portion of the plunger may be less than about 90 mm when the first housing portion is in the first position, the first plunger portion is partially disposed within the second cavity, and the needle cover is coupled to the distal end of the needle sheath. The second plunger portion may comprise a proximal end, the sealing element being disposed proximate the proximal end of the second plunger portion.

In another embodiment, a method is provided, comprising rotating a first housing portion relative to a second housing portion such that a latch of a plunger is disengaged from a retaining tab of the second housing portion, an internal cartridge defining a reservoir at least partially disposed within a first interior cavity collectively defined by the first housing portion and the second housing portion, the plunger including a first plunger portion and a second plunger portion, the second plunger portion defining a second interior cavity, the first plunger portion movably disposed within the second interior cavity, the second plunger portion slidably disposed within the reservoir of the internal cartridge, proximally translating the first plunger portion relative to the second plunger portion and relative to the first housing portion such that at least one tab of the first plunger portion transitions from a first, compressed configuration to a second, projecting configuration, and distally translating the first plunger portion such that the at least one tab distally translates the second plunger portion within the internal cartridge. The rotating of the first housing portion relative to the second housing portion may be configured to cause a needle sheath to rotate from an engaged position to a disengaged position relative to the second housing portion and to distally translate relative to the second housing portion such that a needle cover coupled to a distal end of the needle sheath and coupled to a distal end of a needle disposed within the needle sheath distally translates the needle relative to the internal cartridge. The method may further comprise removing the needle cap such that the needle is further distally translated relative to the internal cartridge.

In still another embodiment, an apparatus is provided, comprising a housing assembly including a first housing portion and a second housing portion, the first housing portion and the second housing portion collectively defining a first interior cavity, an internal cartridge defining a reservoir, the internal cartridge at least partially disposed within the first interior cavity, the internal cartridge including a catch, a plunger assembly slidably disposed within the reservoir of the internal cartridge, a needle sheath including a proximal end and a distal end, the proximal end of the needle sheath disposed within the first interior cavity, a needle including a proximal end and a distal end, the proximal end of the needle disposed within the reservoir, the needle including an engagement portion disposed within the reservoir, and a needle cover coupled to the distal end of the needle sheath and the distal end of the needle, the first housing portion configured to be rotated relative to the second housing portion between a first position and a second position, the needle sheath prevented from being longitudinally translated relative to the second housing portion when the first housing portion is in the first position, the needle sheath longitudinally translatable relative to the second housing portion when the first housing portion is in the second position, the needle cover, the needle, and the needle sheath being arranged such that distal translation of the needle sheath relative to the housing translates the needle distally via the needle cover such that the engagement portion of the needle engages with the catch feature of the internal cartridge. The apparatus may be configured such that removal of the needle cover from the needle and the needle sheath distally translates the engagement portion of the needle relative to the catch feature of the internal cartridge. The apparatus may further comprise a seal, the plunger assembly including a distal end wall and a sidewall, the seal coupled to the sidewall of the plunger assembly proximal of the distal end wall of the plunger assembly, the seal in sealing contact with the internal cartridge such that the seal partial defines the reservoir. The plunger assembly may comprise a guide extending from the sidewall of the plunger assembly to the internal cartridge, the guide disposed on the sidewall of the plunger assembly between the seal and the distal end wall of the plunger assembly.

In another embodiment, a method of preparing an injector is provided, comprising removing an injector cap from an injector housing, pulling a needle out of a medicament cartridge located in the injector housing, twisting the injector housing to unlock an extendible plunger, and extending a needle sheath from the injector housing. The removal of the injector cap and the pulling of the needle may occur simultaneously. The pulling of the needle may be performed using a needle wire through a side hole of the needle, and wherein the needle wire is attached to the injector cap.

In another embodiment, an injection subassembly is provided, comprising a needle guide bushing, comprising a proximal end, a distal end with a needle catch interface, and a lumen therebetween, and a needle slidably located within the needle guide bushing, comprising a proximal end with a bushing catch interface complementary to the needle catch interface, a beveled distal end with a transverse opening, and longitudinal lumen between the proximal end and the distal end. The injection subassembly may further comprise a medicament cartridge, comprising a proximal end, a distal end and an internal cavity therebetween, and wherein the needle guide bushing resides within the internal cavity of the medicament cartridge and the distal end of the needle is located distal to the distal end of the medicament cartridge. The injection subassembly may further comprise a slidable stop within the internal cavity. The slidable seal may comprise a proximal surface accessible from the proximal end of the medicament cartridge, the proximal surface comprising a plunger interlocking interface. The plunger interface may be a helical screw interface. The injection subassembly may further comprise a syringe connector. The syringe connector may comprise a proximal friction interfit interface or a Luer connector. The syringe connector and the needle guide bushing may be integrally formed. The needle guide bushing may reside within the syringe connector. The bushing catch interface of the needle may comprise distally tapered barbs, and the needle catch interface of the needle guide bushing may comprise distally tapered internal ridges complemental to the distally tapered barbs.

In another example, a method of injecting a therapeutic agent is provided, comprising removing an injector cap from an injector housing, pulling a needle out of a medicament cartridge located in the injector housing, twisting the injector housing to unlock an extendible plunger, extending a needle sheath from the injector housing, inserting the needle into an injection site, and depressing the plunger to deliver a therapeutic agent contained in the medicament cartridge. The removal of the injector cap and the pulling of the needle may occur simultaneously. The pulling of the needle may be performed using a needle wire through a side hole of the needle, and wherein the needle wire is attached to the injector cap.

Although certain examples described herein are for intramuscular injection of epinephrine for treatment or prevention of anaphylactic shock, the injectors described herein may also be provided for use with any of a variety of clinical indications, therapeutic agents, and/or injection routes, and is not limited to ambulatory or emergency uses. For example, the injector may also be used for intravenous or subcutaneous injection, or may comprise a Luer lock in place of a needle for connection to a peripheral or central venous line. The injector may be configured with a variety of therapeutic or diagnostic agents, including but not limited to agents for use in radiologic imaging, advanced cardiac life support, psychiatric settings, home antibiotic treatment for a variety of infection disease indications, etc. Examples of particular agents include but are not limited to haloperidol, chlorpromazine, lorazepam, morphine, codeine, adenosine, amiodarone, atropine, dopamine, lidocaine, magnesium, calcium chloride, procainamide, ACE inhibitors (e.g. enalapril), beta blockers (e.g. metoprolol, atenolol, propranolol, esmolol, labetalol, sotalol), DIGIBIND®, digoxin, dobutamine, fibrinolytic agents (e.g. alteplase, anistreplase, reteplase, streptokinase, tPA), flecainide, furosemide, glucagon, heparin, mannitol, naloxone, nitroglycerin, nitroprusside, vasopressin, calcium channel blockers (e.g. verapamil), insulin and insulin analogues, or other diabetes agents, and the like.

BRIEF DESCRIPTION OF THE DRAWINGS

FIGS. 3H-3N are various views of the cover of FIGS. 3A-3G in a second, detached configuration.

FIGS. 6A-6E are various views of a needle sheath of the injector device of FIG. 1A.

FIGS. 10A-10C are a front view, a top view, and a perspective view, respectively, of a guide seal of the injector device of FIG. 1A.

FIGS. 11A-11D are various views of the catch feature of the injector device of FIG. 1A.

FIGS. 13A-13C are various views of the internal cartridge, the needle, the guide bushing, the guide seal, and the catch feature of the injector device of FIG. 1A in an injection configuration in which the needle is engaged with the catch feature.

FIGS. 14A-14D are various views of a second plunger portion of a plunger assembly of the injector device of FIG. 1A.

FIGS. 18A-18G are various views of the injector device of FIG. 1A in a first, locked configuration.

FIGS. 19A-19G are various views of the injector device of FIG. 1A in a second, unlocked configuration.

FIGS. 20A-20G are various views of the injector device of FIG. 1A in a third, uncovered configuration.

FIGS. 21A-21G are various views of the injector device of FIG. 1A in a fourth, extended or "ready" configuration.

FIGS. 22A-22D are various views of the injector device of FIG. 1A disposed on a skin of a user prior to penetration.

FIGS. 23A-23D are various views of the injector device of FIG. 1A in a fifth, penetration configuration.

FIGS. 24A-24E are various views of the injector device of FIG. 1A in a sixth, injection configuration.

FIG. 25A-25E are various views of the injector device of FIG. 1A in a seventh, withdrawn configuration.

FIGS. 28A-28G are various views of an injector device cover, according to an embodiment.

FIGS. 30A-30E are various views of an injector device, according to an embodiment.

DETAILED DESCRIPTION

The injection devices described herein are configured with a compact size so that the user can easily carry it or keep it close by, e.g. in a backpack, belt clip, bracelet or necklace, for example. When activated, the plunger can extend proximally and the needle can extend distally to facilitate injection of the medication. In some embodiments, the length of the device in the compact or storage configuration may be in the range of about 60 mm to about 70 mm, about 50 mm to about 80 mm, or about 62 mm to about 66 mm. The diameter may be in the range of about 18 mm to about 26 mm, about 16 mm to about 31 mm, or about 21 mm to about 25 mm. When the device is activated, the length may increase to be in a range of about 100 mm to about 110 mm, about 90 mm to about 120 mm, or about 103 mm to about 105 mm. Typically, the average diameter or largest axial cross-sectional dimension, will not change, but in other examples, the diameter may also change to a size in the range of about 5 mm to about 18 mm, about 9 mm to about 28 mm, or about 19 mm to about 26 mm. In the extended configuration, the plunger may extend an additional distance from the injector housing of about 0.1 mm to about 8 mm, about 0.1 mm to about 11 mm, or about 0.5 mm to about 7 mm, while the needle may extend an additional distance from the injector housing in the range about 0.5 mm to about 8 mm, about 0.1 mm to about 11 mm, or about 1 mm to about 7 mm.

Figure 1A:
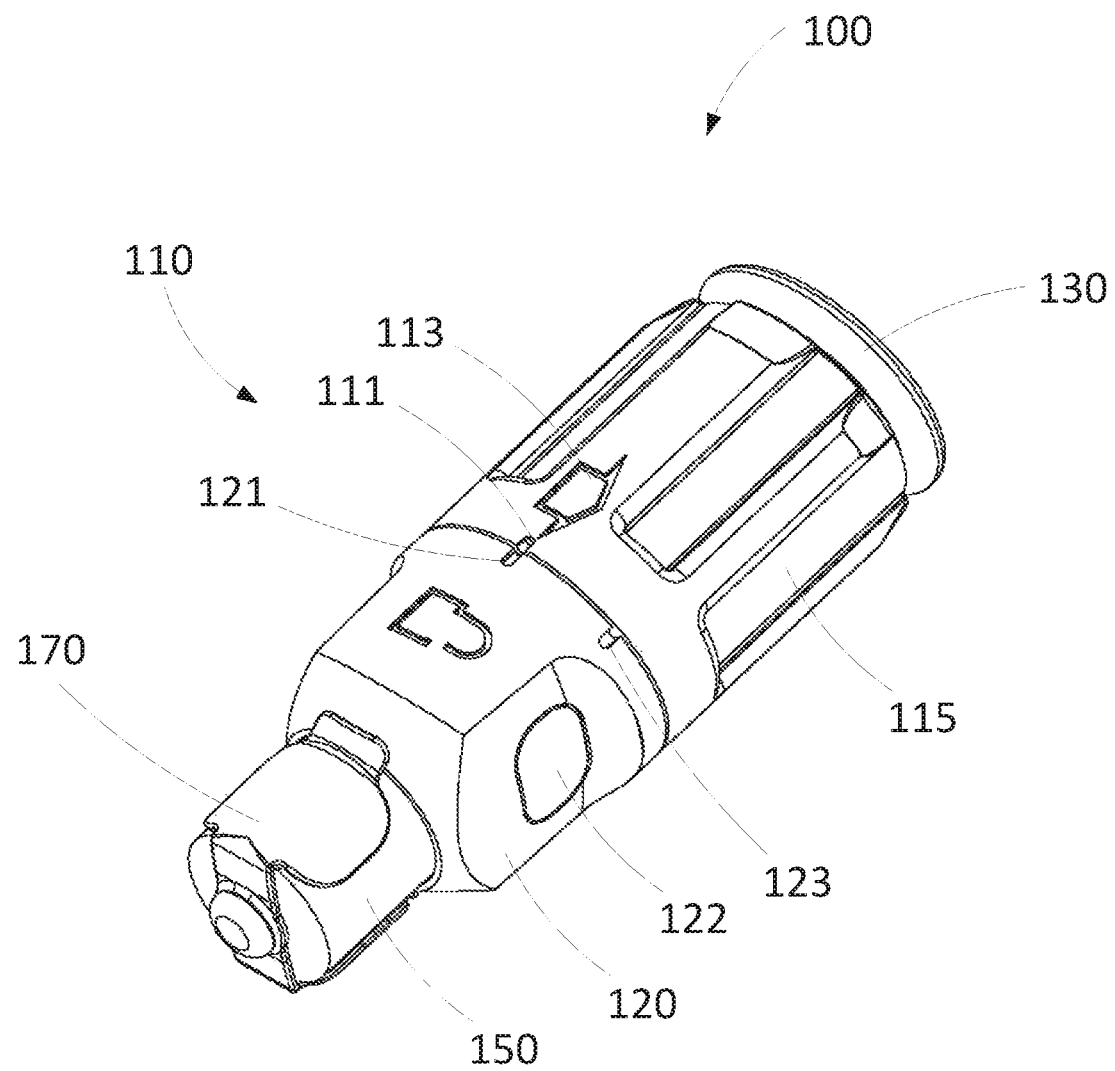
FIGS. 1A-IC are various views of an injector device, according to an embodiment.
Figure 1B:
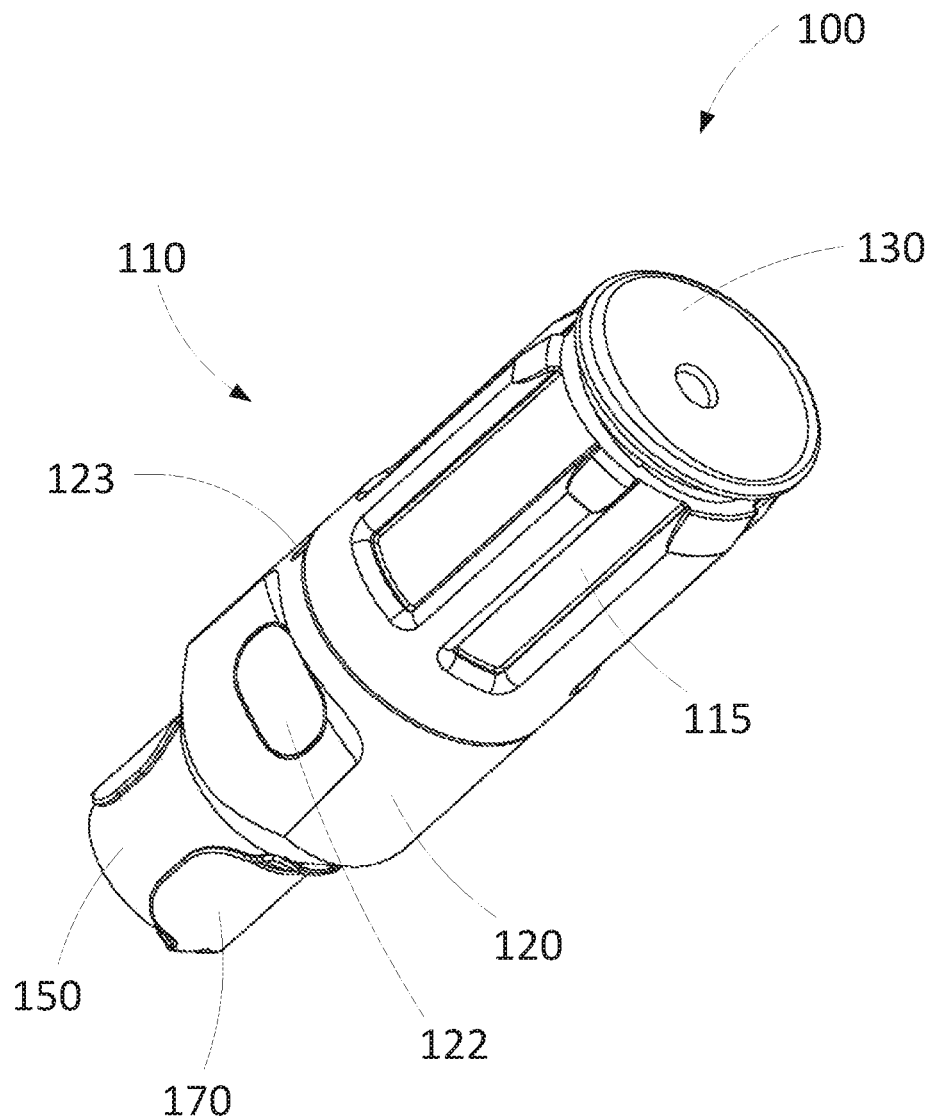
Figure 1C:
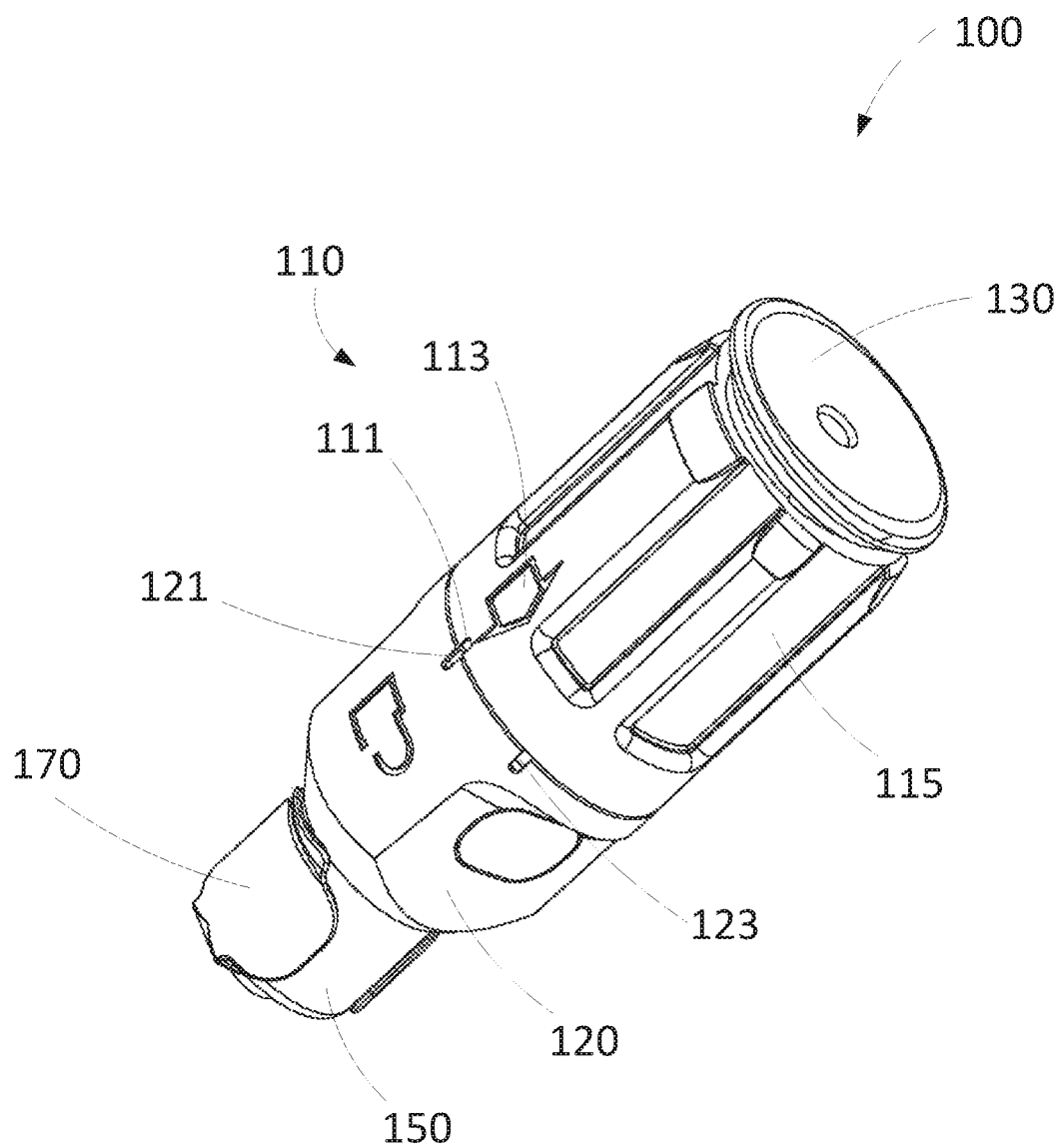

FIGS. 1A-1C are various perspective views of an injector device 100 shown in a locked configuration. As shown in FIGS. 1A-1C, the injector device 100 includes a housing assembly 110, a plunger assembly 130, a needle sheath 150, and a cover 170. The housing assembly 110 includes a first housing portion 115 and a second housing portion 120. The first housing portion 115 is coupled to the second housing portion 120 such that the first housing portion 115 can be rotated relative to the second housing portion 120 to transition the injector device 100 between the locked configuration shown in FIGS. 1A-1C and an unlocked configuration (shown, for example, in FIGS. 19A-19G). As shown in FIGS. 1A-1C, the first housing portion 115 can include ribs disposed on the outer surface of the first housing portion 115 to facilitate gripping of the first housing portion 115 by the user. Although shown as including ribs, the first housing portion 115 can include any suitable shape, features, or materials to facilitate gripping, such as a textured surface.

The first housing portion 115 can include a positional indicator notch 111. The second housing portion 120 can include a locked indicator notch 121 and an unlocked indicator notch 123. When the injector device 100 is in the locked configuration, the positional indicator notch 111 of the first housing portion 115 can be aligned with the locked indicator notch 121 of the second housing portion 120, indicating to a user that the injector device 100 is in the locked configuration. The rotation of the first housing portion 115 relative to the second housing portion 120 can rotate the positional indicator notch 111 between alignment with the locked indicator notch 121 and alignment with the unlocked indicator notch 123. Thus, the user can visually confirm that the injector device 100 is in the locked and/or unlocked configuration. In some embodiments, the transition of the positional indicator notch 111 into alignment with the unlocked indicator notch 123 can also include tactile or auditory feedback, such as a snap sound.

Additionally, the first housing portion 115 can include a directional indicator 113 (e.g., an arrow), indicating the direction the first housing portion 115 can be rotated relative to the second housing portion 120 to transition the injector device 100 between the locked configuration and the unlocked configuration. The positional indicator notch 111, the locked indicator notch 121, the unlocked indicator notch 123, and the directional indicator 113 can be included on the housing 110 via any suitable process or mechanism, such as by being molded with the housing 110 or via attachment of, for example, adhesive markers.

Also as shown in FIGS. 1A-IC, the second housing portion 120 can include one or more windows 122. In some embodiments, the windows 122 can provide visual access to the contents of a reservoir (e.g., the reservoir 192 described below) such that the user can verify that the contents (e.g., medicine) are suitable for injection (e.g., the user can verify that the contents are unexpired based on color). In some embodiments, the windows 122 can provide visual access to an outer wall of the needle sheath 150. The outer wall of the needle sheath 150 can include a colored portion indicating a status of the injector device 100 (e.g., a green or red region indicating whether the injector device 100 is ready for use and/or penetration).

Figure 2:
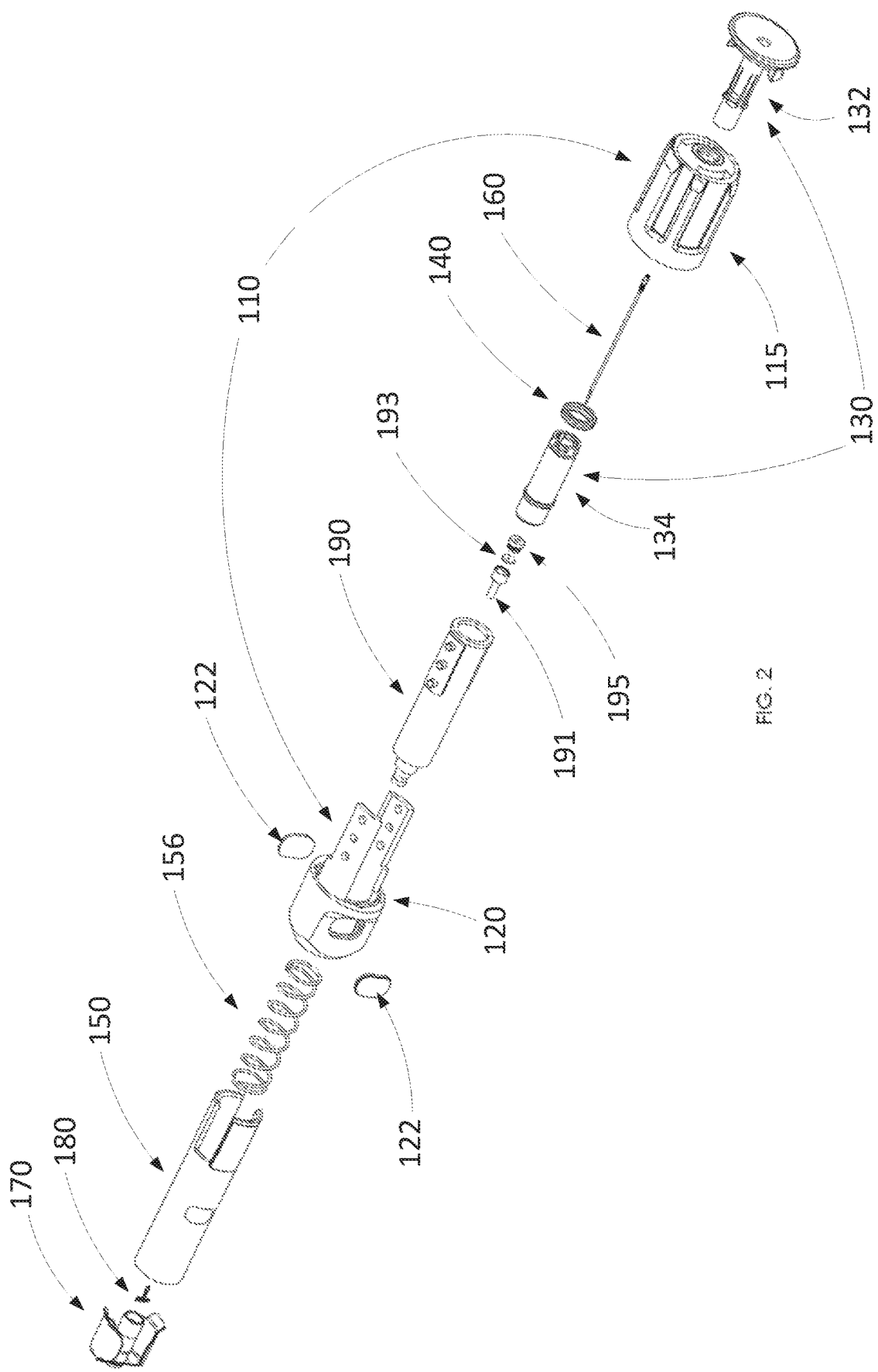
FIG. 2 is an exploded view of the injector device of FIG. 1A.

FIG. 2 is an exploded view of the components of the injector device 100. As shown in FIG. 2, the plunger assembly 130 includes a first plunger portion 132 and a second plunger portion 134. The injector device 100 also includes a needle 160 and a sealing element 140. The injector device 100 further includes an internal cartridge 190 and a guide bushing 191, a guide seal 193, and a catch feature 195 disposed within the internal cartridge 190. A spring 156 can be disposed within the needle sheath 150 and coupled to the internal cartridge 190. Additionally, a needle pull barb 180 can be engaged with the cover 170 and the needle 160, as will be described below.

Figure 3A:
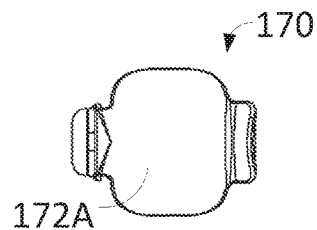
FIGS. 3A-3G are various views of a cover of the injector device of FIG. 1A in a first, attached configuration.
Figures 3B, 3C, 3D, 3E:
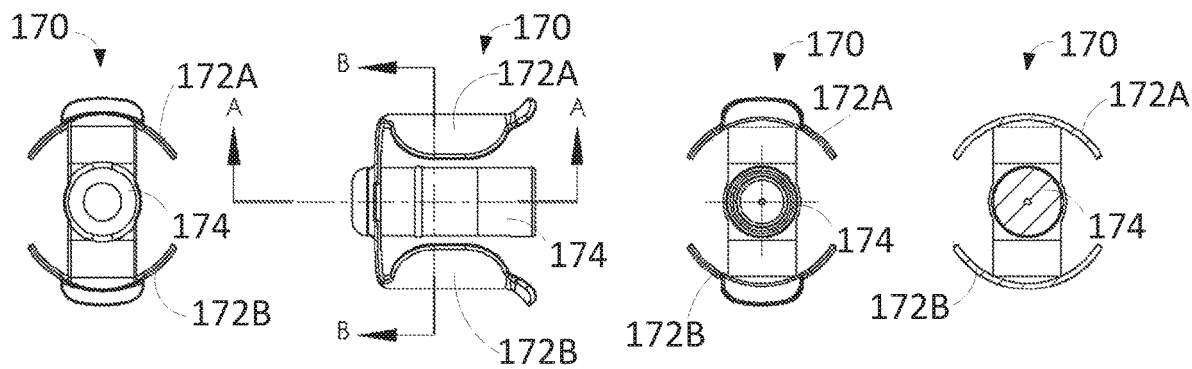
Figure 3F:
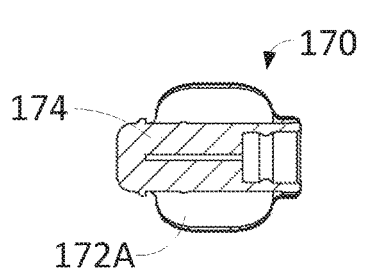
Figure 3G:
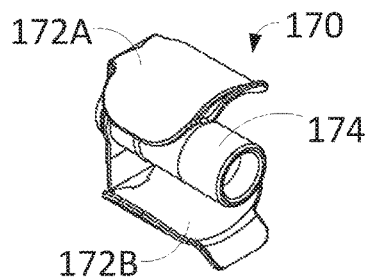

FIGS. 3A-3G are various views of the cover 170 in a first, attached configuration. Specifically, FIG. 3A is a side view of the cover 170, FIG. 3B is a bottom view of the cover 170, FIG. 3C is a front view of the cover 170, and FIG. 3D is a top view of the cover 170. FIG. 3E is a cross-sectional view of the cover 170 taken along line A-A in FIG. 3C. FIG. 3F is a cross-sectional view of the cover 170 taken along line B-B in FIG. 3C. FIG. 3G is a perspective view of the cover 170. As shown, the cover 170 includes a first tab 172A, a second tab 172B, and a stem 174. In the first, attached configuration (i.e., the configuration of the cover 170 when attached to the injector device 100), the first tab 172A and the second tab 172B are arranged such that the stem 174 extends between the first tab 172A and the second tab 172B.

FIGS. 3H-3N are various views of the cover 170 in a second, detached configuration. Specifically, FIG. 3H is a side view of the cover 170, FIG. 3I is a bottom view of the cover 170, FIG. 3J is a front view of the cover 170, and FIG. 3K is a top view of the cover 170. FIG. 3L is a cross-sectional view of the cover 170 taken along line A-A in FIG. 3. FIG. 3M is a cross-sectional view of the cover 170 taken along line B-B in FIG. 3J. FIG. 3N is a perspective view of the cover 170. In the second, detached configuration (i.e., the configuration of the cover 170 after being detached from the injector device 100), the first tab 172A and the second tab 172B are arranged such that the first tab 172A and the second tab 172B extend away from the stem 174. The cover 170 can be transitioned from the first, attached configuration to the second, detached configuration via, for example, folding the first tab 172A and the second tab 172B relative to the stem 174.

The cover 170 can be formed of any suitable material, such as molded rubber. In some further examples, a third or fourth tab may be provided, and/or the tabs may be longer and/or wider, to extend the full length of the injector, and may cover the proximal end of the injector, or entirely encapsulate the injector to provide additional safety and protection. For example, FIGS. 28A-28G are various views of a cover 270. Specifically, FIGS. 28A and 28B are a proximal perspective view and a distal perspective view of the cover 270, respectively. FIGS. 28C, 28D, and 28E are a first side view, a front view, and a second side view (opposite the first side) of the cover 270, respectively. FIGS. 28F and 28G are a top or proximal view and a bottom or distal view of the cover 270, respectively. The cover 270 can be similar in structure and/or function to the cover 170. For example, the cover 270 can include a base 278 including an internal stem 274 having the same structure and/or function to the internal stem 174 of the cover 170. The cover 270 includes a first tab 272A and a second tab 272B. The first tab 272A can optionally include an access flap 273A and the second tab 272B can optionally include an access flap 273B. Each access flap 273A and 273B can be folded relative to the first tab 272A and second tab 272B, respectively. Additionally, the first tab 272A can include an engagement flap 275A and the second tab 272B can include an engagement flap 275B. The engagement flap 275A and the engagement flap 275B can be secured to each other via any suitable coupling mechanism. For example, as shown, the engagement flap 275A can include an engagement button 276A and define an engagement opening (not shown). Similarly, the engagement flap 275B can include an engagement button 276B and define an engagement opening (not shown). The engagement button 276A can have a larger diameter than the engagement opening of the engagement flap 275B and the engagement button 276B can have a larger diameter than the engagement opening of the engagement flap 275A. The engagement button 276A can be inserted through and retained in the engagement opening of the engagement flap 276B, and the engagement button 276B can be inserted through and retained in the engagement opening of the engagement flap 276A. Although not shown, in some embodiments, the engagement flaps 275A and 275B can be reversibly secured via a single engagement button on one of the engagement flaps 275A and 275B and a single engagement opening on the other of the engagement flaps 275A and 275B.

Figure 29A:
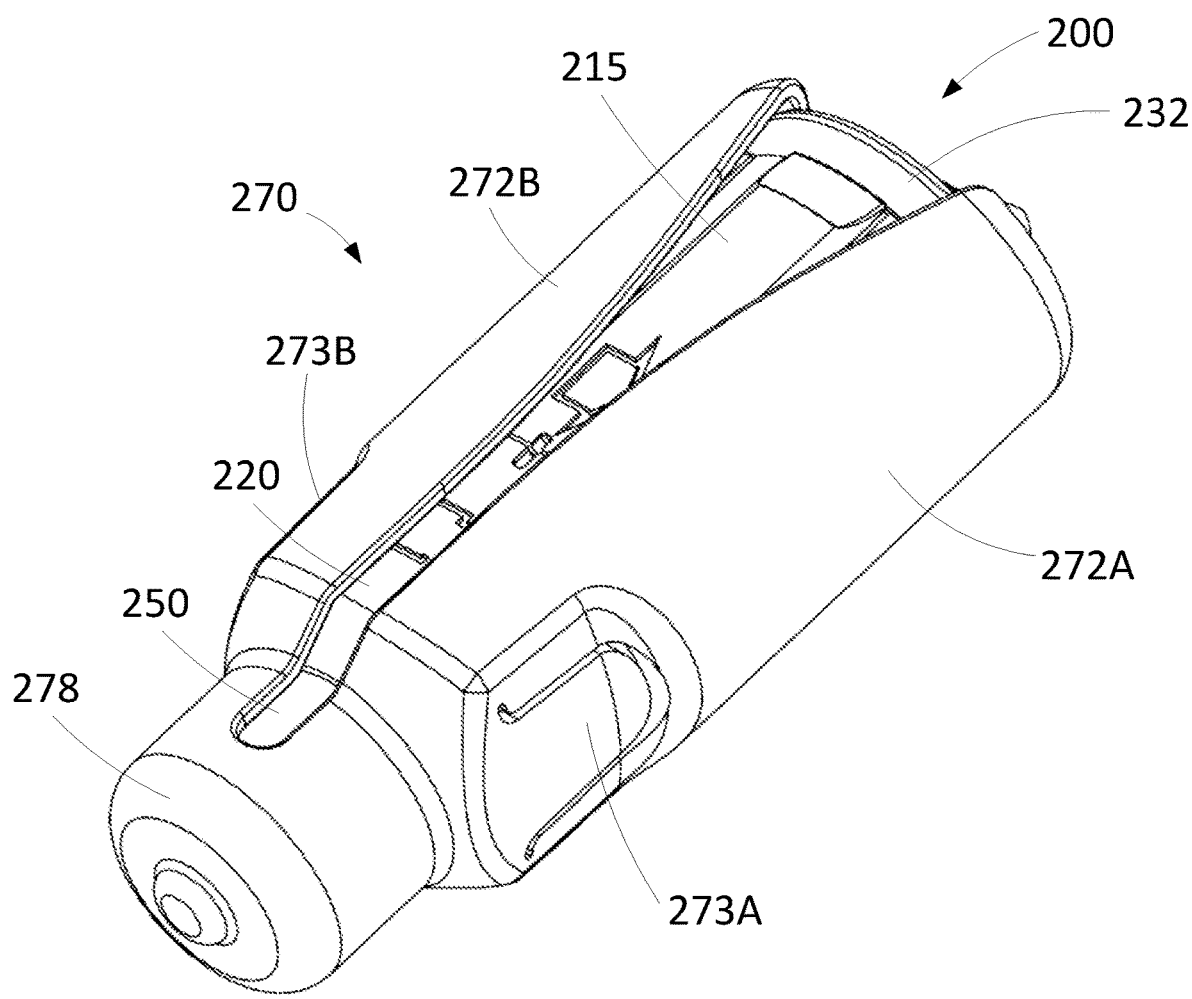
FIGS. 29A and 29B are distal and proximal perspective views, respectively, of the injector device cover of FIGS. 28A-28G coupled to an injector device, according to an embodiment.
Figure 29B:
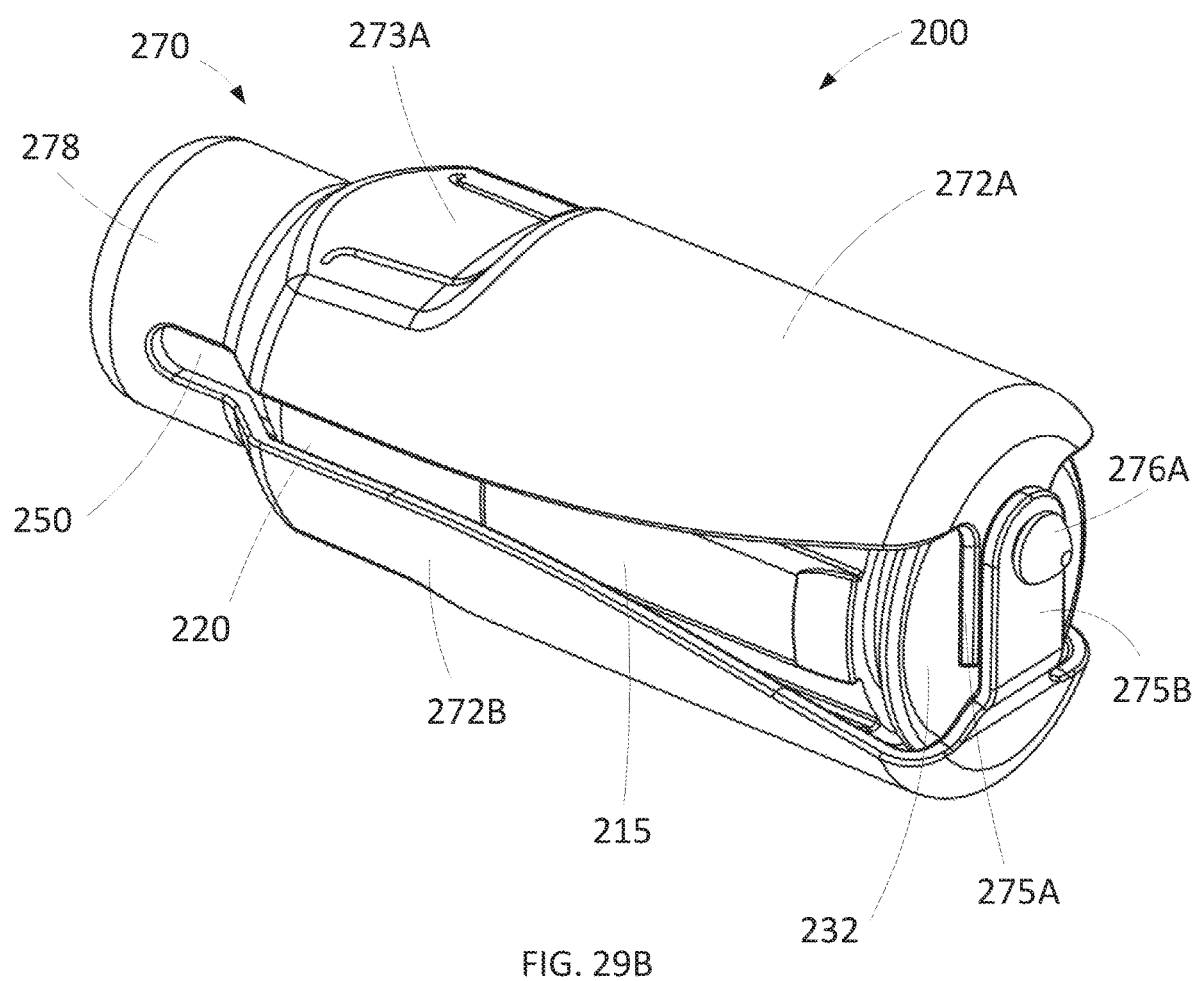
Figure 30A:
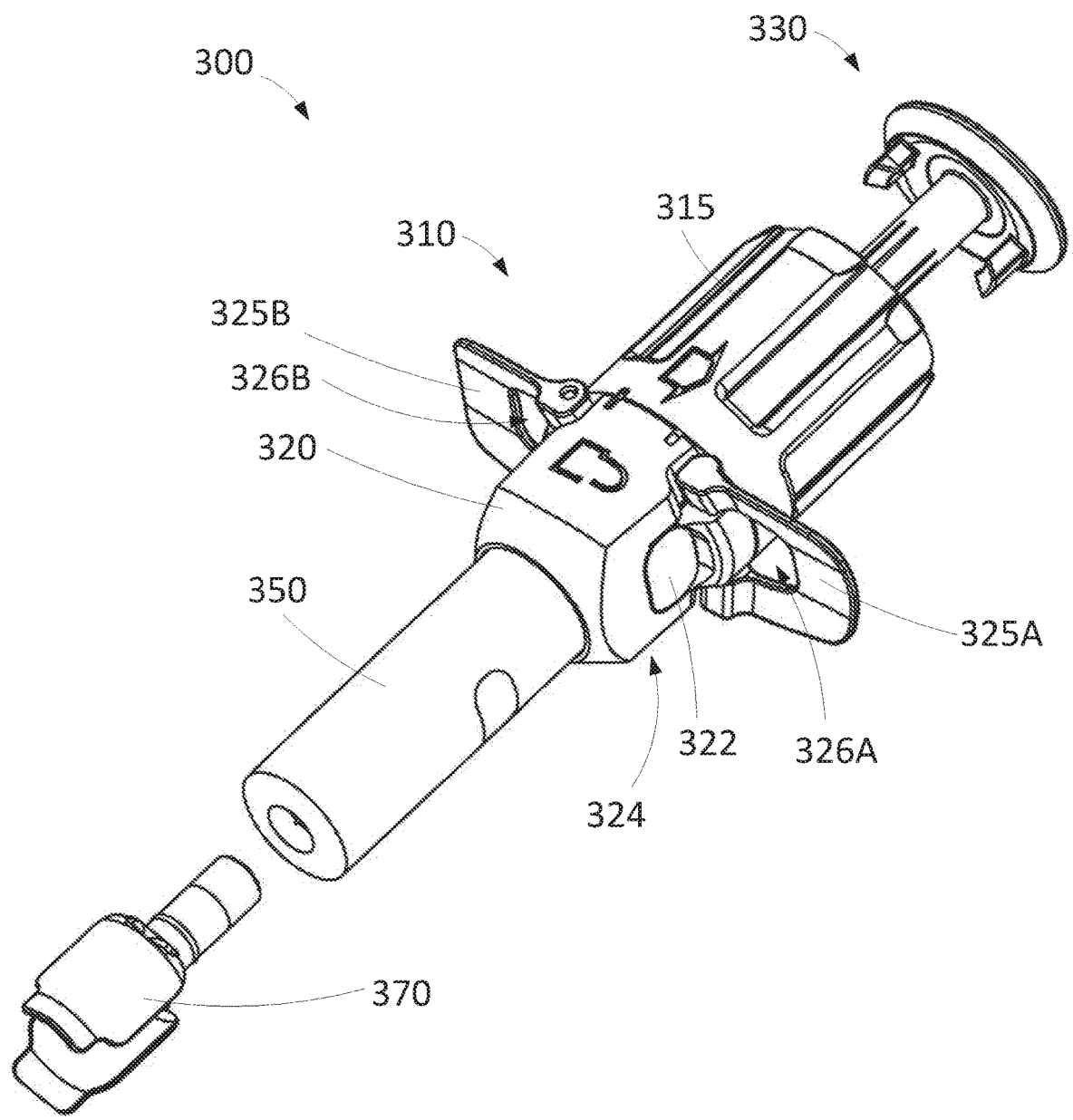
Figure 30D:
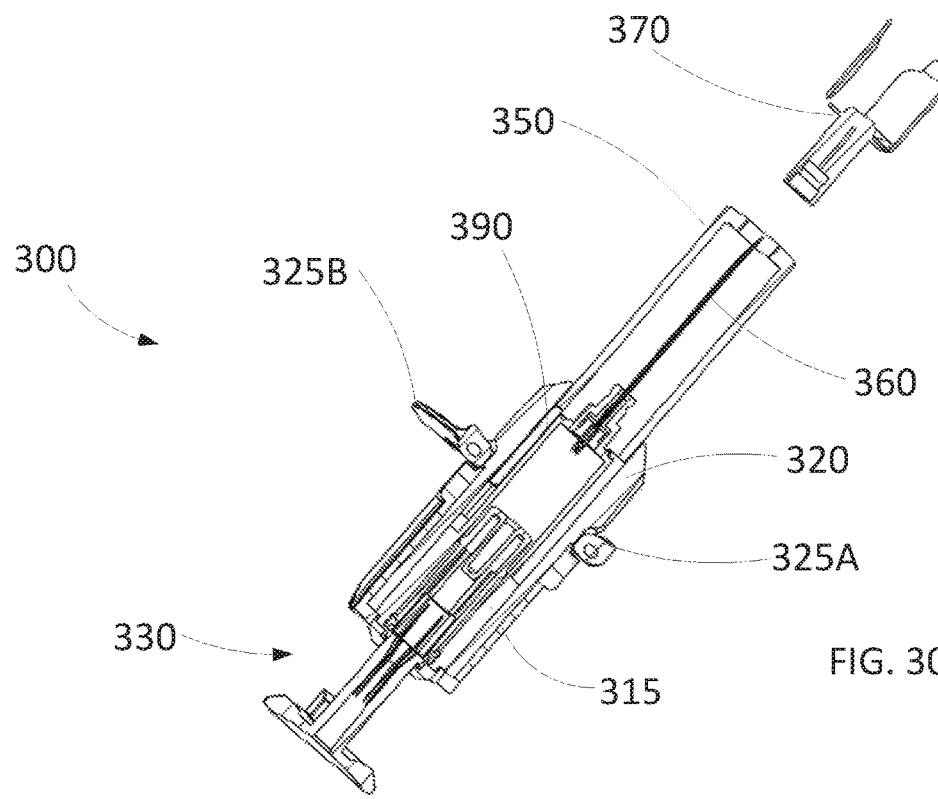
Figure 30E:
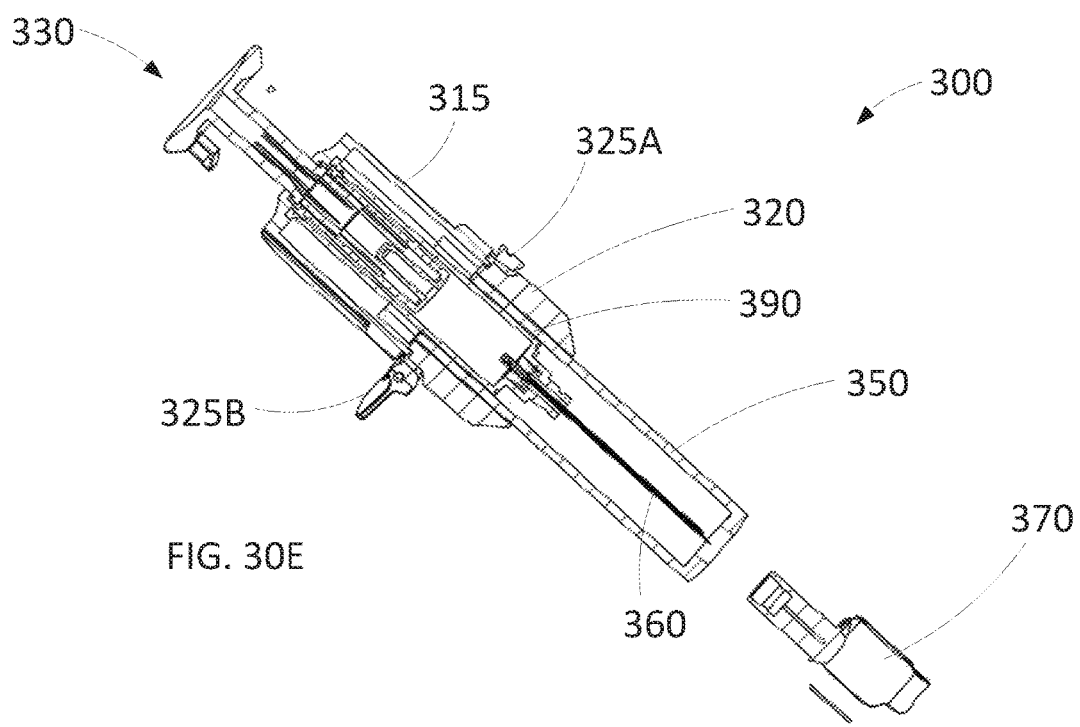

FIGS. 29A and 29B are a front or distal perspective view and a back or proximal perspective view of an injector device 200 including the cover 270. The injector device 200 can be similar in structure and/or function to any of the injector devices described herein, such as injector device 100. For example, the injector device 200 can include a first plunger portion 232, a first housing portion 215, a second housing portion 220, and a needle sheath 250, which can be the same or similar in structure and/or function to the first plunger portion 132, a first housing portion 115, a second housing portion 120, and a needle sheath 150, respectively. As shown, the tabs 272A and 272B can extend from the base 278 of the cover 270, which is coupled to the needle sheath 250, along the sides of the first housing portion 215 and second housing portion 220. The engagement flaps 275A and 275B can be secured to each other on the proximal side of the first plunger portion 232. While the cover 270 is attached to the first housing portion 215 and the second housing portion and secured on the proximal side of the first plunger portion 232, the access flaps 273A and 273B can be folded relative to the cover 270 such that windows on the second housing portion 220 can be viewed (e.g., to see the contents of an internal cartridge). In use, the engagement flaps 275A and 275B can be disengaged from each other and the tabs 272A and 272B can be pulled distally relative to the first housing portion 215 and second housing portion 220. The further use and deployment of the injector device 200 can proceed the same or similarly as described with respect to the injector device 100.

Figure 4A:
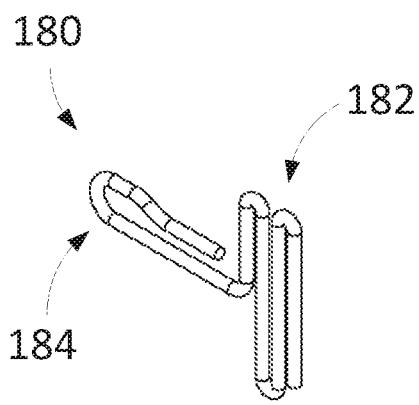
FIGS. 4A-4C are various views of a needle pull barb of the injector device of FIG. 1A.
Figures 4B, 4C:
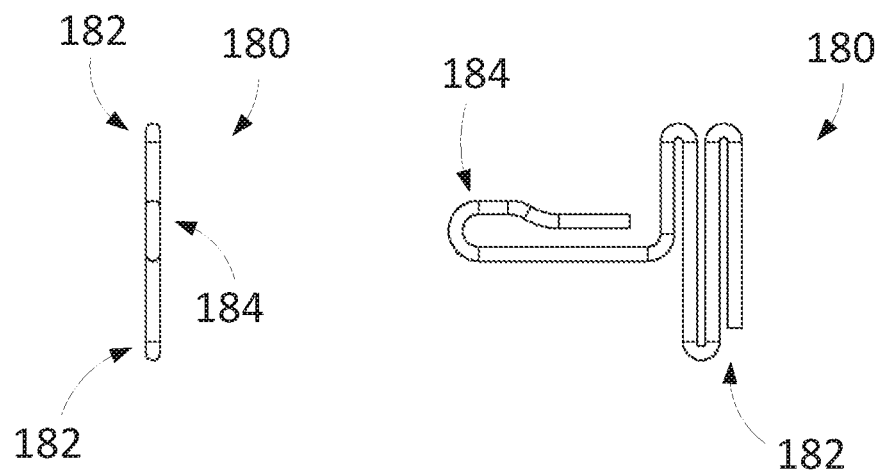

FIGS. 4A-4C are various views of the needle pull barb 180. Specifically, FIG. 4A is a perspective view of the needle pull barb 180, FIG. 4B is a front view of the needle pull barb 180, and FIG. 4C is a side view of the needle pull barb 180. The needle pull barb 180 can have a first end 182 and a second end 184. The first end 182 can be embedded in the cover 170 and the second end 184 can be coupled to the needle 160, as will be described in more detail below. The needle pull barb 180 can be formed of any suitable material and can be, for example, a stainless steel single strand wire or filament.

Figure 5A:
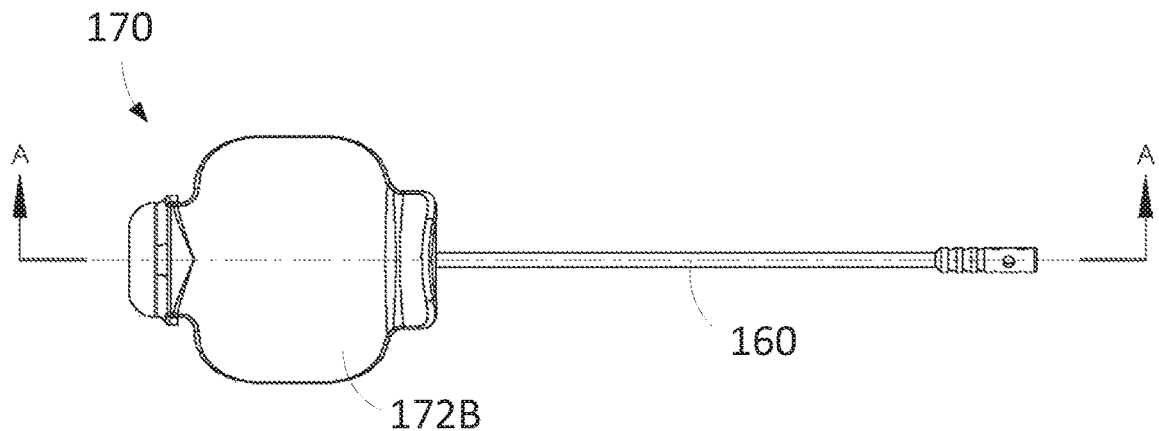
FIGS. 5A-5C are various views of a needle of the injector device of FIG. 1A coupled to the cover of the injector device via the needle pull barb of the injector device.
Figure 5B:
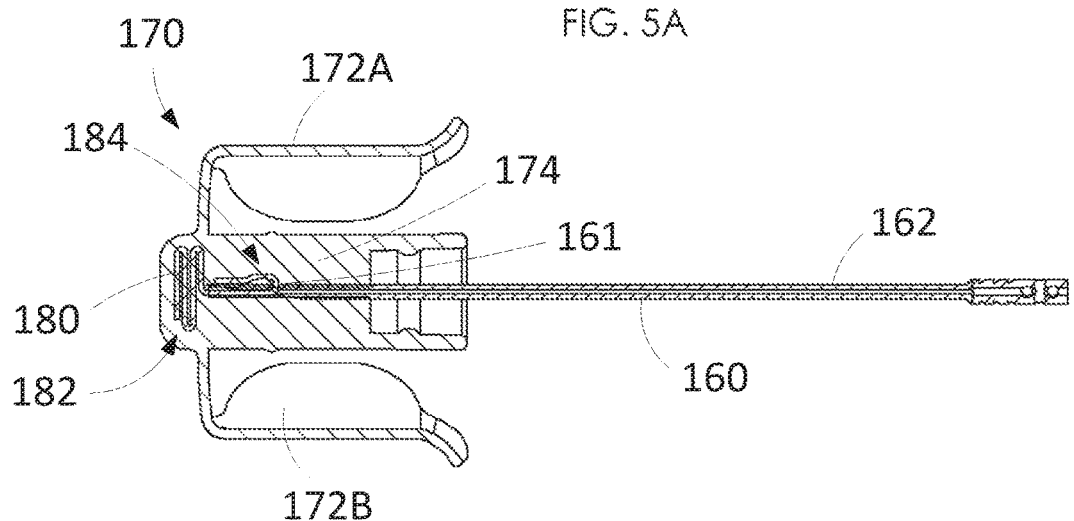
Figure 5C:
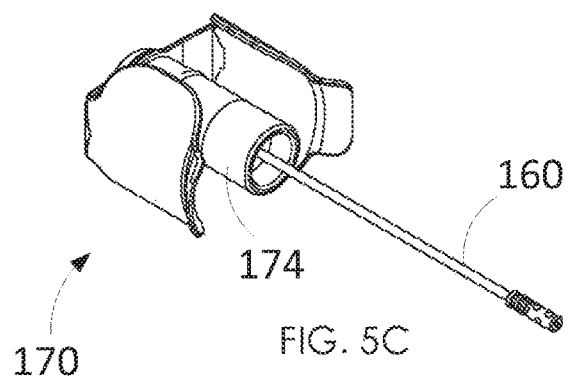

FIGS. 5A-5C are various views of the needle 160 coupled to the cover 170 via the needle pull barb 180. Specifically, FIG. 5A is a side view, FIG. 5B is a cross-sectional view taken along line A-A in FIG. 5A, and FIG. 5C is a perspective view of the needle 160 coupled to the cover 170 via the pull barb 180. As shown in FIGS. 5A-5C, the needle 160 can define a lumen 162 and a hole 161 (as described below with respect to FIGS. 12A-12C). The first end 182 of the needle pull barb 180 can be embedded in the cover 170 such that movement of the cover 170 can control movement of the needle pull barb 180. The second end 184 of the needle pull barb 180 can be coupled to the needle 160 such that when a first force is applied to the cover 170, the cover 170 can pull the needle 160 in the direction of the first force. When a second force (such as a resistive force) is applied to the needle 160, such as a second force opposite in direction from the first force, however, the first force (or a third force applied in the same direction as the first force) can detach the cover 170 from the needle 160. For example, the second end 184 of the needle pull barb 180 can be threaded through the lumen 162 of the needle 160 and out of the hole 161. The second end 184 can then be folded relative to the needle 160 and/or embedded in the cover 170. Upon the application of sufficient force to the cover 170 relative to the needle 160, the cover 170 can pull on the barb 180 such that the barb 180 breaks proximate the location of the hole 161 in the needle 160. The cover 170 can then be fully detached from the needle 160, carrying the pieces of the barb 180 away from the needle 160. Although not shown, in some embodiments, rather than including a needle pull barb, the cover 170 can be formed of a material and sized such that the cover 170 can apply sufficient friction to the needle 160 to translate the needle 160, but can detach from the needle 160 upon the application of a sufficient resistive or retaining force on the needle 160 in the opposite direction of the movement of the cover 170.

FIGS. 6A-6E are various views of the needle sheath 150. Specifically, FIG. 6A is a front view of the needle sheath 150, FIG. 6B is a side view of the needle sheath 150, FIG. 6C is a bottom view of the needle sheath 150, and FIG. 6E is a top view of the needle sheath 150. FIG. 6D is a cross-sectional view of the needle sheath 150 taken along line A-A in FIG. 6A. As shown, the needle sheath 150 includes a first, proximal end 151 and a second, distal end 153. The needle sheath 150 includes a body 152 and projecting portions 154. For example, the needle sheath 150 can include two projecting portions 154.

As described above with reference to FIGS. 1A-1C, the needle sheath 150 can include a number of indication regions 155 (e.g., one or two indication regions). The indication regions 155 can be disposed on the needle sheath 150 such that each indication region aligns with a window 122 of the housing assembly 110 when the injector device 100 is fully assembled and in the locked configuration. In some embodiments, the indication regions 155 are transparent regions of the sidewall of the needle sheath 150. Thus, when the injector device 100 is in the locked configuration, the user can see through the windows 122 of the housing assembly 110 and through the indication regions 155 of the needle sheath 150 into the reservoir 192 (shown in FIG. 8E) of the internal cartridge 190. The user can use this line of sight to verify the suitability of the contents of the internal cartridge 190 for injection, such as by checking the color of the contents to verify the contents have not expired. In some embodiments, the indication regions 155 are colored regions of the sidewall that indicate a status of the device. For example, the indication regions 155 can be a first color, such as red, such that when the injector device 100 is in the locked configuration, the user can see a red indication region 155 through each window 122 of the housing assembly 110, indicating that the device is locked and not ready for injection. In some embodiments, the needle sheath 150 can include additional indicator regions or can be colored in regions outside of the indication regions 155 in a second color, such as green, such that when the needle sheath 150 is extended relative to the housing assembly 110, the user can see a green region through each window 122 of the housing assembly 110, indicating that the device is ready for operation.

Figure 7C:
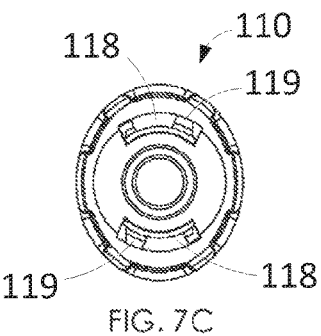
FIGS. 7A-7F are various views of a housing assembly of the injector device of FIG. 1A.
Figures 7A, 7B, 7D, 7E:
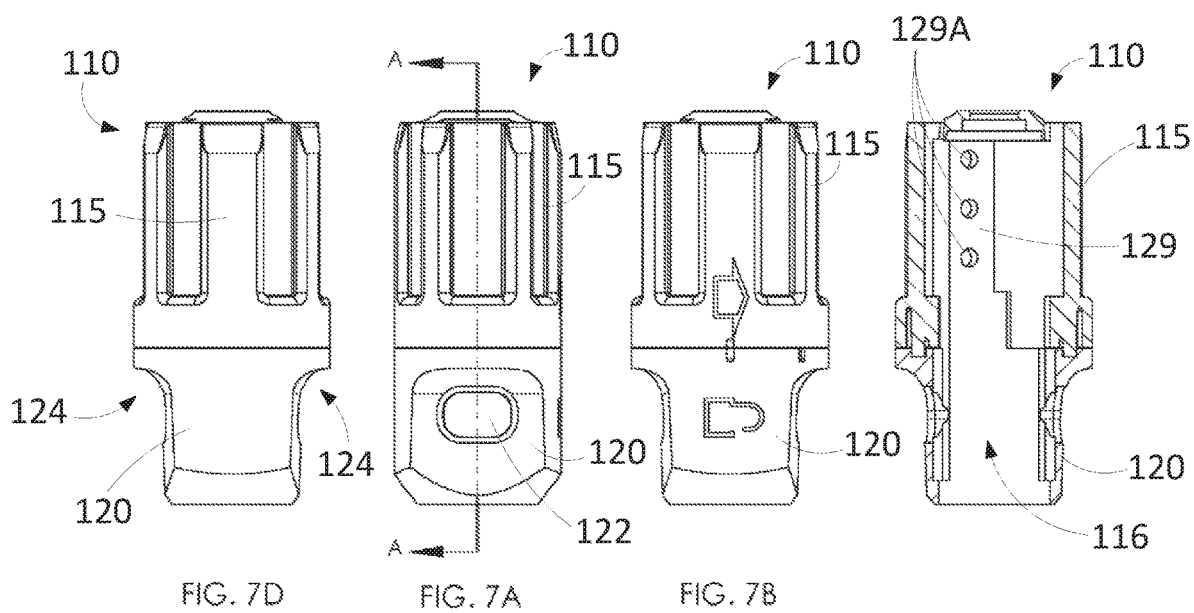
Figure 7F:
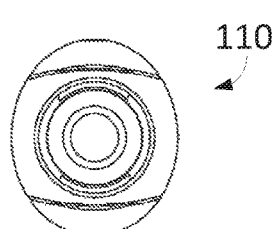

FIGS. 7A-7F are various views of the housing assembly 110. Specifically, FIG. 7A is a front view of the housing assembly 110, FIG. 7B is a side view of the housing assembly 110, FIG. 7C is a top view of the housing assembly 110, FIG. 7D is a side view opposite the side view of FIG. 7B of the housing assembly 110, and FIG. 7F is a bottom view of the housing assembly 110. FIG. 7E is a cross-sectional view of the housing assembly 110 taken along line A-A in FIG. 7A. As shown and described above, the housing assembly 110 include the first housing portion 115 and the second housing portion 120. The second housing portion 120 can be shaped to define two recesses 124 in the outer surface of the second housing portion 120. As shown in FIG. 7E, the first housing portion 115 and the second housing portion 120 can collectively define an interior cavity 116. The first housing portion 115 and the second housing portion 120 can be coupled via any suitable coupling mechanism that allows for the first housing portion 115 to be rotated relative to the second housing portion 120. For example, although not shown, the first housing portion 115 and the second housing portion 120 can be coupled via a circlip or via an expandable spring within a groove of the first housing portion 115 or the second housing portion 120.

Figure 16B:
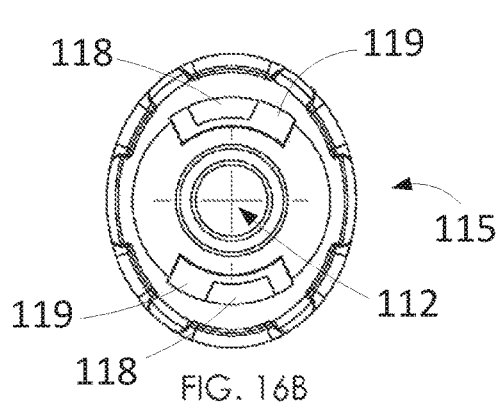
FIGS. 16A-16E are various views of a first housing portion of the injector device of FIG. 1A.

As shown in FIG. 7C, two slots 119 can be defined in a proximal end wall of the first housing portion 115 (also shown in FIG. 16B). Additionally, the first housing portion 115 can include a retaining tab 118 extending into each slot 119.

In some further embodiments, the housing assembly 110 may further comprise hinged or fold-out finger handles at the recesses 124 to provide additional surface area to engage the user's fingers during injection. For example, FIGS. 30A-30E are various views of an injector device 300. The injector device 300 can be the similar in structure and/or function to any of the injector devices described herein, such as the injector device 100. For example, the injector device 300 can include a housing assembly 310 including a first housing portion 315 and a second housing portion 320, a needle sheath 350, a cover 370, a plunger assembly 330, an internal cartridge 390, and a needle 360, which can be the same or similar in structure and/or function to the housing assembly 110 including a first housing portion 115 and a second housing portion 120, a needle sheath 150, a cover 170, a plunger assembly 130, an internal cartridge 190, and a needle 160, respectively. As shown, the injector device 300 can include a first finger handle 325A and a second finger handle 325B coupled to the second housing portion 320. The first finger handle 325A and the second finger handle 325B can be rotated relative to the second housing portion 320 between an undeployed and a deployed configuration. In an undeployed configuration, the finger handles 325A and 325B can be disposed against the second housing portion 320 within the recesses 324 of the second housing portion 320. As shown, the first finger handle 325A can define an opening 326A and the second finger handle 325B can defined an opening 326B such that, in the undeployed configuration, the windows 322 of the second housing portion 320 are not obstructed by the first finger handle 325A and the second finger handle 325B. In the deployed configuration, the finger handles 325A and 325B can project laterally from the housing 320 such that a user's fingers can be placed into engagement with the distal side of the finger handles 325A and 325B during injection. In some embodiments, the finger handles 325A and 325B can be transitioned from the undeployed to the deployed configuration manually by a user. In some embodiments, each of the finger handles 325A and 325B can automatically transition from the undeployed to the deployed configuration via a spring (not shown). For example, in embodiments including a cover similar to the cover 270, the finger handles 325A and 325B can automatically deploy after the cover tabs are disengaged from the finger handles 325A and 325B.

Figure 8C:
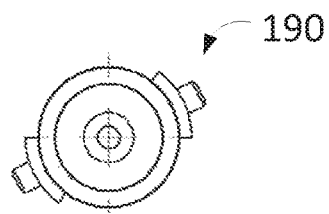
FIGS. 8A-8F are various views of an internal cartridge of the injector device of FIG. 1A.
Figures 8A, 8B, 8D, 8E:
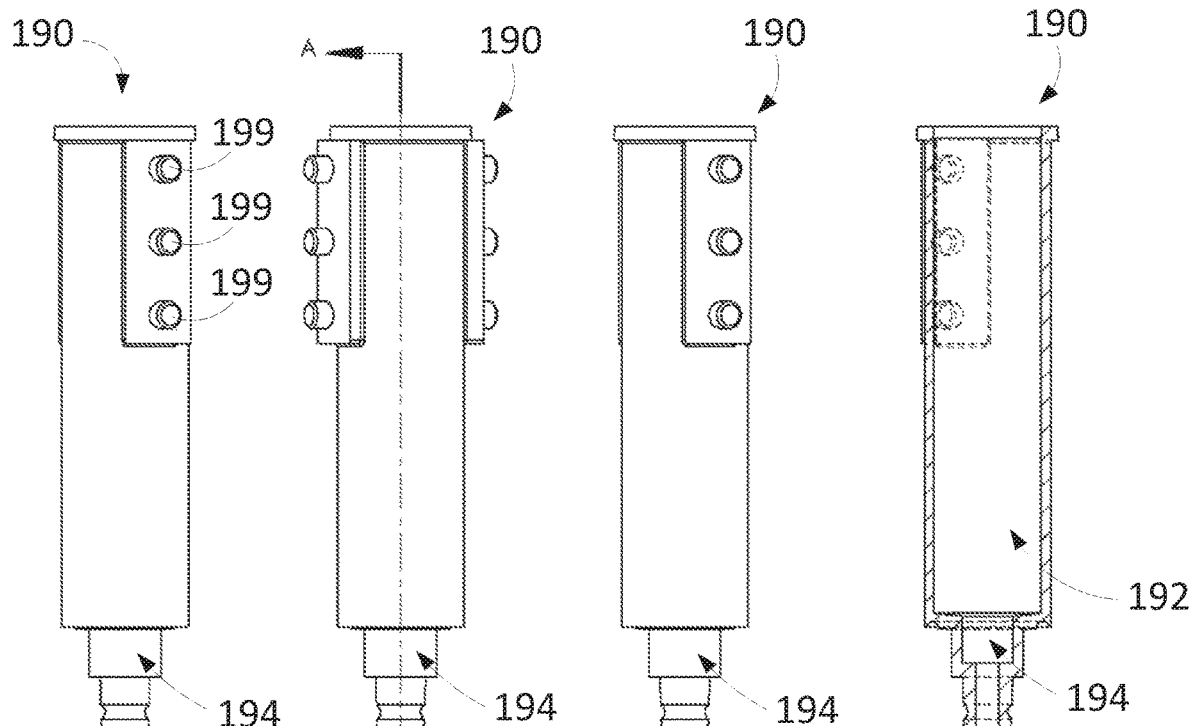
Figure 8F:
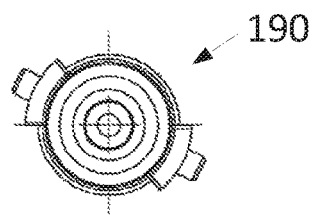

FIGS. 8A-8F are various views of the internal cartridge 190. Specifically, FIG. 8A is a front view of the internal cartridge 190, FIG. 8B is a side view of the internal cartridge 190, FIG. 8C is a top view of the internal cartridge 190, FIG. 8D is a side view opposite the side view of FIG. 8B of the internal cartridge 190, and FIG. 8F is a bottom view of the internal cartridge 190. FIG. 8E is a cross-sectional view of the internal cartridge 190 taken along line A-A in FIG. 8A. As shown, the internal cartridge 190 includes a stepped outlet 194 and one or more mating features 199. In this example, the internal cartridge 190 can include three mating features 199 on each side of the internal cartridge 190 such that the internal cartridge 190 is configured to engage with the housing assembly 110 via the mating features 199. Additionally, the internal cartridge 190 can define a reservoir 192 configured to hold medicament for injection by the injector device 100.

Figure 9B:
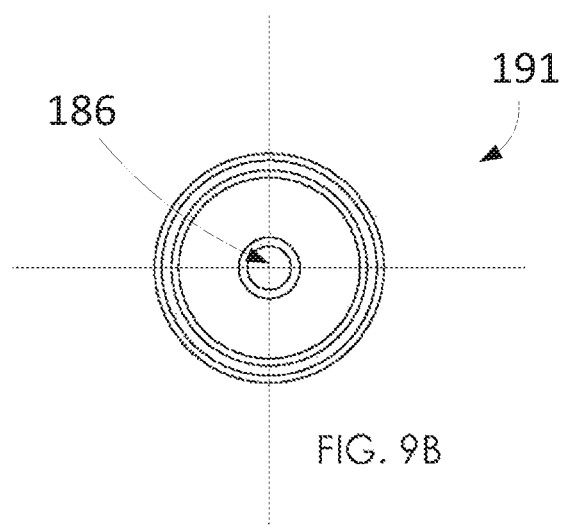
FIGS. 9A-9C are a front view, a top view, and a perspective view, respectively, of a guide bushing of the injector device of FIG. 1A.
Figure 9A:
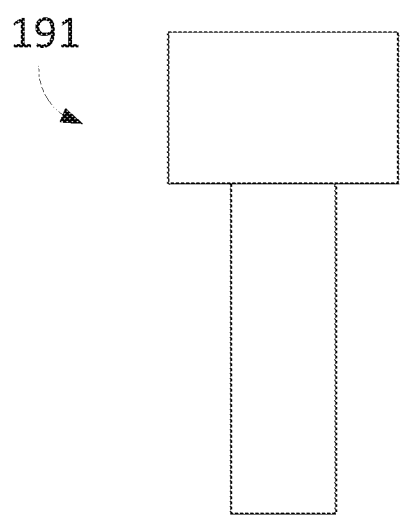
Figure 9C:
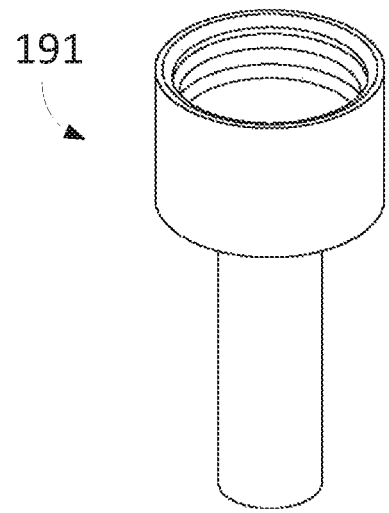

FIGS. 9A-9C are a front view, a top view, and a perspective view, respectively, of a guide bushing 191. The guide bushing 191 can be shaped and sized to be disposed within the outlet 194 of the internal cartridge 190. The guide bushing 191 can define a lumen 186. The outer diameter of the lumen 186 can be similar to the outer diameter of the needle 160 such that the guide bushing 191 can assist in directing the needle 160 along a central longitudinal axis of the injector device 100 as the needle 160 is translated distally. In some examples, the guide bushing 191 may have a length in the range of about 6 mm to about 15 mm, or about 5 mm to about 18 mm.

FIGS. 10A-10C are a front view, a top view, and a perspective view, respectively, of a guide seal 193. The guide seal 193 defines a central opening 193A and is shaped and sized to be disposed in the outlet 194 of the internal cartridge 190. The central opening 193A of the guide seal 193 can be shaped and sized to provide a seal around the needle 160 such that fluid in the reservoir 192 of the internal cartridge 190 does not leak from the internal cartridge 190 proximate the outlet 194. Thus, the guide seal 193 can form a distal boundary of the reservoir 192.

FIGS. 11A-11B are various views of the catch feature 195. Specifically, FIG. 11A is a front view of the catch feature 195, FIG. 11B is a top view of the catch feature 195, and FIG. 11C is a perspective view of the catch feature 195. FIG. 11D is a cross-sectional view taken along line A-A in FIG. 11A. As shown, the catch feature 195 defines a lumen 195A. The inner wall of the catch feature 195 surrounding the lumen 195A includes barbs 197. The barbs 197 can be shaped such that a distal-facing surface of each barb 197 is perpendicular to a central longitudinal axis of the catch feature 195 running through the lumen 195A, and a proximal surface of each barb 197 is angled relative to the distal-facing surface. Thus, an engagement feature 168 (shown and described in FIGS. 12A-12C) of the needle 160 can be translated distally through the lumen 195A, but the barbs 197 will prevent proximal movement of the engagement feature 168. The catch feature 195 can be formed of any suitable material and by any suitable process. For example, the catch feature 195 can be molded or machined in high-density nylon.

Figures 12A, 12B, 12C:
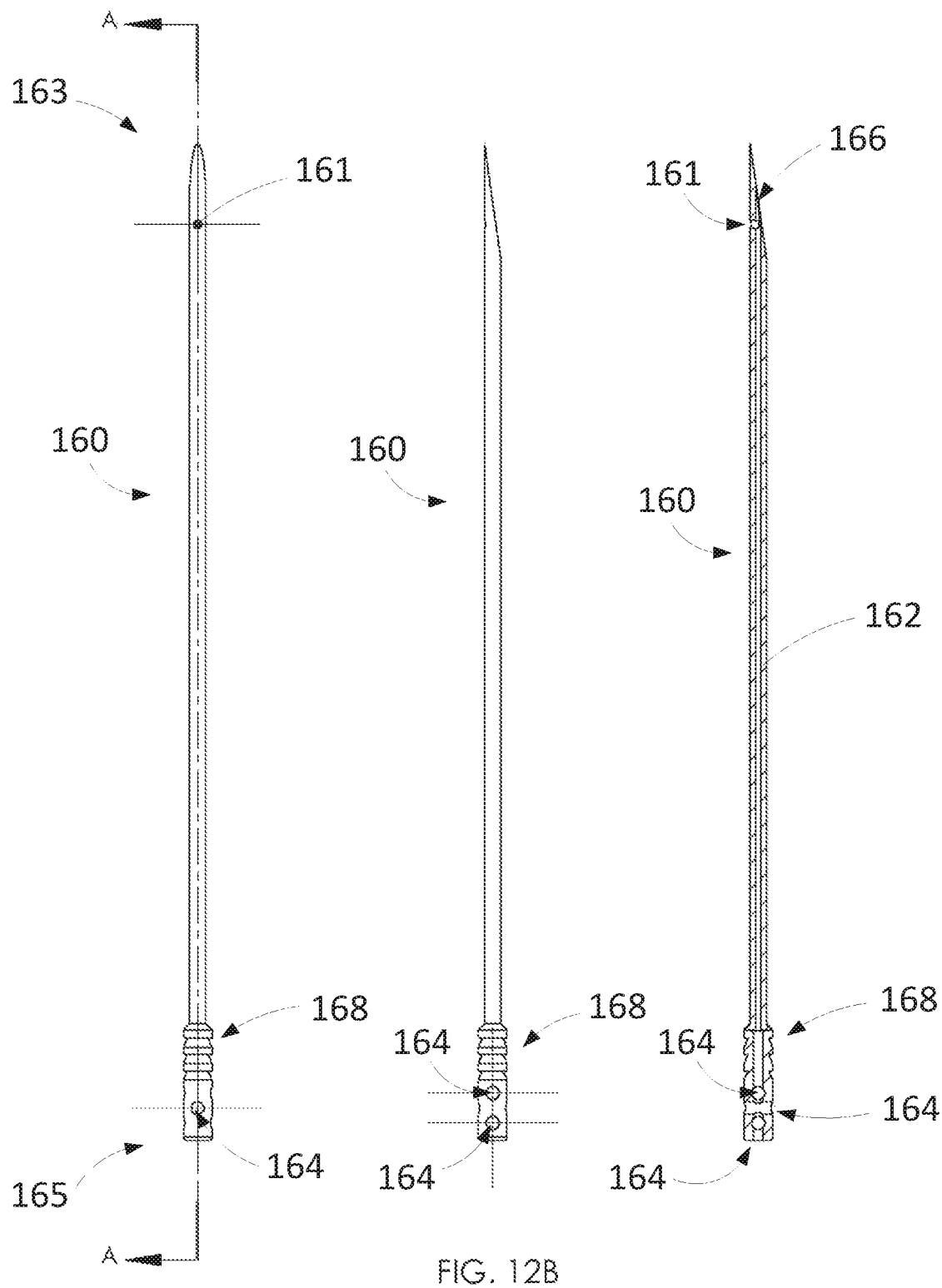
FIGS. 12A-12C are various views of the needle of the injector device of FIG. 1A.

FIGS. 12A-12C are various views of the needle 160. Specifically, FIG. 12A is a front view of the needle 160, FIG. 12B is a side view of the needle 160, and FIG. 12C is a cross-sectional view of the needle 160 taken along line A-A in FIG. 12A. The needle 160 has a first end 165, a second end 163, and defines a lumen 162 extending from the first end 165 to the second end 163. As shown in FIGS. 12A-12C, the needle 160 can define a number of inlets 164 in fluid communication with the lumen 162. The second end 163 of the needle 160 can include a needle tip and an outlet 166. Additionally, as described above, the needle 160 can define a hole 161 for engagement with the needle pull barb 180.

Additionally, the needle 160 can include an engagement feature 168 proximate the first end 165 of the needle 160. The engagement feature 168 can include a number of engagement portions shaped to engage with the barbs 197 of the catch feature 195 such that the needle 160 can be moved distally relative to the catch feature 195 but is prevented from moving proximally.

FIGS. 13A-13C are various views of the internal cartridge 190, the needle 160, the guide bushing 191, the guide seal 193, and the catch feature 195 in an injection configuration in which the engagement feature 168 of the needle 160 is engaged with the catch feature 195. Specifically, FIG. 13A is a front view, FIG. 13B is a cross-sectional view taken along line A-A of FIG. 13A, and FIG. 13C is a top view. As shown in FIG. 13B, the distance from the proximal end of the internal cartridge 190 to the distal end of the needle 160 can be a length L1. The needle 160 can have a length L2. The injection depth of the needle 160 relative to the skin (represented by line S) can be L3. In some embodiments, the length L1 can be, for example, about 3.22 inches. In some embodiments, the length L2 can be, for example, about 1.7 inches. In some embodiments, the length L3 can be, for example, about 0.9 inches.

As shown in FIG. 13C, the internal cartridge 190 can have an inner diameter D1 and an outer diameter D2. The inner diameter D1 can be, for example, about 0.355 inches. The outer diameter D2 can be, for example, about 0.434 inches.

Figures 31A, 31B:
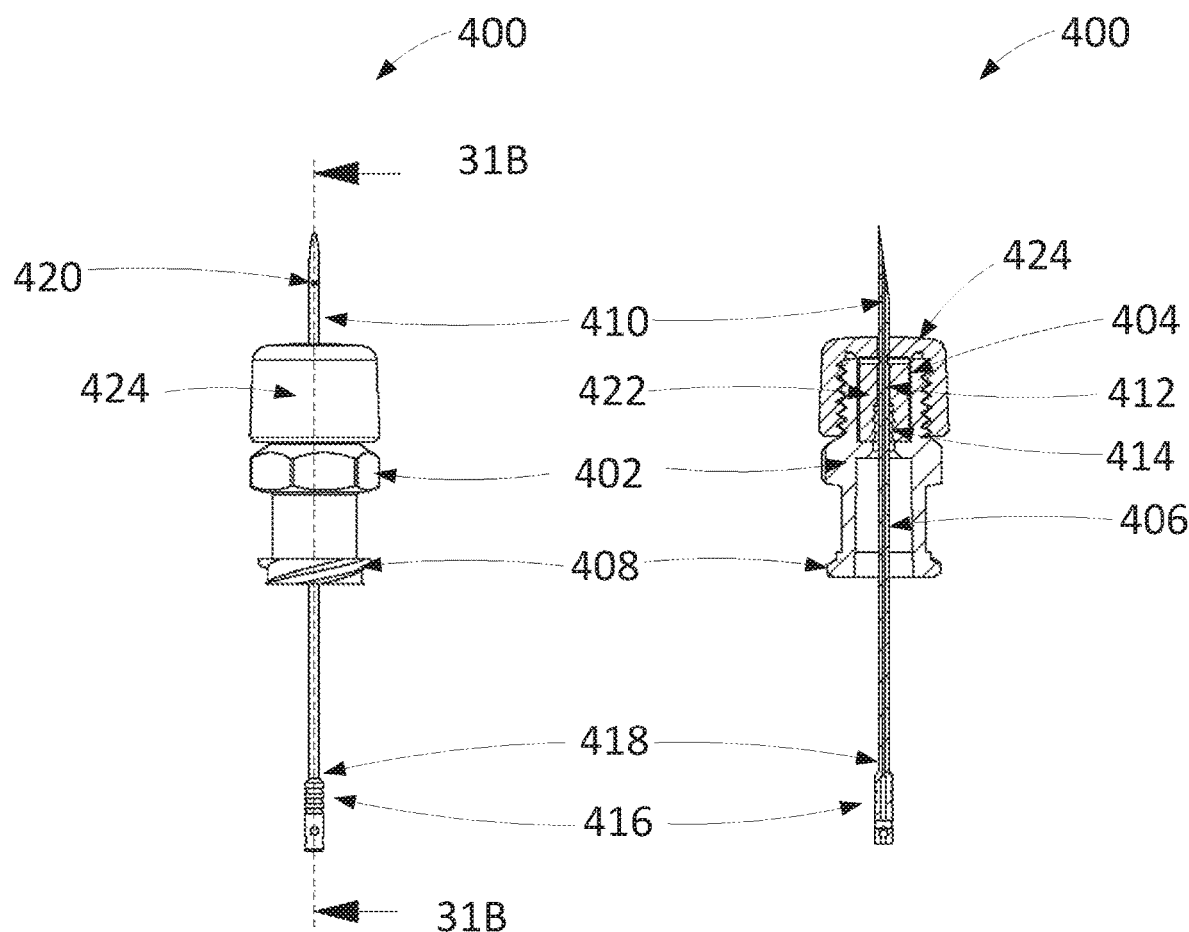
FIGS. 31A and 31B are side elevational and longitudinal cross-sectional views, respectively of a separate needle hub assembly in a retracted configuration that may be used with a separate syringe.
Figures 31C, 31D:
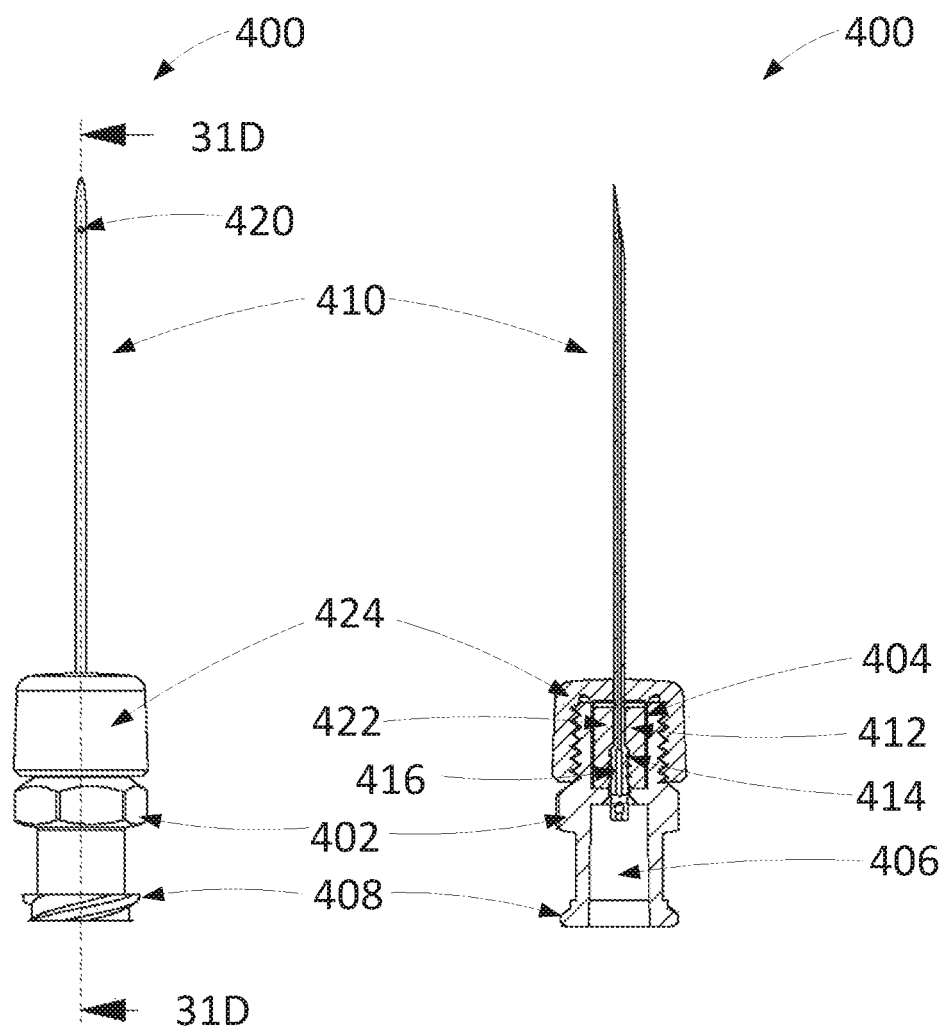
FIGS. 31C and 31D depict the needle hub assembly of FIGS. 31A and 31B in an extended position, respectively.
Figures 31E, 31F:
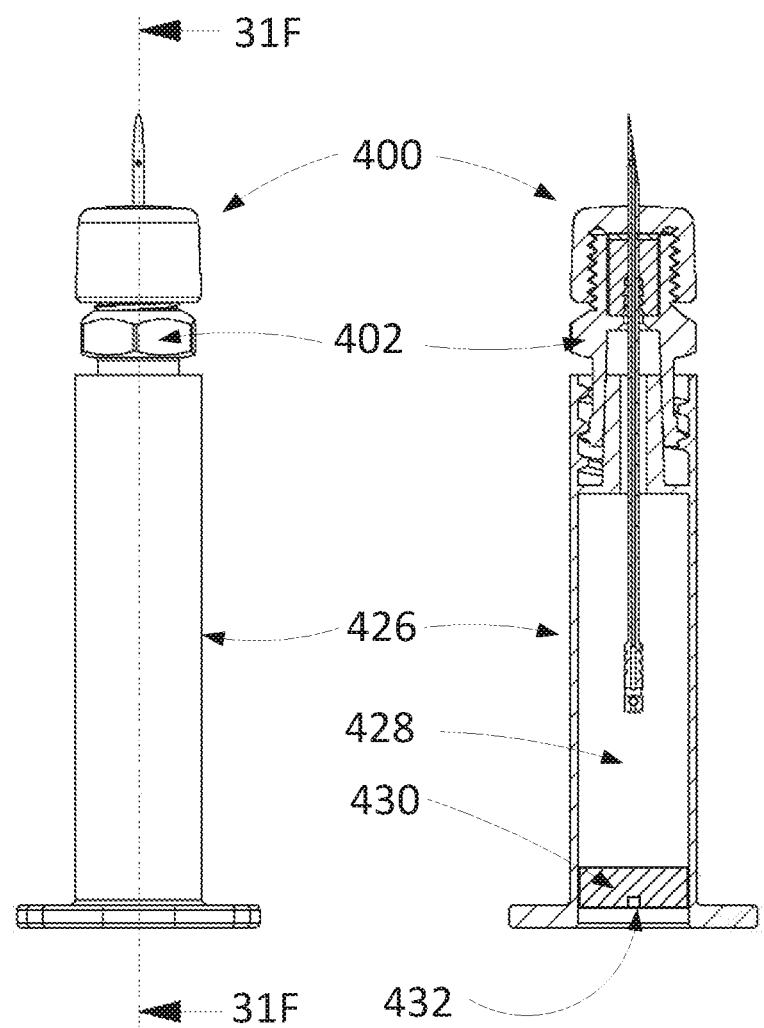
FIGS. 31E and 31F depict the needle hub assembly of FIGS. 31A and 31B attached to a syringe, respectively.

In some embodiments, as shown in FIGS. 31E to 31F, the needle assembly 400 may be provided on a separate needle hub 402 that is attachable to a separate syringe or medicament cartridge 426. The separate syringe may be a standardized syringe or a customized syringe or cartridge. In these embodiments, the needle hub 402 include one or more internal cavities 404, 406 with an attachment interface 408, such as a male Luer interface that is attachable to the distal end of a syringe. Any of a variety of other attachment interfaces may be used, including a female Luer or a friction fit, for example. In the embodiment depicted in FIGS. 31A to 31D, the needle 410 slidably resides in a needle lumen 412 and the cavity 404, 406 of the hub 402. A needle catch structure 414 is also provided with the needle lumen 412 to receive the corresponding and complementary bushing or hub catch structure 416 that is located on the proximal end 418 of the needle 410, as shown in FIGS. 31C and 31D. The needle 410 may also include a transverse or side opening 420 to receive a pull wire and cap as described elsewhere herein. As shown, the needle lumen 412 and the needle catch structure 414 are provided on a bushing 422 located in the distal cavity 404 of the assembly 400. The bushing 422 is retained in the distal cavity 404 by a cap 424. The cap 424 may be threadably attached to the rest of the hub 402, but in other examples may be welded or bonded to the hub, or attached by other mechanical interfaces. In still other examples, the needle lumen may be integrally formed with the hub and a bushing and/or cap is not used. In other examples, a guide bushing, a guide seal, and a catch feature maybe provided inside a single cavity of the needle hub, similar to the embodiments depicted in FIG. 2. The needle hub assembly 400 may be provided as a separate product, optionally with a pull wire and cap, and/or outer housing components as described elsewhere herein, to a contract manufacturer of a prefilled syringe or medicament cartridge, as part of the manufacturing, assembly or packaging process of the device. Referring back to FIGS. 31E and 31F, the internal cavity 428 of the syringe 426 may be filled with the therapeutic agent prior to attachment of the needle hub 402 and may include a slidable seal 430 that may be engaged or coupled to the distal end of a plunger rod (not shown) at an engagement structure 432 during use or during manufacture in order to dispense the therapeutic agent when the slidable seal 430 is displaced distally.

Figure 14A:
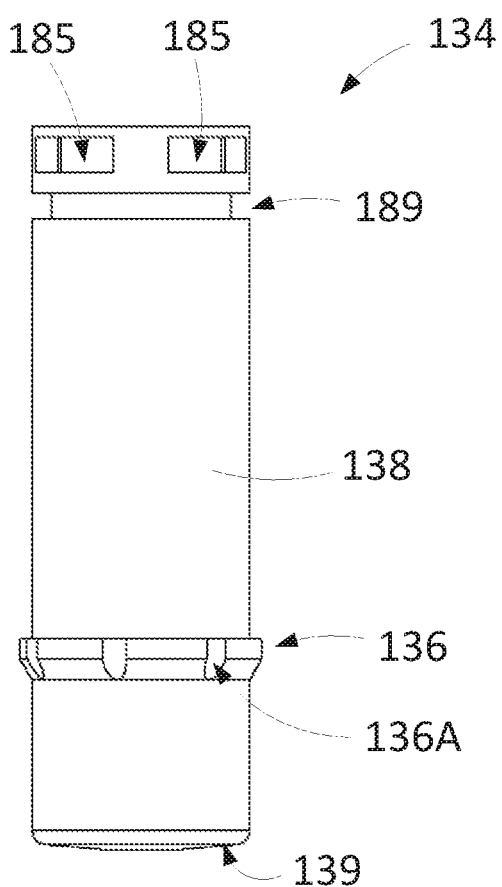

FIGS. 14A-14D are various views of the second plunger portion 134 of the plunger assembly 130. Specifically, FIG. 14A is a front view of the second plunger portion 134. As shown in FIG. 14A, the second plunger portion 134 includes a distal end wall 139 and a sidewall 138. The second plunger portion 134 also includes a guiding feature 136. The guiding feature 136 can maintain the axial alignment of the rubber seal 140, the first plunger portion 138 and/or second plunger portion 134 within the internal cartridge 190 such that the second plunger portion 134 is disposed on and translates along a central axis of the injection device 100. The guiding feature 136 defines recesses 136A such that fluid can flow from an area on a first side of the guiding feature 136 to an area on a second side of the guiding feature 136. The guiding feature may be located at the distal end of the second plunger portion 134 or proximal to the distal end of the second plunger portion 134, e.g. at a location 10%, 20%, 300%, 40%, or 50%, of the length of the length of the second plunger portion 134, relative to the distal end of the plunger portion 134, for example. The second plunger portion 134 defines a seal recess 189 near the proximal end of the second plunger portion 134. The seal recess 189 is shaped and sized to receive the sealing element 140. The second plunger portion 134 also defines four tab recesses 185 near the proximal end of the second plunger portion 134.

FIG. 14B is a front view of the second plunger portion 134 in combination with the sealing element 140. FIG. 14C is a cross-sectional view of the second plunger portion 134 in combination with the sealing element 140 taken along line A-A in FIG. 14B. FIG. 14D is a top view of the second plunger portion 134 in combination with the sealing element 140. As shown in FIG. 14C, the second plunger portion 134 includes an internal compartment 187 defining an interior cavity 198. The internal compartment 187 can be shaped and sized to receive the proximal end of the needle 160 in the locked configuration of the injector device 100. As shown, the internal compartment 187 can be formed of a substantially cylindrical internal sidewall and a proximal end wall. The interior cavity 198 defined by the internal compartment 187 can be in fluid communication with the interior of the internal cartridge 190 and can thus form a boundary of the reservoir 192. As shown in FIG. 14D, the second plunger portion 134 can define four guide recesses 188 on an inner surface of the second plunger portion 134. A tab recess 185 is disposed in each guide recess 188.

Figure 15B:
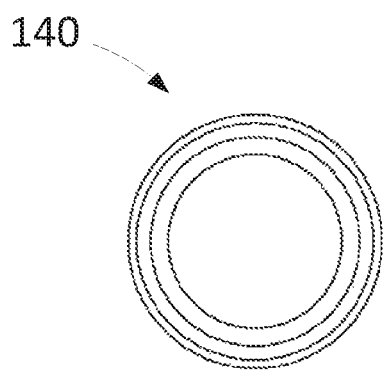
FIGS. 15A-15C are various views of a sealing element of the injector device of FIG. 1A.
Figure 15C:
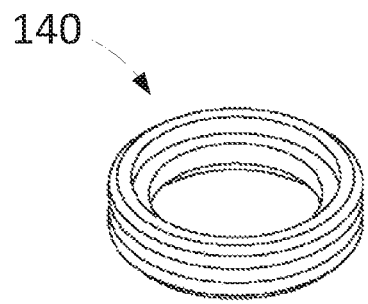
Figure 15A:
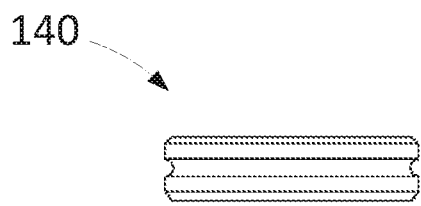

FIGS. 15A-15C are various views of the sealing element 140. Specifically, FIG. 15A is a front view of the sealing element 140, FIG. 15B is a top view of the sealing element 140, and FIG. 15C is a perspective view of the sealing element 140. The sealing element 140 can be formed of any suitable material configured to provide a seal between the second plunger portion 132 and the internal wall of the internal cartridge 190.

Figure 16D:
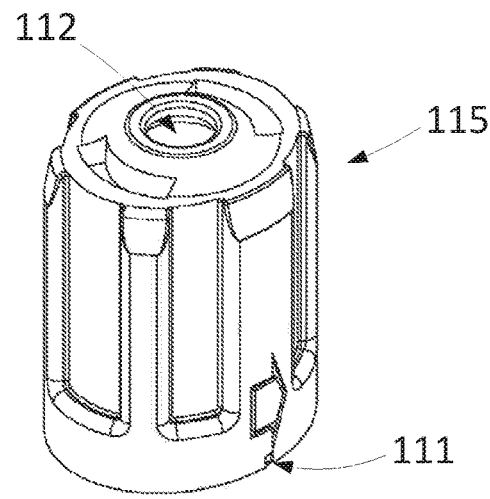
Figure 16A:
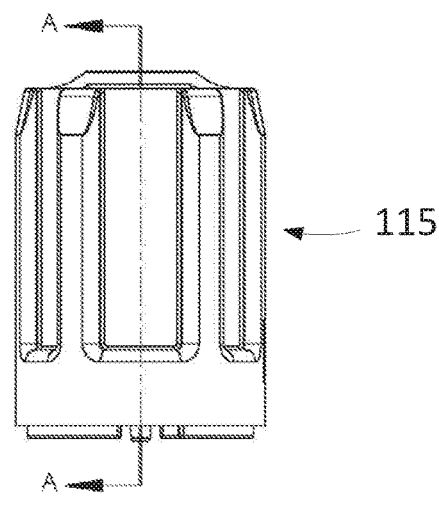
Figure 16E:
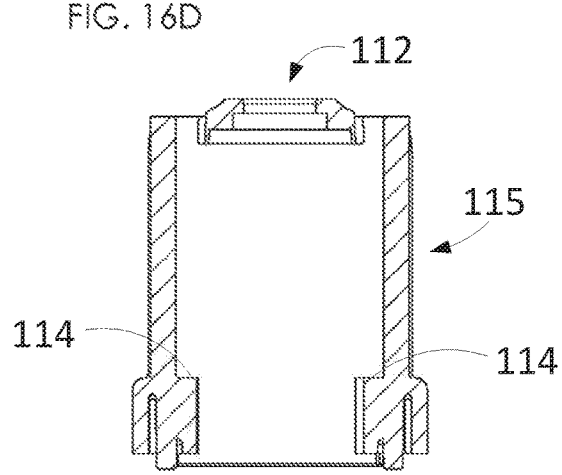
Figure 16C:
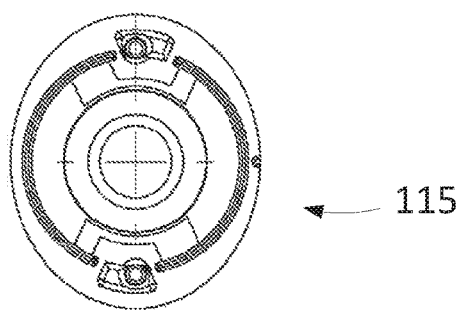

FIGS. 16A-16E are various views of the first housing portion 115. Specifically, FIG. 16A is a front view of the first housing portion 115, FIG. 16B is a top view of the first housing portion 115, FIG. 16C is a bottom view of the first housing portion 115, and FIG. 16D is a perspective view of the first housing portion 115. FIG. 16E is a cross-sectional view of the first housing portion 115 taken along line A-A in FIG. 16A. As shown, the first housing portion 115 defines a proximal opening 112. Additionally, as shown in FIG. 16E, the first housing portion 115 includes two retaining portions 114 extending inward from an internal wall of the first housing portion 115.

Figure 16F:
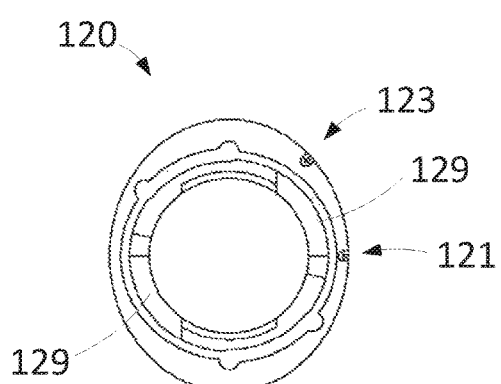
FIGS. 16F-16J are various views of the second housing portion of the injector device of FIG. 1A.
Figure 16G:
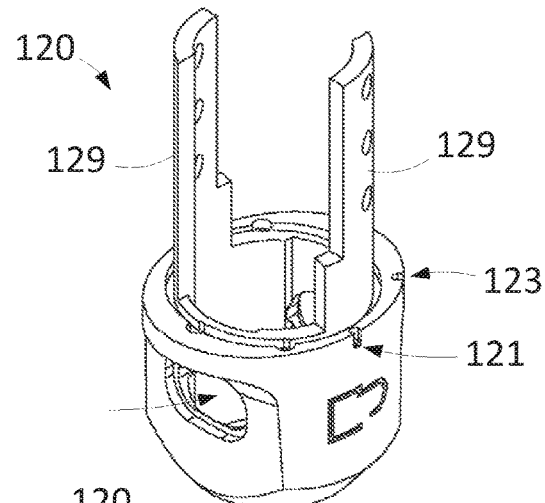
Figures 16H, 16I, 16J:
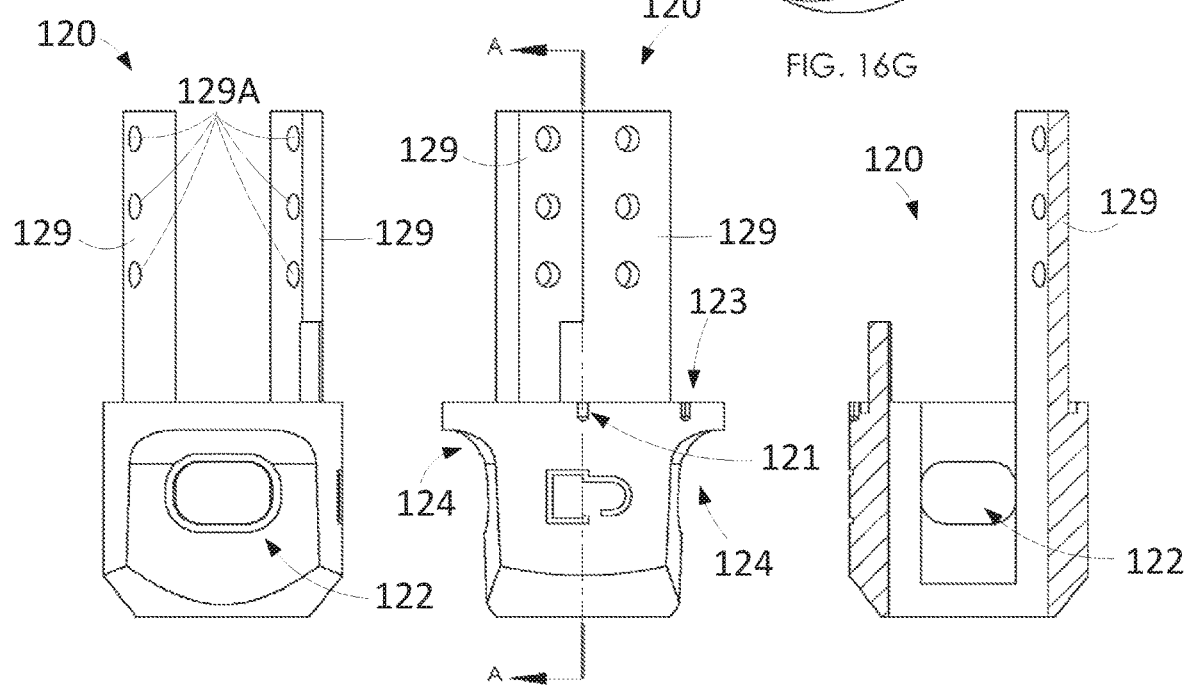
Figure 17A:
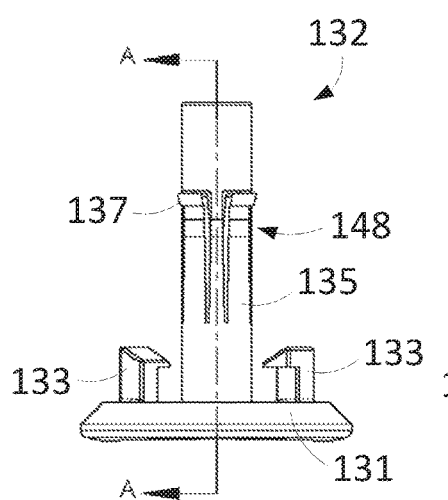
FIGS. 17A-17C are various views of the first plunger portion of the plunger assembly of the injector device of FIG. 1A.
Figure 17B:
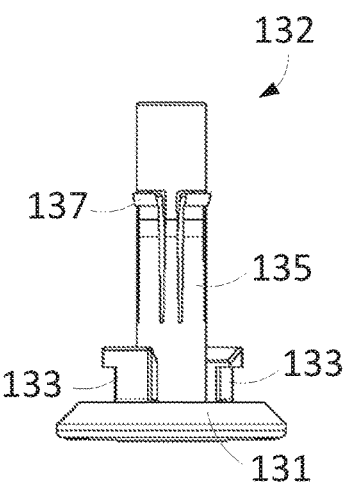
Figure 17C:
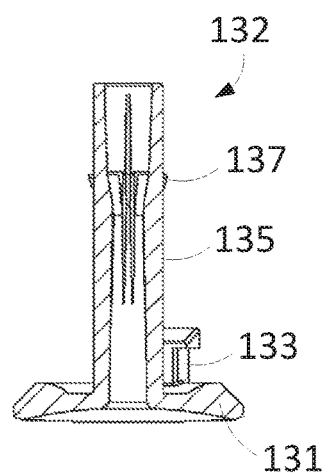

FIGS. 16F-16J are various views of the second housing portion 120. Specifically, FIG. 16F is a top view of the second housing portion 120, FIG. 16G is a perspective view of the second housing portion 120, FIG. 16H is a front view of the second housing portion 120, and FIG. 16I is a side view of the second housing portion 120. FIG. 16J is a cross-sectional view of the second housing portion 120 taken along line A-A in FIG. 16I. As shown, the second housing portion 120 includes two mating elements 129. Each mating element 129 defines three recesses 129A. Each of the recesses 129A is configured to align with and engage with a mating feature 199 of the internal cartridge 190 such that the internal cartridge 190 and the second housing portion 120 are fixed relative to each other during operation of the injector device 100. In some embodiments, the internal cartridge 190 can be coupled to the second housing portion 120 via, for example, ultrasonic welding, solvent bonding, adhesive bonding, and the like FIGS. 17A-17C are various views of the first plunger portion 132. Specifically, FIG. 17A is a front view of the first plunger portion 132 and FIG. 17B is a side view of the first plunger portion 132. FIG. 17C is a cross-sectional view of the first plunger portion 132 taken along line A-A in FIG. 17A. The first plunger portion 132 includes a pad 131 and a stem 135 extending distally from the pad 131. The first plunger portion 132 also includes two latches 133 extending distally from the distal surface of the pad 131. Additionally, the first plunger portion 132 includes four tabs 137 projecting from a sidewall of the stem 135. The tabs 137 can be biased outward from the sidewall of the stem 135 and/or from the central axis of the first plunger portion 132. The tabs 137 can also be shaped and sized such that the tabs 137 can be disposed within the guide recesses 188 of the second plunger portion 134 when the first plunger portion 132 is disposed within the second plunger portion 134. The tabs 137 can also be flexible such that when the injector device 100 is in a locked configuration and the first plunger portion 132 is disposed within the second plunger portion 134, the tabs 137 are compressed by the inner sidewall of the first plunger portion 132. When the first plunger portion 134 is translated proximally relative to the second plunger portion 132 (e.g., when the injector device 100 is in an unlocked configuration), the tabs 137 can translate within the guide recesses 188. Upon reaching the tab recesses 185, the tabs 137 can automatically transition from the compressed position to an expanded position in which the tabs 137 extend into or through the tab recesses 185. Thus, any distal translation of the first plunger portion 132 can apply a force to the second plunger portion 134 and translate the second plunger portion 134. Additionally, the first plunger portion 132 can include an indicator line 148 on the stem 135. The indicator line 148 can be, for example, green in color.

Figure 18C:
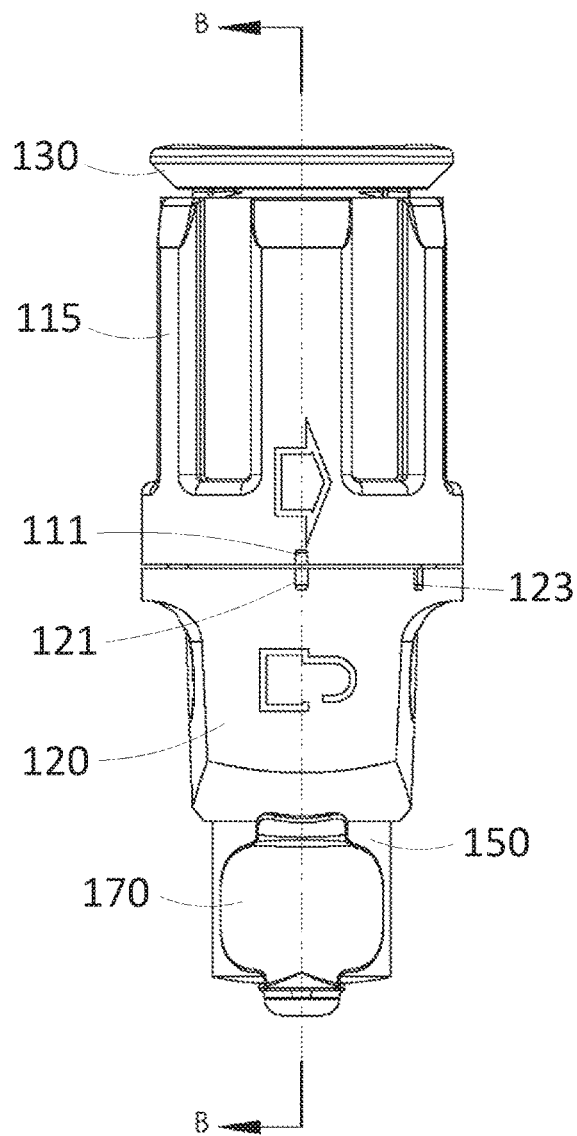
Figure 18D:
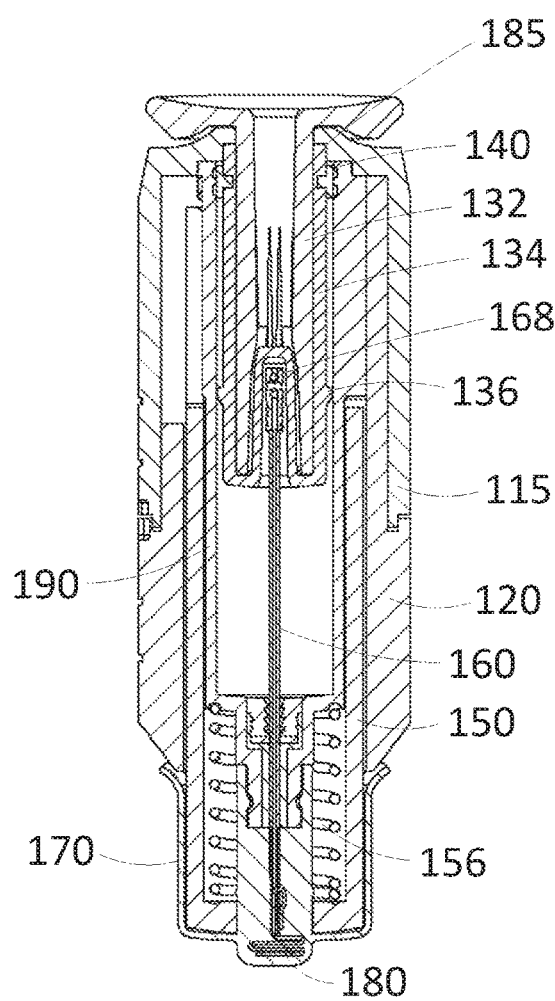
Figure 18E:
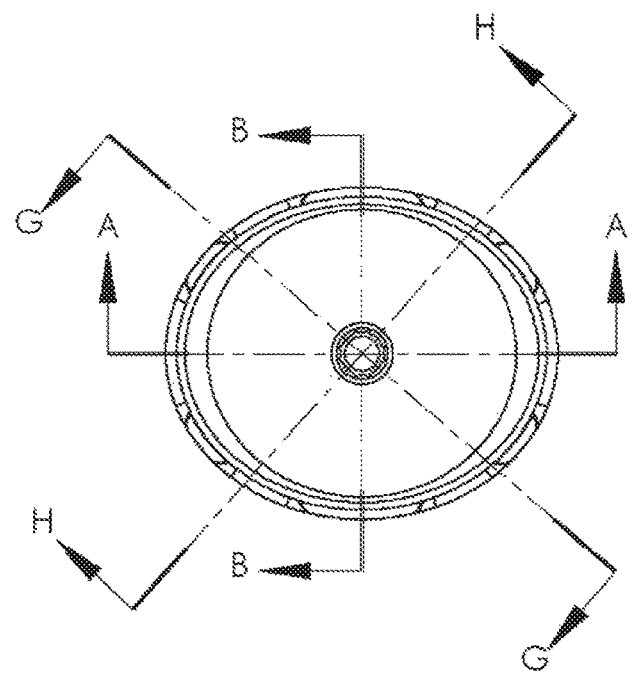
Figure 18F:
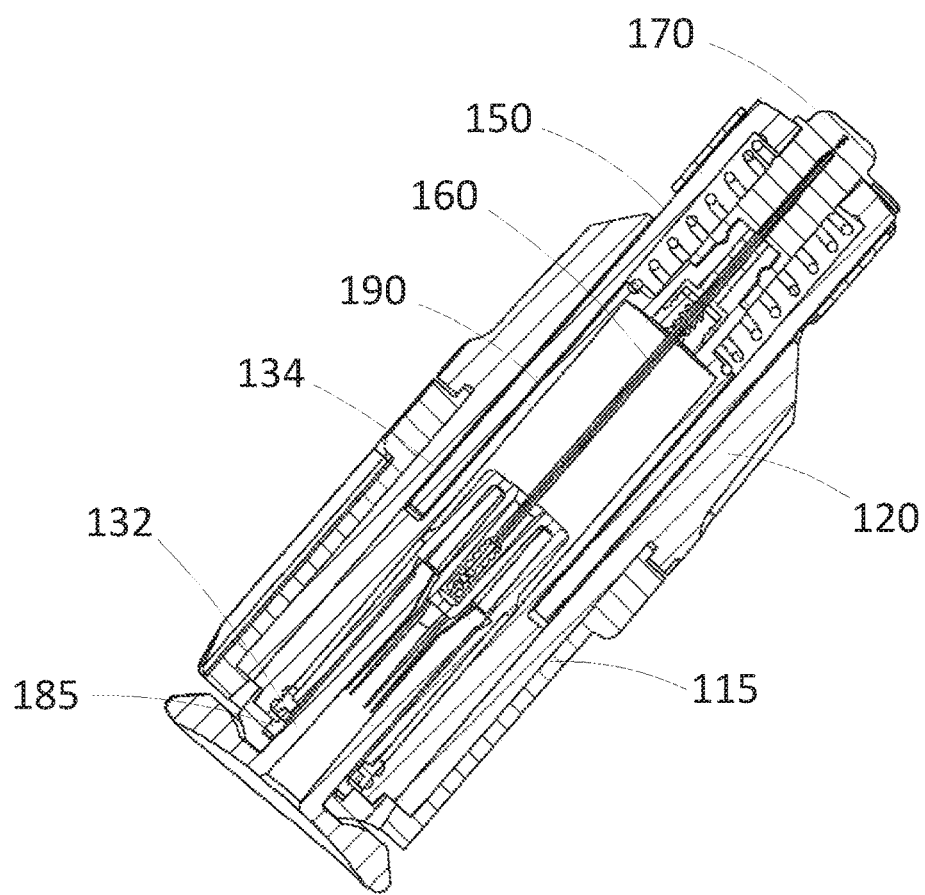
Figure 18G:
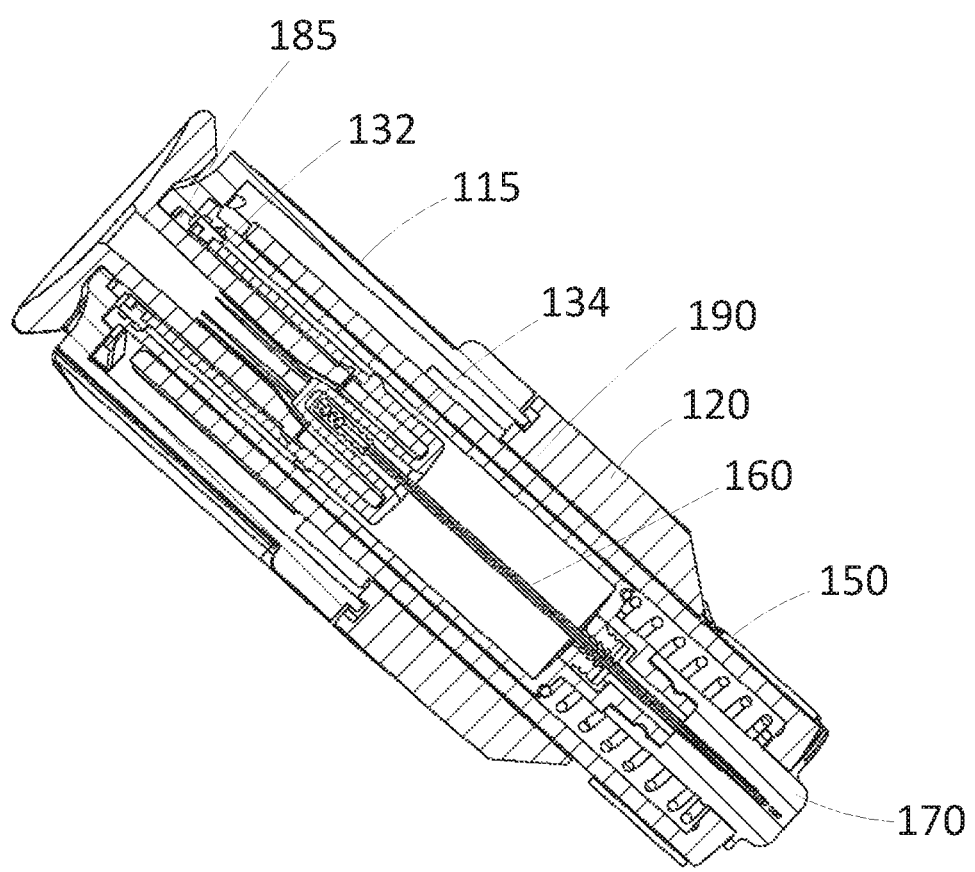

FIGS. 18A-18G are various views of the injector device 100 in the first, locked configuration. Specifically, FIG. 18A is a front view of the injector device 100 in the first, locked configuration. FIG. 18B is a cross-sectional view taken along line A-A of FIG. 18A. FIG. 18C is a side view of the injector device 100 in the first, locked configuration. FIG. 18D is a cross-sectional view taken along line B-B of FIG. 18C. FIG. 18E is a top view of the injector device 100 of FIG. 18C. FIG. 18F is a cross-sectional view of the injector device 100 taken along line G-G of FIG. 18E. FIG. 18G is a cross-sectional view of the injector device 100 taken along line H-H of FIG. 18E. In some embodiments, the length of the injector device 100 in the first, locked configuration (e.g., from the proximal surface of the first plunger portion 132 to the distal surface of the cover 170) can be equal to or less than about 3 inches.

As shown in FIG. 18C and described above with reference to FIGS. 1A-IC, the positional indicator notch 111 is aligned with the closed indicator notch 121 when the injector device 100 is in the first, locked configuration. The reservoir 192 is defined by the guide seal 193, the internal cartridge 190, the sealing element 140, and the second plunger portion 134. As shown in FIG. 18B, the reservoir 192 can include a cylindrical gap portion 141 between the sidewall 138 of the second plunger portion 134 and an inner surface of the internal cartridge 190. The reservoir 192 also includes the interior cavity 198 defined by the internal compartment 187 of the second plunger portion 134. The recesses 188 of the guiding feature 136 (shown in FIG. 14D), provide pathways for fluid transfer between the cylindrical gap portion 141 and the portion of the reservoir 192 distal of the distal end wall 139 of the second plunger portion 134. Said another way, the cylindrical gap portion 141 is in fluid communication with a portion of the reservoir 192 distal of the second plunger portion 134. In the first, locked configuration of the injection device 100, the needle 160 is in an initial position relative to the catch feature 195 such that the first end 165 of the needle 160 is disposed within the interior cavity 198 defined by the internal compartment 187 of the second plunger portion 134. Thus, the first end 165 of the needle 160 is disposed within the reservoir 192, with the lumen 162 of the needle 160 in fluid communication with the reservoir 192, when the injector device 100 is in the first, locked configuration.

Additionally, as can be seen in FIG. 18B, although the spring 156 is compressed between the distal end wall of the needle sheath 150 and the distal end wall of the internal cartridge 190, the needle sheath is prevented from extending distally relative to the housing assembly 110 due to the abutment between the projecting portions 154 of the needle sheath 150 and the retaining portions 114 of the first housing portion 115. Additionally, the proximal retaining tab 118 (shown in FIG. 16B) is engaged with the latch 133 of the first plunger portion 132 such that the latch 133, and thus the first plunger portion 132, is prevented from being translated proximally relative to the housing assembly 110.

Figure 19C:
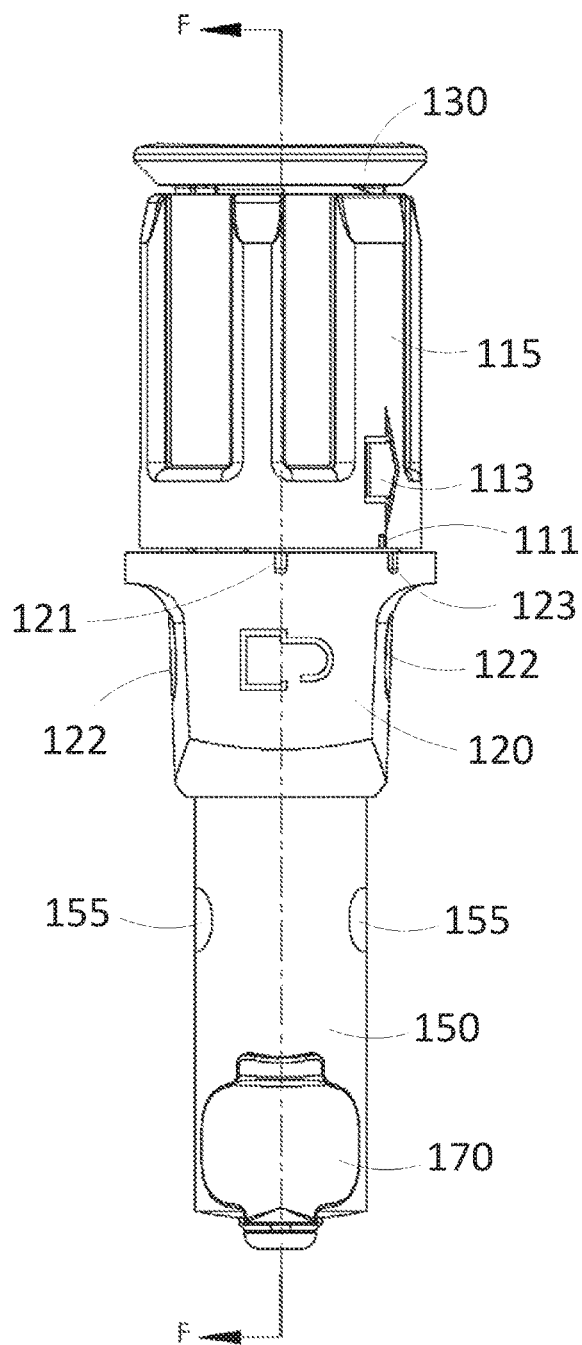
Figure 19D:
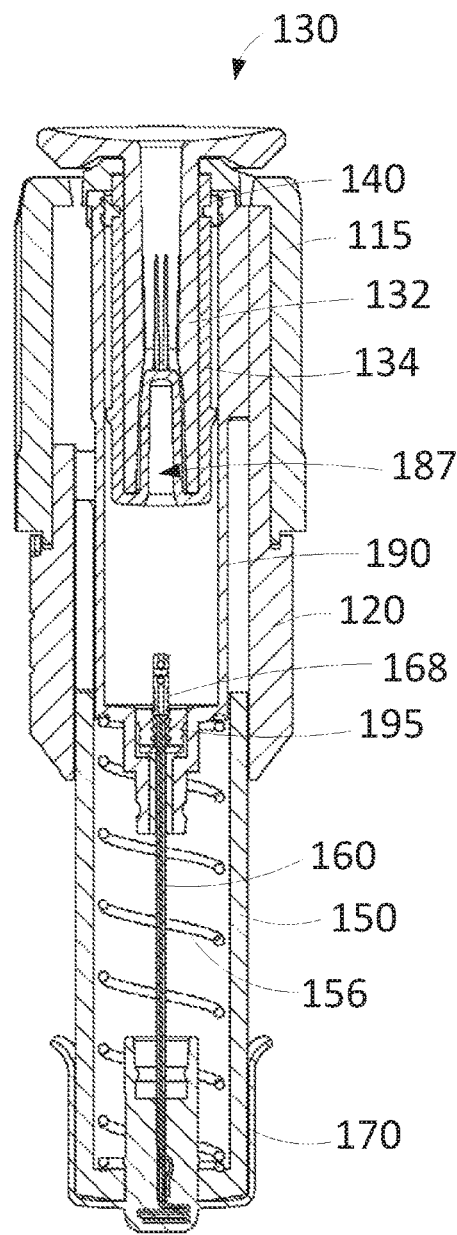
Figure 19E:
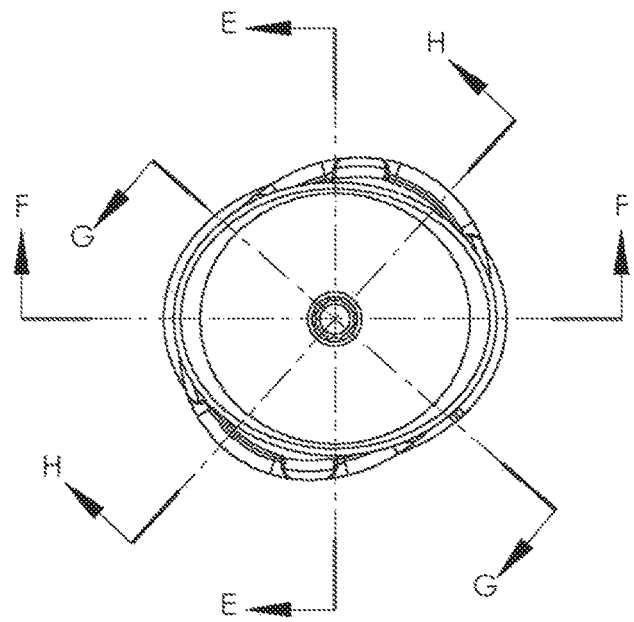
Figure 19F:
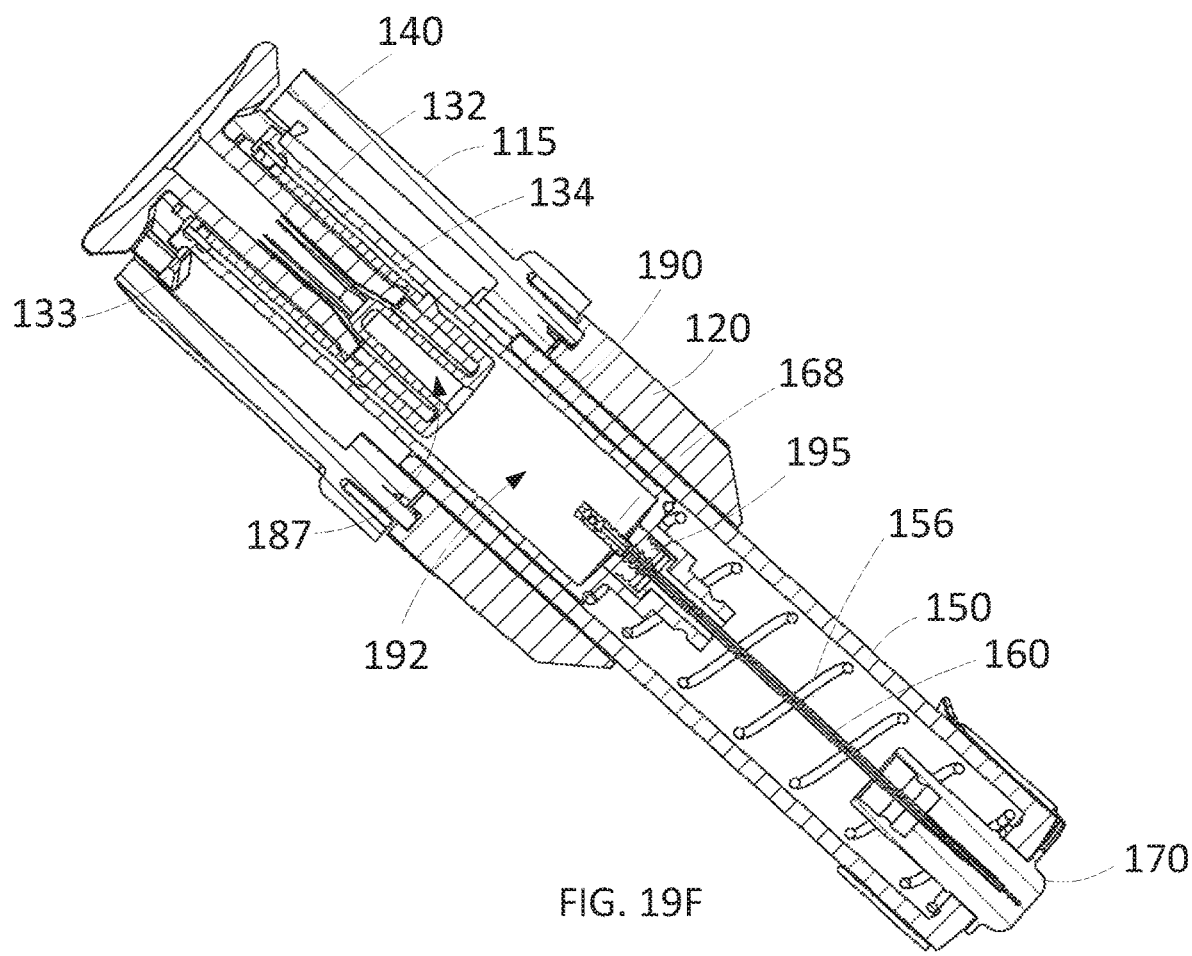
Figure 19G:
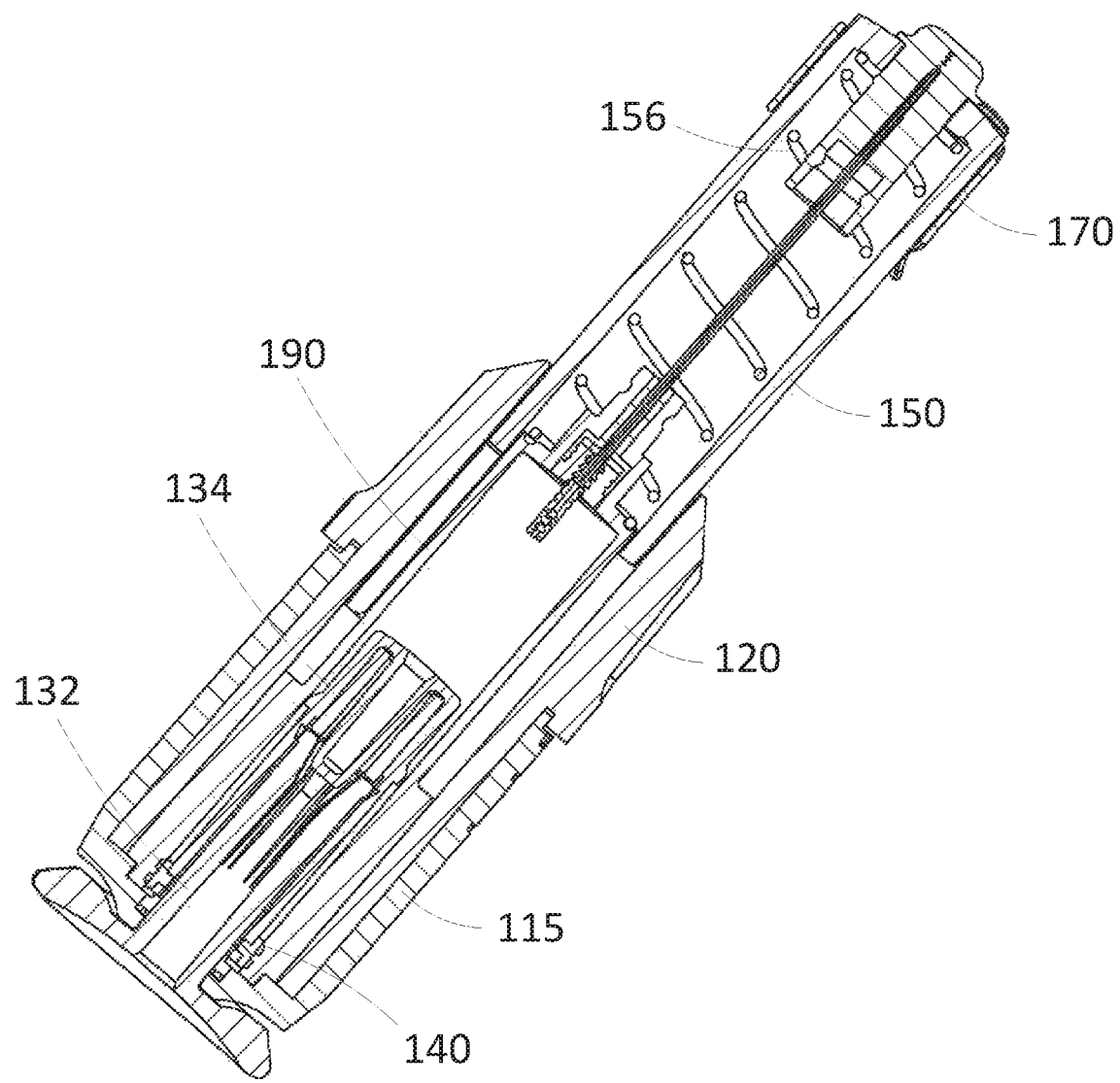

FIGS. 19A-19G are various views of the injector device 100 in the second, unlocked configuration. Specifically, FIG. 19A is a front view of the injector device 100 in the second, unlocked configuration and FIG. 19B is a cross-sectional view of the injector device 100 taken along line E-E of FIG. 19A. FIG. 19C is a side view of the injector device 100 in the second, unlocked configuration and FIG. 19D is a cross-sectional view of the injector device 100 taken along line F-F of FIG. 19C. FIG. 19E is a top view of the injector device 100 of FIG. 19C. FIG. 19F is a cross-sectional view of the injector device 100 taken along line H-H of FIG. 19E. FIG. 19G is a cross-sectional view of the injector device 100 taken along line G-G of FIG. 19E.

To transition the injector device 100 from the first, locked configuration to the second, unlocked configuration, the first housing portion 115 can be rotated relative to the second housing portion 120. As shown in FIG. 19C and described above with reference to FIGS. 1A-1C, the positional indicator notch 111 is aligned with the open indicator notch 123 when the injector device 100 is in the second, unlocked configuration. The rotation of the first housing portion 115 relative to the second housing portion 120 rotates the retaining portions 114 of the first housing portion 115 out of alignment with the projecting portions 154 of the needle sheath 150. Thus, under the force of the spring 156, the needle sheath 150 can be distally translated relative to the housing assembly 110. Said another way, with the retaining portions 114 no longer obstructing the projecting portions 154 of the first housing portion 115 from distal movement relative to the housing assembly 110, the projecting portions 154 (and thus, the entire needle sheath 150) can be translated distally by the spring 156.

The distal translation of the needle sheath 150 by the spring 156 also distally translates the cover 170 coupled to the distal end of the needle sheath 150. Due to the cover 170 being coupled to the needle 160 via the needle pull barb 180, the distal translation of the cover 170 by the needle sheath 150 also distally translates the needle 160 from the initial position relative to the catch feature 195 to an intermediate position in which the engagement portion 168 of the needle 160 is coupled to the catch feature 195, as shown, for example, in FIG. 19B. In some embodiments, the engagement portion 168 of the needle 160 can be in contact with the catch feature 195 in the intermediate position. In some embodiments, the engagement portion 168 of the needle 160 can be engaged with one or more barbs 197 of the catch feature 195 in the intermediate position.

Additionally, the rotation of the first housing portion 115 relative to the second housing portion 120 rotates the slots 119 and proximal retaining tabs 118 of the first housing portion 115 relative to the latching feature 133 of the first plunger portion 132. Thus, when the injector device 100 is in the second, unlocked configuration, the latching feature 133 is aligned with the slots 119 of the first housing portion 115 and unobstructed from proximal translation by the proximal retaining tabs 118.

Figures 20C, 20D:
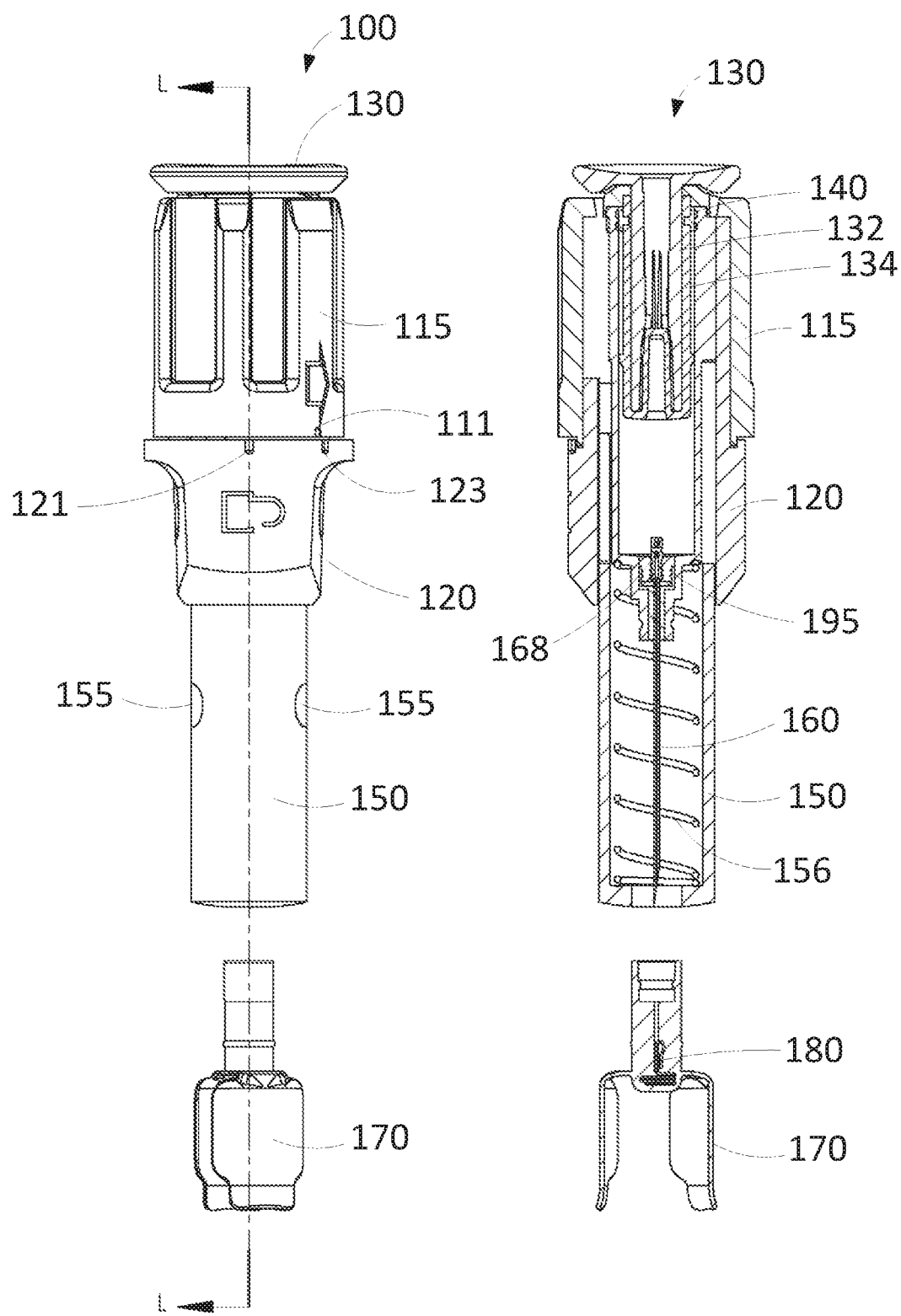
Figure 20G:
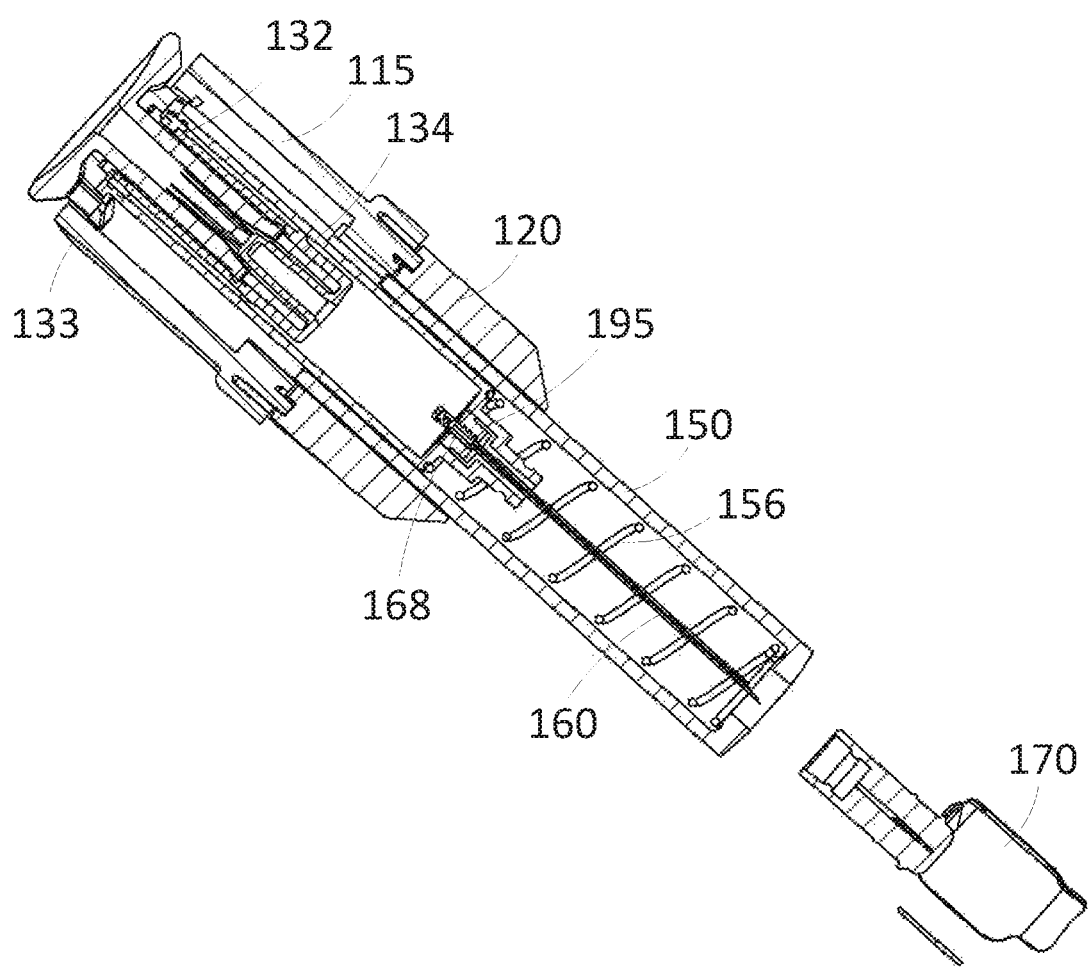

FIGS. 20A-20G are various views of the injector device 100 in a third, uncovered configuration. Specifically, FIG. 20A is a front view of the injector device 100 in the third, uncovered configuration and FIG. 20B is a cross-sectional view of the injector device 100 taken along line A-A in FIG. 20A. FIG. 20C is a side view of the injector device 100 in the third, uncovered configuration and FIG. 20D is a cross-sectional view of the injector device 100 taken along line L-L in FIG. 20C. FIG. 20E is a top view of the injector device 100 of FIG. 20C. FIG. 20F is a cross-sectional view of the injector device 100 taken along line M-M in FIG. 20E. FIG. 20G is a cross-sectional view of the injector device 100 taken along line N-N in FIG. 20E.

The injector device 100 can be transitioned from the second, unlocked configuration to the third, uncovered configuration by removing the cover 170. As shown in FIG. 20A, for example, the cover 170 can be transitioned to the detached configuration by, for example, rotating the tabs 172 and pulling the tabs 172 distally in the direction of arrow Z-Z away from the needle sheath 150.

Due to the coupling of the cover 170 to the needle second end 163 of the needle 160, the removal of the cover 170 from the needle sheath 150 and the second end 163 of the needle 160 translates the needle 160 distally from the intermediate position to an engaged position in which the engagement feature 168 of the needle 160 is fully engaged with the catch feature 195. Specifically, the engagement feature 168 is engaged with the barbs 197 of the catch feature 195. As shown in FIG. 20B, for example, the first end 165 of the needle 160 is disposed within the reservoir 192 such that the lumen 162 of the needle 160 is in fluid communication with the reservoir 192 when the needle 160 is in the engaged position and the injector device 100 is in the third, uncovered configuration.

Figure 21A:
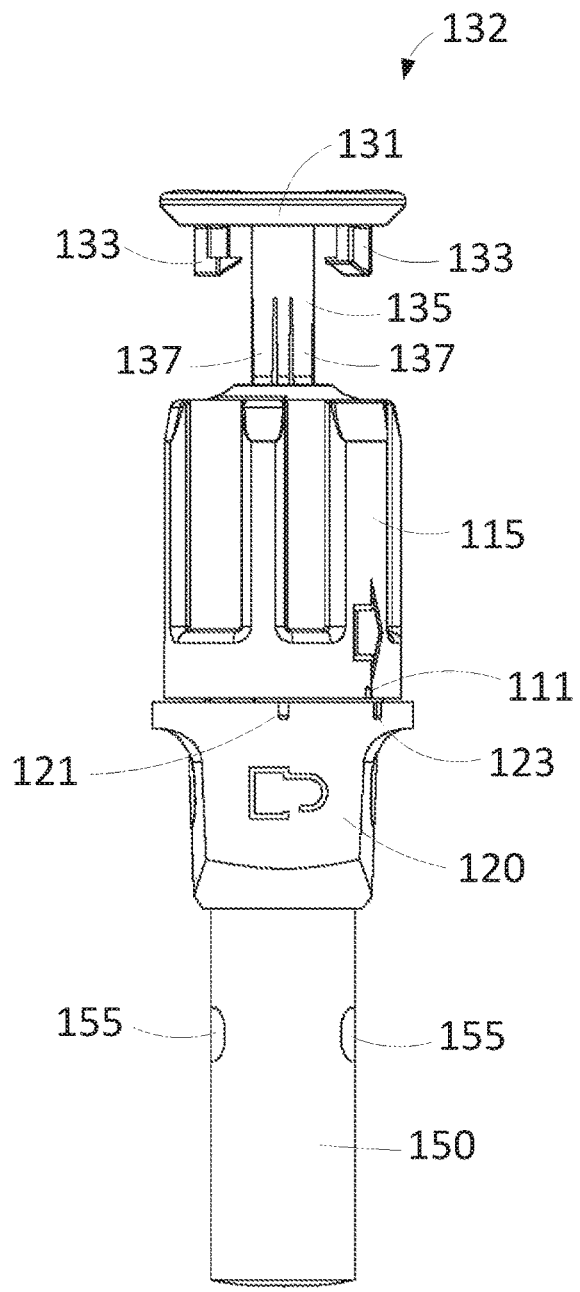
Figure 21B:
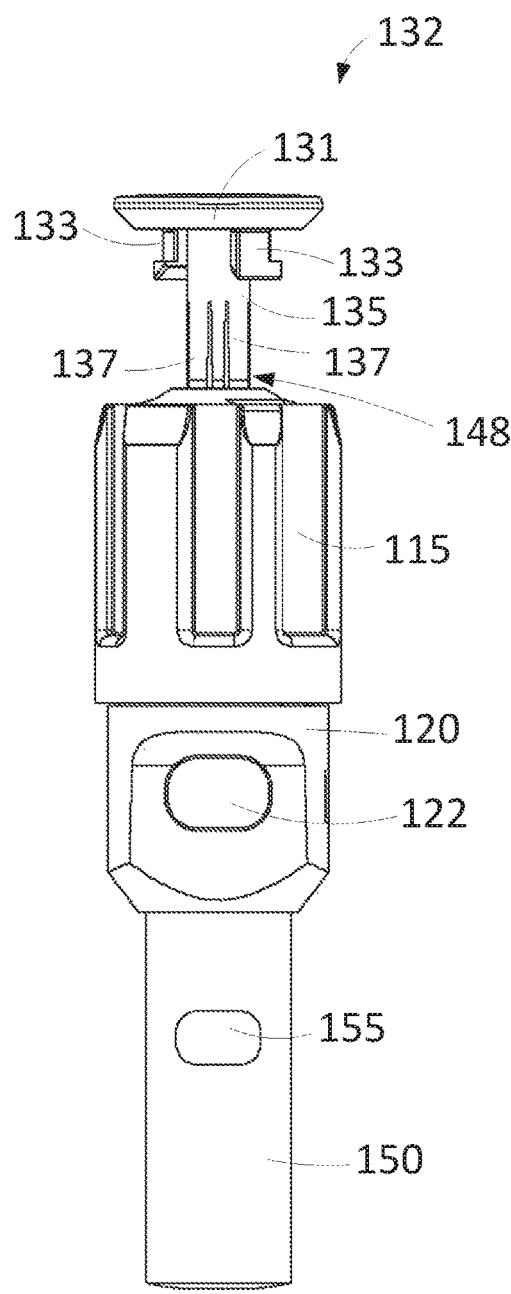
Figure 21C:
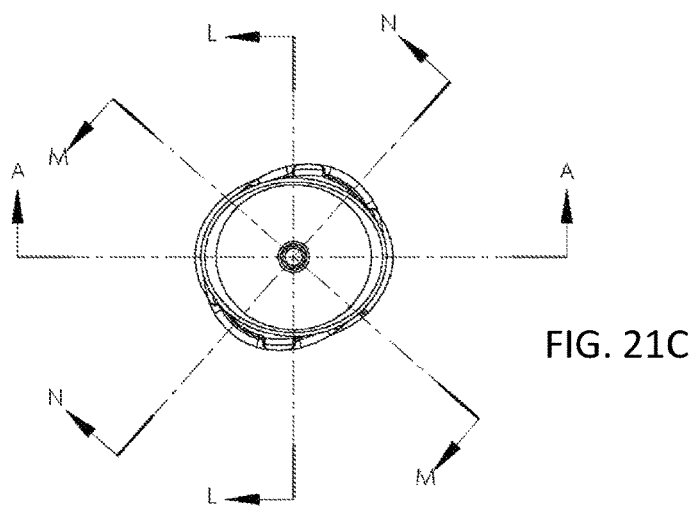
Figure 21D:
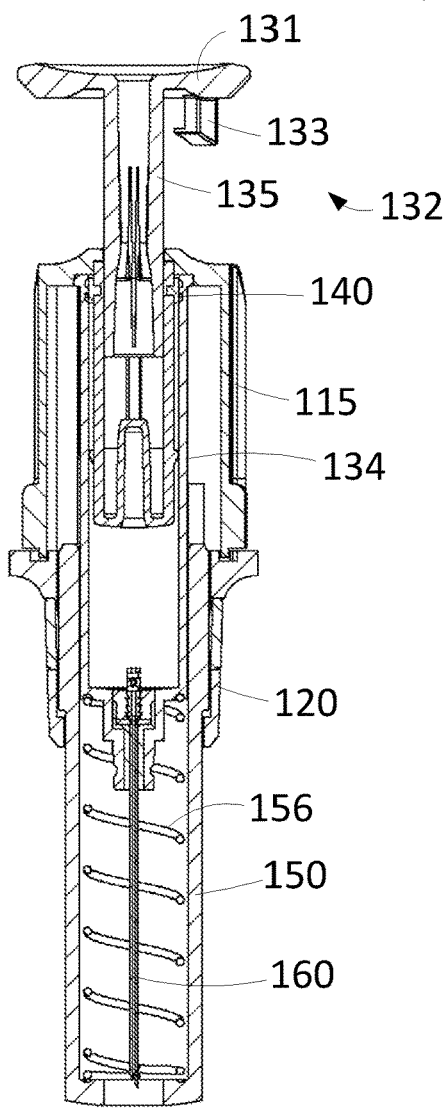
Figure 21E:
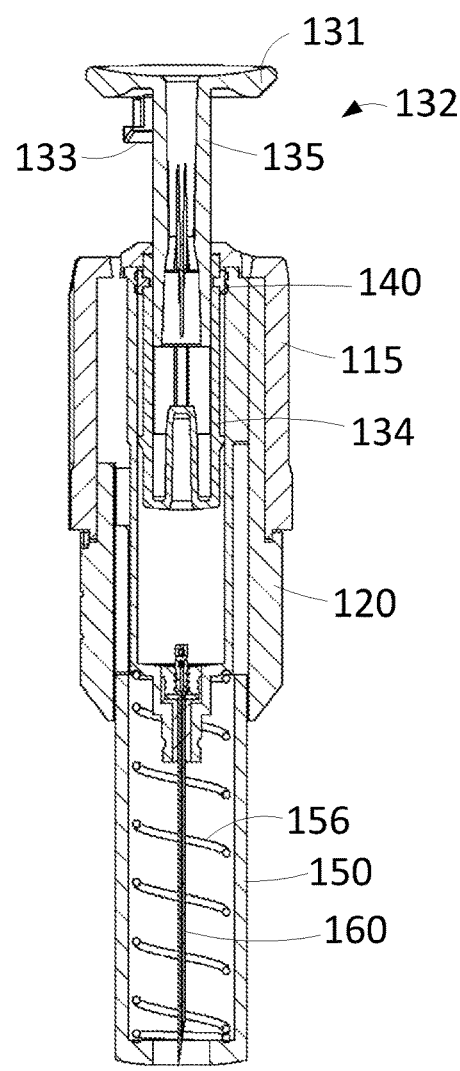

FIGS. 21A-21G are various views of the injector device 100 in a fourth, extended or "ready" configuration. Specifically, FIGS. 21A and 21B are a side view and a back view, respectively, of the injector device 100 in the fourth, extended configuration. FIG. 21C is a top view of the injector device 100 as shown in FIG. 21A. FIG. 21D is a cross-sectional view of the injector device 100 taken along line A-A of FIG. 21C. FIG. 21E is a cross-sectional view of the injector device 100 taken along line L-L of FIG. 21C. FIG. 21F is a cross-sectional view of the injector device 100 taken along line N-N of FIG. 21C. FIG. 21G is a cross-sectional view of the injector device 100 taken along line M-M of FIG. 21C.

To transition the injector device 100 from the third, uncovered configuration to the fourth, extended configuration, the first plunger portion 132 can be proximally translated relative to the housing assembly 110. As described above, the transition of the first housing portion 115 between the first, locked configuration and the second, locked configuration rotates the proximal retaining tabs 118 out of obstructing alignment with the latching features 133 of the first plunger portion 132. Thus, the first plunger portion 132 can be proximally translated (e.g., via pulling on the pad 131) relative to the second plunger portion 132 and the housing assembly 110. As the first plunger portion 132 is proximally translated, the tabs 137 extending from the stem 135 of the first plunger portion 132 can slide within the guide recesses 188 of the second plunger portion 134 until the tabs 137 reach the tab recesses 185 of the second plunger portion 134. Upon reaching the tab recesses 185, the tabs 137 can transition from the compressed position to the expanded position, moving into or through the tab recesses 185. In such a configuration, the injector device 100 is ready to be disposed on the skin of the user for the injection process. In some embodiments, visibility of the indicator line 148 on the stem 135 of the first plunger portion 132 proximal of the first housing portion 115 and/or an auditory and/or tactile snap can indicate that the first plunger portion 132 has been sufficiently proximally translated relative to the housing assembly 110. The indicator line 148 may be a green region with the same color as the window 122, to indicate when the device is ready for use.

Figure 22A:
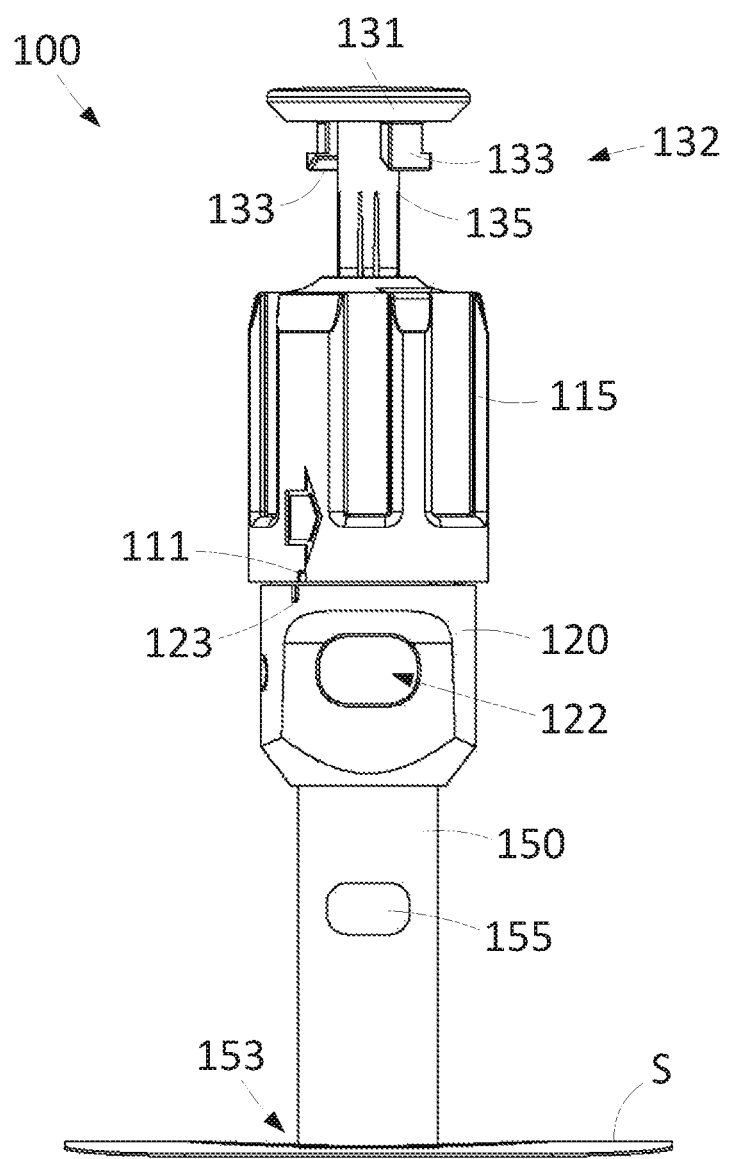
Figure 22B:
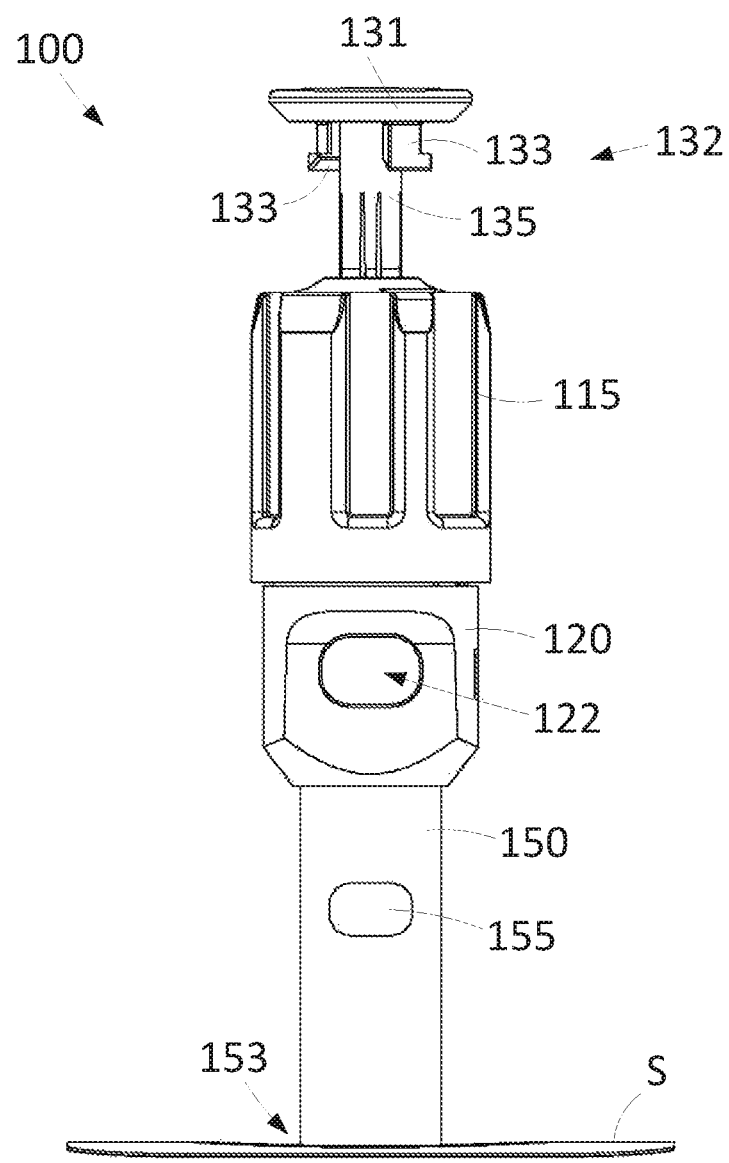

FIGS. 22A-22D are various views of the injector device 100 disposed on a skin S (e.g., skin on the arm or the leg) of a user prior to penetration. Specifically, FIGS. 22A, 22B, and 22C are a front view, a back view, and a side view, respectively, of the injector device 100 in the fourth, extended or ready configuration disposed on the skin S of a user. FIG. 22D is a cross-sectional view of the injector device 100 taken along line T-T of FIG. 22C. As shown, once the first plunger portion 132 has been withdrawn proximally relative to the housing assembly 110 such that the tabs 137 are engaged with the tab recesses 185 of the second plunger portion 134, the injector device 100 is ready for injection. Specifically, the injector device 150 can be aligned with the skin S such that the needle 160 is substantially perpendicular to the skin S. The spring 156 within the needle sheath 150 can maintain the distal end 153 of the needle sheath 150 against the skin S of the patient during the penetration and injection process. By providing a skin-facing surface area at the distal end 153 of the needle sheath 105, the needle sheath 150 in combination with the spring 156 can also assist the user in aligning the needle 160 with the skin S such that the needle 160 is substantially perpendicular to the skin S. Furthermore, the needle sheath 150 can obstruct the view of the needle 160 by the user, reducing stress and/or anxiety associated with the sight of the needle 160.

FIGS. 23A-23D are various views of the injector device 100 in a fifth configuration in which the needle 160 has penetrated the skin S of the user. Specifically, FIG. 23A is a front view of the injector device 100 in a penetration configuration. FIG. 23B is a cross-sectional view taken along line U-U of FIG. 23A. FIG. 23C is a side view of the injector device 100 in a penetration configuration. FIG. 23D is a cross-sectional view taken along line V-V of FIG. 23C.

The injector device 100 can be transitioned from the fourth, extended configuration to the fifth, penetration configuration by distally translating the housing assembly 110 against the force of the spring 156 relative to the needle sheath 150 (i.e., toward the skin S). Due to the internal cartridge 190 being fixedly coupled to the second housing portion 120 via the mating features 199, distal movement of the housing assembly 110 distally translates the internal cartridge 190. Additionally, due to the engagement between the engagement portion 168 of the needle 160 and the barbs 197 of the catch feature 195, distal translation of the internal cartridge 190 toward the skin S distally translates the needle 160 through the skin S.

Figure 24D:
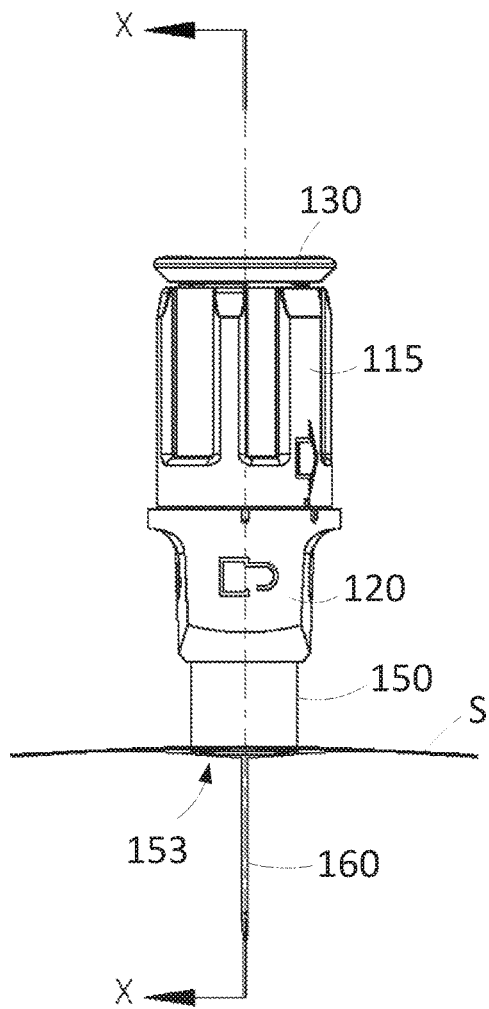
Figure 24E:
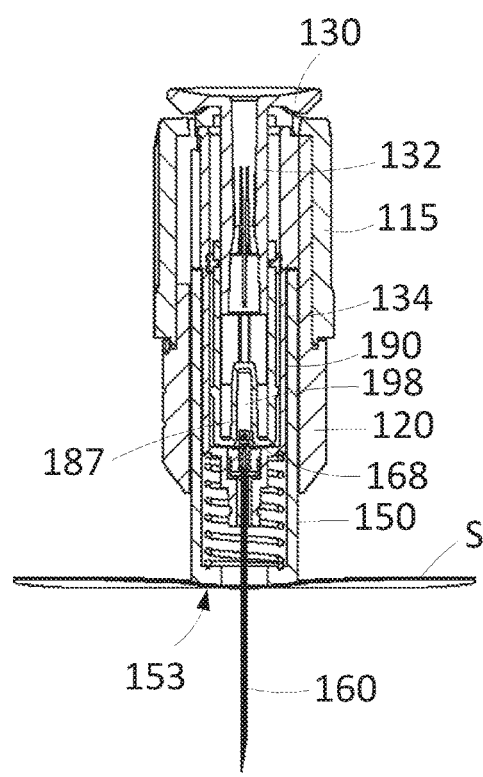

FIGS. 24A-24E are various views of the injector device 100 in a sixth configuration in which the medicament has been injected from the reservoir 192 into the user. Specifically, FIG. 24A is a back view of the injector device 100 in the sixth configuration and FIG. 24B is a front view of the injector device 100 in the sixth configuration. FIG. 24C is a cross-sectional view of the injector device 100 taken along line W-W of FIG. 24B. FIG. 24D is a side view of the injector device 100 in the sixth configuration. FIG. 24E is a cross-sectional view of the injector device 100 taken along line X-X of FIG. 24D.

The injector device 100 can be transitioned from the fifth, penetration configuration to the sixth, injection configuration by distally translating the first plunger portion 132 relative to the housing assembly 110 such that the first plunger portion 132 distally translates the second plunger portion 134. The distal translation of the second plunger portion 134 can push fluid within the reservoir 192 into the inlets 164 of the needle 160 such that the fluid flows through the lumen 162 of the needle, from the outlet 166 of the needle 160, and into the user (e.g., into the surrounding tissue).

The first plunger portion 132 can be distally translated relative to the housing assembly 110, for example, by the user pressing on the pad 131 of the first plunger portion 132 with a finger (e.g., a thumb). The user can use any suitable grip to hold the injector device during the penetration and injection process. In some embodiments, the user can place a finger in engagement on opposing sides of the second housing portion 120 (e.g., in the regions of recesses 124) and a thumb on proximal surface of the pad 131 to press the first plunger portion 132 distally toward the skin of the user. In some embodiments, the user can wrap four fingers of the user's hand around the housing assembly 110 of the injector device 100, and can press the pad 131 of the first plunger portion 132 distally toward the skin of the user with the user's thumb.

Figure 25C:
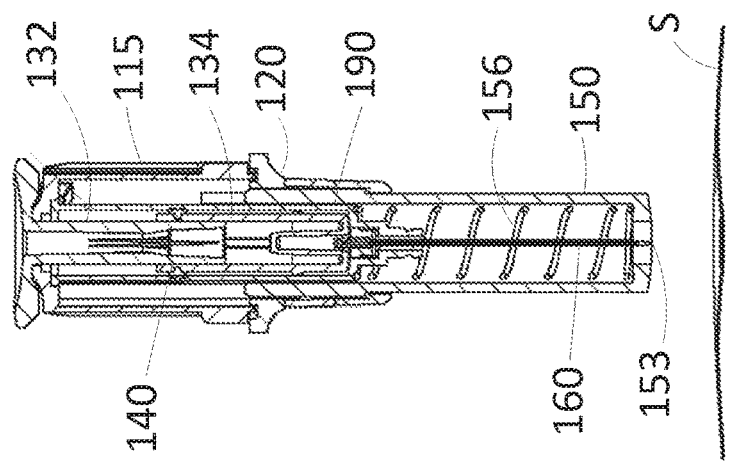
Figure 25B:
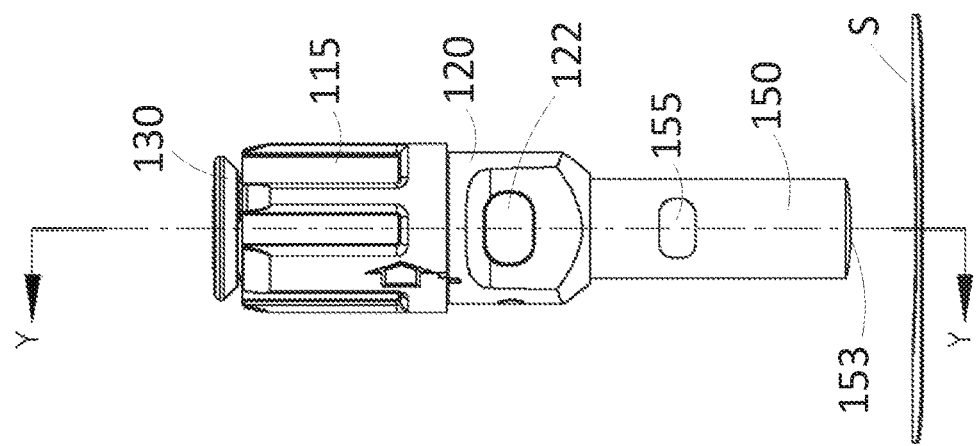
Figure 25A:
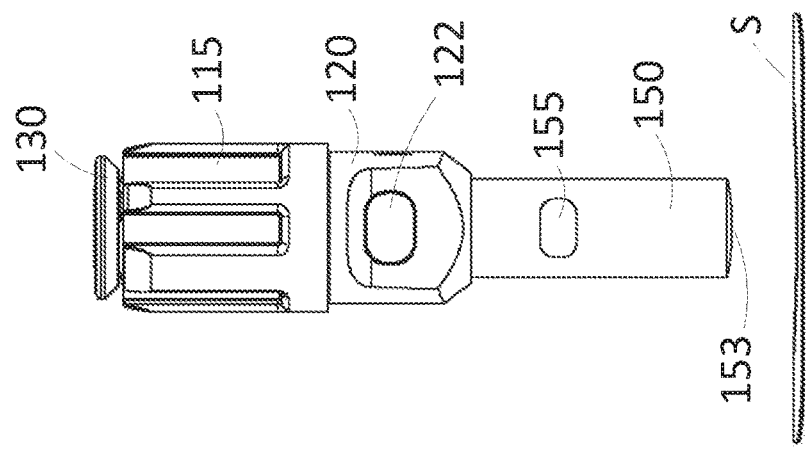

FIG. 25A-25E are various views of the injector device 100 in a seventh configuration in which the needle 160 has been withdrawn and the injector device 100 has been separated from the user. Specifically, FIGS. 25A and 25B are a back view and a front view, respectively, of the injector device 100 in the seventh configuration. FIG. 25C is a cross-sectional view of the injector device 100 taken along line Y-Y of FIG. 25B. FIG. 25D is a side view of the injector deice 100 in the seventh configuration. FIG. 25E is a cross-sectional view of the injector device 100 taken along line Z-Z of FIG. 25D.

As shown in FIG. 25A, for example, after injection of the fluid in the reservoir 192 through the needle 160, the injector device 100 can be removed from the skin S of the user by proximally translating the injector device 100 relative to the skin S. As the needle 160 is withdrawn from the skin S, the spring 156 can apply a force to the distal end wall of the needle sheath 150 such that the needle sheath 150 automatically extends to cover the portion of the needle 160 which has been withdrawn from the skin S. After the needle 160 has been fully withdrawn from the skin S, the needle sheath 150 can be fully extended to cover the needle 160, including the sharp tip on the second end 163 of the needle 160. Thus, accidental needle sticks may be reduced. In some embodiments, the injector device 100 can be locked after injection and withdrawal such that the needle sheath 150 is restrained from being moved relative to the housing assembly 110. For example, the first housing portion 115 can be rotated relative to the second housing portion 120 such that the positional indicator notch 111 aligns with the closed indicator notch 121. In such a position, a portion of the first housing portion 115 (e.g., a distal surface of the inwardly projecting retaining portions 114) can engage with and/or obstruct the needle sheath 150 (e.g., the outwardly projecting portion 154) from moving proximally relative to the needle 160 and the housing assembly 110. The injector device 100 can be disposed of via any suitable method.

The cover 170 of the device may be comprised of an injection molded medical grade silicone. This silicone may have a relative density of Shore A hardness of about 60, or in the range of about 50 to 70 around the area where the needle is bonded and made sterile. The needle pull barb 180 of the injector may be molded in place, embedded in the cover. This needle pull barb 180 may comprise formed stainless steel wire or a Polyethylene fiber that is co-molded, in place. The needle sheath 150 may be injection molded from a medical grade high-density polyethylene (HDPE). The return spring for the needle sheath 156 may be made from a tempered stainless steel with approximate diameter of 0.03", or about 0.01" to about 0.5", with 6 to 7 revolutions, or in a range of 3 to 10 revolutions, for example. The clear windows 122 may be molded from a clear ABS and the first and second housings, 120 and 115, respectively, of the device may be injection molded from high strength ABS or a polycarbonate polymer, for example. The internal cartridge 190 of the device is to be injection molded from a colorless Cyclo-olefin Polymer (COP) Zeonex 420 or Zeonor 1020R, or comprise a glass container. The guide bushing 191 may be precision machined from brass or molded from a medical grade high-density polyethylene. The rubber seal for the injection needle 193 may be precision molded from a medical grade silicone. The needle catch feature 195 may be to be molded from a medical grade high density polyethylene or machined from a medical grade nylon. The outer second plunger portion 134 of the device may be injection molded from a colorless Cyclo-olefin Polymer (COP) Zeonex 420 or Zeonor 1020R. The inner plunger 132 is to be injection molded with ABS. The rubber seal 140 is comprised of an injection molded medical grade silicone. The injection needle 160 is a precision rolled and machined stainless steel component.

Figure 26:
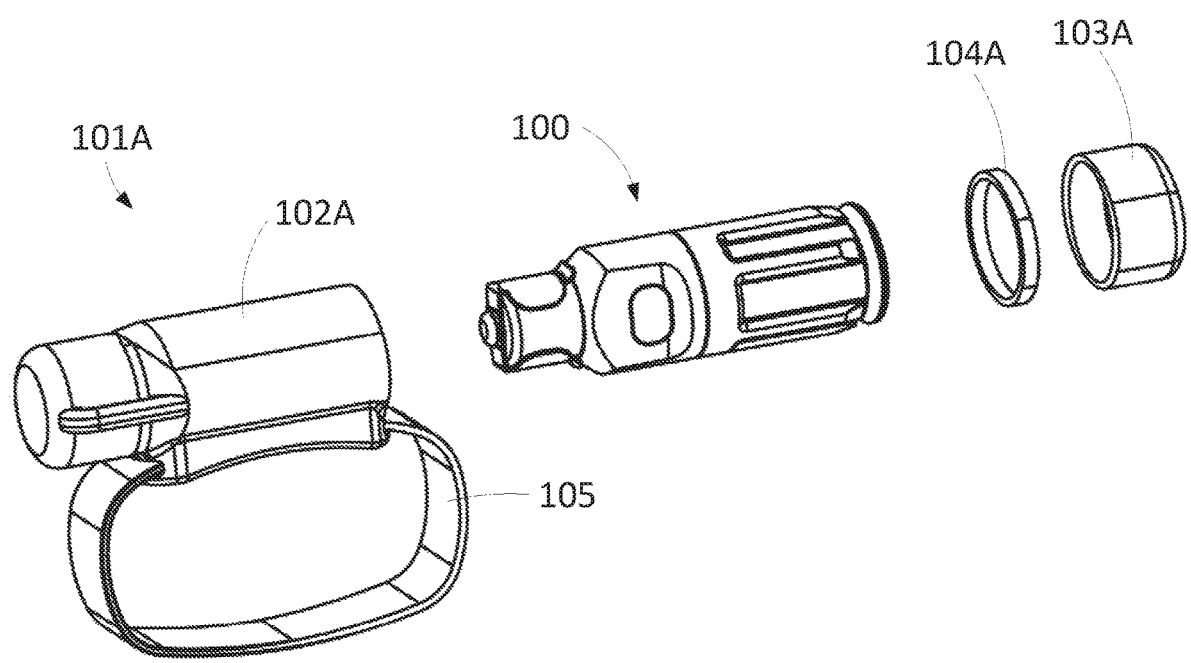
FIG. 26 is an exploded view of the injector device of FIG. 1A included in a wearable injector assembly, according to an embodiment.

As shown in FIG. 26, the injector device 100 can be included in a wearable injector assembly. The wearable injector assembly can include a casing 101A. The casing 101A can include a first casing portion 102A and second casing portion 103A. The casing 101A can also include a seal 104A. The injector device 100 can be inserted into the first casing portion 102A. The second casing portion 103A can be coupled to the first casing portion 102A via any suitable coupling mechanism, such as via internal mating threads. The seal 104A can be disposed between the first casing portion 102A and the second casing portion 103A such that the first casing portion 102A and the second casing portion 103A are sealingly coupled to protect the injector device 100. As shown, the first casing portion 102A can be coupled to a band 105. The band 105 can be shaped and sized such that the band 105 can be worn on the wrist of a user as a bracelet. Alternatively, the band 105 can be shaped and sized to be worn on any suitable part of the user's body, such as an ankle. In some embodiments, the band 105 can be shaped and sized to be coupled to a belt loop of a user's pants. Although not shown, the band 105 can include a fastening mechanism (e.g., hook and loop, a buckle) configured to couple a first portion of the band 105 to a second portion of the band such that the band 105 can be easily coupled to the user's body (e.g., a wrist).

Figure 27:
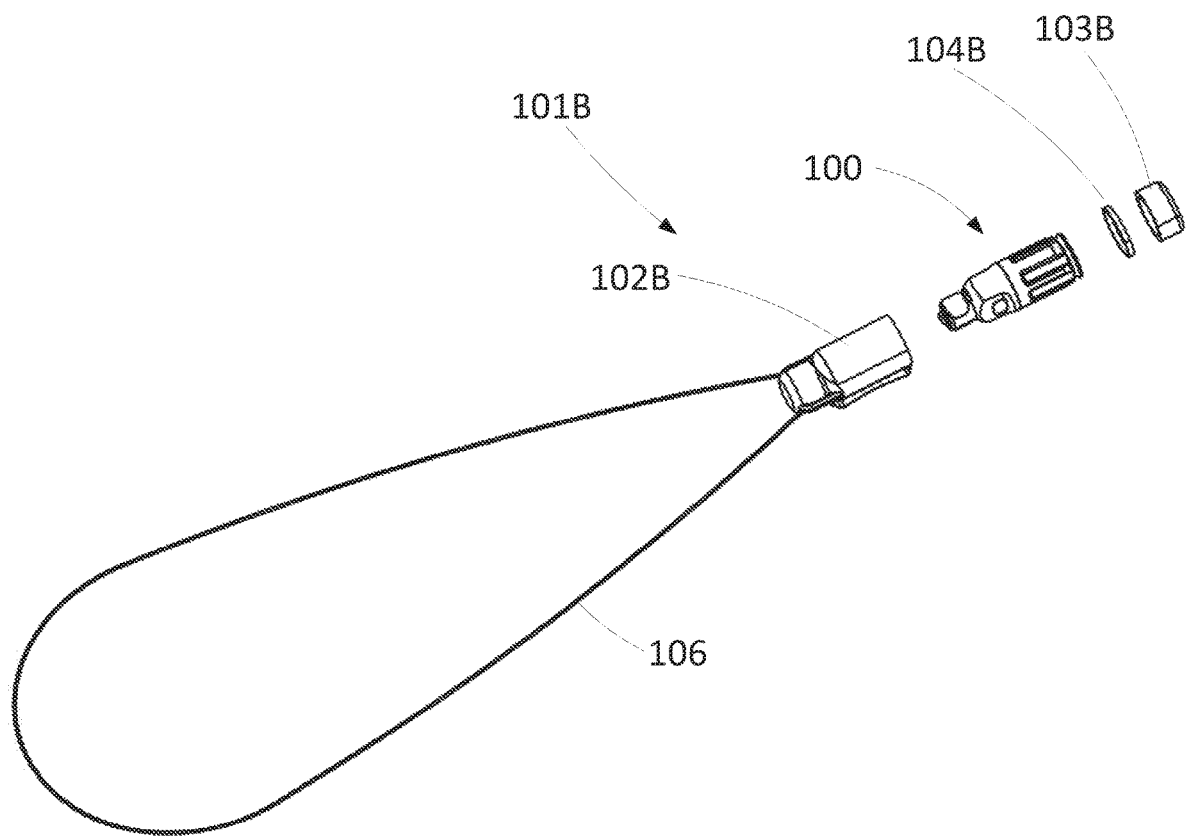
FIG. 27 is an exploded view of the injector device of FIG. 1A included in a wearable injector assembly, according to an embodiment.

As shown in FIG. 27, the injector device 100 can be included in a wearable injector assembly including an extended loop. The wearable injector assembly can include a casing 101B. The casing 101B can include a first casing portion 102B and second casing portion 103B. The casing 101B can also include a seal 104B. The injector device 100 can be inserted into the first casing portion 102B. The second casing portion 103B can be coupled to the first casing portion 102B via any suitable coupling mechanism, such as via internal mating threads. The seal 104B can be disposed between the first casing portion 102B and the second casing portion 103B such that the first casing portion 102B and the second casing portion 103B are sealingly coupled to protect the injector device 100. As shown, the first casing portion 102B can be coupled to a loop 106. The loop 106 can be shaped and sized such that the loop 106 and the casing 101B (containing the injector device 100) can be worn as a necklace.

While various embodiments have been described above, it should be understood that they have been presented by way of example only, and not limitation. Where methods described above indicate certain events occurring in certain order, the ordering of certain events may be modified. Additionally, some of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. An apparatus, comprising:
  a housing assembly including a first housing portion and a second housing portion, the first housing portion and the second housing portion collectively defining a first interior cavity;
  an internal cartridge defining a reservoir, the internal cartridge at least partially disposed within the interior cavity; and
  a plunger assembly including a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element;

wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position;

wherein the first housing portion comprises a slot in a proximal end of the first housing portion and a retaining tab extending into the slot and the first plunger portion includes a latch, the latch being disposed within the slot and engaged with the retaining tab when the first housing portion is in the first position, the latch being disengaged from the retaining tab and translatable through the slot when the first housing portion is in the second position.

2. The apparatus of claim 1, wherein, when the first housing portion is in the first position, the second plunger portion is disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space.

3. The apparatus of claim 1, wherein the second plunger portion comprises a guide extending from the sidewall, the guide disposed between the distal end wall of the second plunger portion and the sealing element, the guide contacting an inner surface of the internal cartridge.

4. The apparatus of claim 1, wherein the first plunger portion includes at least one tab biased to expand axially from a first compressed configuration to a second projecting configuration relative to a central longitudinal axis of the first plunger portion when the first housing portion is in the second position and the first plunger portion has been longitudinally translated proximally relative to the first housing portion, the at least one tab configured to extend through a recess of the second plunger portion in the second projecting configuration.

5. The apparatus of claim 1, further comprising a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position.

6. The apparatus of claim 5, wherein the needle sheath includes a projecting portion, the projecting portion engaged with a retaining surface of the second housing portion when the first housing portion is in the first position, the projecting portion disengaged from the retaining surface of the second housing portion when the first housing portion is in the second position.

7. The apparatus of claim 5, further comprising a spring having a first end and a second end, the first end of the spring coupled to the internal cartridge and a second end of the internal cartridge coupled to the needle sheath such that the needle sheath is biased toward an expanded position relative to the internal cartridge.

8. The apparatus of claim 5, further comprising a needle cover, the needle sheath including a proximal end and a distal end, the needle including a proximal end and a distal end, the proximal end of the needle being disposed within the reservoir, the distal end of the needle and the distal end of the needle sheath coupled to the needle cover.

9. The apparatus of claim 8, wherein the needle defines a hole proximate the distal end of the needle, the needle cover being coupled to the needle via a wire threaded through the hole.

10. The apparatus of claim 8, further comprising a catch feature disposed within the internal cartridge, the needle including an engagement portion, the engagement portion configured to engage with the catch feature upon distal translation of the needle relative to the internal cartridge.

11. The apparatus of claim 8, wherein a distance from a distalmost portion of the needle cover to a proximalmost portion of the plunger is less than about three inches when the first housing portion is in the first position, the first plunger portion is partially disposed within the second cavity, and the needle cover is coupled to the distal end of the needle sheath.

12. The apparatus of claim 1, wherein the second plunger portion includes a proximal end, the sealing element being disposed proximate the proximal end of the second plunger portion.

13. A method, comprising:
rotating a first housing portion relative to a second housing portion such that a latch of a plunger is disengaged from a retaining tab of the second housing portion, an internal cartridge defining a reservoir at least partially disposed within a first interior cavity collectively defined by the first housing portion and the second housing portion, the plunger including a first plunger portion and a second plunger portion, the second plunger portion defining a second interior cavity, the first plunger portion movably disposed within the second interior cavity, the second plunger portion slidably disposed within the reservoir of the internal cartridge;
proximally translating the first plunger portion relative to the second plunger portion and relative to the first housing portion such that at least one tab of the first plunger portion transitions from a first, compressed configuration to a second, projecting configuration; and
distally translating the first plunger portion such that the at least one tab distally translates the second plunger portion within the internal cartridge.

14. The method of claim 13, wherein the rotating of the first housing portion relative to the second housing portion causes a needle sheath to rotate from an engaged position to a disengaged position relative to the second housing portion and to distally translate relative to the second housing portion such that a needle cover coupled to a distal end of the needle sheath and coupled to a distal end of a needle disposed within the needle sheath distally translates the needle relative to the internal cartridge.

15. The method of claim 14, further comprising:
removing the needle cap such that the needle is further distally translated relative to the internal cartridge.

16. An apparatus, comprising:
a housing assembly including a first housing portion and a second housing portion, the first housing portion and the second housing portion collectively defining a first interior cavity;
an internal cartridge defining a reservoir, the internal cartridge at least partially disposed within the interior cavity; and
a plunger assembly including a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element;

wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position;

wherein the first plunger portion includes at least one tab biased to expand axially from a first compressed configuration to a second projecting configuration relative to a central longitudinal axis of the first plunger portion when the first housing portion is in the second position and the first plunger portion has been longitudinally translated proximally relative to the first housing portion, the at least one tab configured to extend through a recess of the second plunger portion in the second projecting configuration.

17. The apparatus of claim 16, wherein, when the first housing portion is in the first position, the second plunger portion is disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space.

18. The apparatus of claim 16, wherein the second plunger portion comprises a guide extending from the sidewall, the guide disposed between the distal end wall of the second plunger portion and the sealing element, the guide contacting an inner surface of the internal cartridge.

19. The apparatus of claim 16, further comprising a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position.

20. The apparatus of claim 19, wherein the needle sheath includes a projecting portion, the projecting portion engaged with a retaining surface of the second housing portion when the first housing portion is in the first position, the projecting portion disengaged from the retaining surface of the second housing portion when the first housing portion is in the second position.

21. The apparatus of claim 19, further comprising a spring having a first end and a second end, the first end of the spring coupled to the internal cartridge and a second end of the internal cartridge coupled to the needle sheath such that the needle sheath is biased toward an expanded position relative to the internal cartridge.

22. The apparatus of claim 19, further comprising a needle cover, the needle sheath including a proximal end and a distal end, the needle including a proximal end and a distal end, the proximal end of the needle being disposed within the reservoir, the distal end of the needle and the distal end of the needle sheath coupled to the needle cover.

23. The apparatus of claim 22, wherein the needle defines a hole proximate the distal end of the needle, the needle cover being coupled to the needle via a wire threaded through the hole.

24. The apparatus of claim 22, further comprising a catch feature disposed within the internal cartridge, the needle including an engagement portion, the engagement portion configured to engage with the catch feature upon distal translation of the needle relative to the internal cartridge.

25. The apparatus of claim 22, wherein a distance from a distalmost portion of the needle cover to a proximalmost portion of the plunger is less than about three inches when the first housing portion is in the first position, the first plunger portion is partially disposed within the second cavity, and the needle cover is coupled to the distal end of the needle sheath.

26. The apparatus of claim 16, wherein the second plunger portion includes a proximal end, the sealing element being disposed proximate the proximal end of the second plunger portion.

27. An apparatus, comprising:
a housing assembly including a first housing portion and a second housing portion, the first housing portion and the second housing portion collectively defining a first interior cavity;
an internal cartridge defining a reservoir, the internal cartridge at least partially disposed within the interior cavity;
a plunger assembly including a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element; and
a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position;
wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position; and
wherein the needle sheath includes a projecting portion, the projecting portion engaged with a retaining surface of the second housing portion when the first housing portion is in the first position, the projecting portion disengaged from the retaining surface of the second housing portion when the first housing portion is in the second position.

28. The apparatus of claim 27, wherein, when the first housing portion is in the first position, the second plunger portion is disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space.

29. The apparatus of claim 27, wherein the second plunger portion comprises a guide extending from the sidewall, the guide disposed between the distal end wall of the second plunger portion and the sealing element, the guide contacting an inner surface of the internal cartridge.

30. The apparatus of claim 27, further comprising a spring having a first end and a second end, the first end of the spring coupled to the internal cartridge and a second end of the internal cartridge coupled to the needle sheath such that the needle sheath is biased toward an expanded position relative to the internal cartridge.

31. The apparatus of claim 27, further comprising a needle cover, the needle sheath including a proximal end and a distal end, the needle including a proximal end and a distal end, the proximal end of the needle being disposed within the reservoir, the distal end of the needle and the distal end of the needle sheath coupled to the needle cover.

32. The apparatus of claim 31, wherein the needle defines a hole proximate the distal end of the needle, the needle cover being coupled to the needle via a wire threaded through the hole.

33. The apparatus of claim 31, further comprising a catch feature disposed within the internal cartridge, the needle including an engagement portion, the engagement portion configured to engage with the catch feature upon distal translation of the needle relative to the internal cartridge.

34. The apparatus of claim 31, wherein a distance from a distalmost portion of the needle cover to a proximalmost portion of the plunger is less than about three inches when the first housing portion is in the first position, the first plunger portion is partially disposed within the second cavity, and the needle cover is coupled to the distal end of the needle sheath.

35. The apparatus of claim 27, wherein the second plunger portion includes a proximal end, the sealing element being disposed proximate the proximal end of the second plunger portion.

36. An apparatus, comprising:
a housing assembly including a first housing portion and a second housing portion, the first housing portion and the second housing portion collectively defining a first interior cavity;
an internal cartridge defining a reservoir, the internal cartridge at least partially disposed within the interior cavity;
a plunger assembly including a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element;
a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position; and
a spring having a first end and a second end, the first end of the spring coupled to the internal cartridge and a second end of the internal cartridge coupled to the needle sheath such that the needle sheath is biased toward an expanded position relative to the internal cartridge;
wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position.

37. The apparatus of claim 36, wherein, when the first housing portion is in the first position, the second plunger portion is disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space.

38. The apparatus of claim 36, wherein the second plunger portion comprises a guide extending from the sidewall, the guide disposed between the distal end wall of the second plunger portion and the sealing element, the guide contacting an inner surface of the internal cartridge.

39. The apparatus of claim 36, further comprising a needle cover, the needle sheath including a proximal end and a distal end, the needle including a proximal end and a distal end, the proximal end of the needle being disposed within the reservoir, the distal end of the needle and the distal end of the needle sheath coupled to the needle cover.

40. The apparatus of claim 39, wherein the needle defines a hole proximate the distal end of the needle, the needle cover being coupled to the needle via a wire threaded through the hole.

41. The apparatus of claim 39, further comprising a catch feature disposed within the internal cartridge, the needle including an engagement portion, the engagement portion configured to engage with the catch feature upon distal translation of the needle relative to the internal cartridge.

42. The apparatus of claim 39, wherein a distance from a distalmost portion of the needle cover to a proximalmost portion of the plunger is less than about three inches when the first housing portion is in the first position, the first plunger portion is partially disposed within the second cavity, and the needle cover is coupled to the distal end of the needle sheath.

43. The apparatus of claim 36, wherein the second plunger portion includes a proximal end, the sealing element being disposed proximate the proximal end of the second plunger portion.

44. An apparatus, comprising:
- a housing assembly including a first housing portion and a second housing portion, the first housing portion and the second housing portion collectively defining a first interior cavity;
- an internal cartridge defining a reservoir, the internal cartridge at least partially disposed within the interior cavity;
- a plunger assembly including a first plunger portion, a second plunger portion, and a sealing element, the second plunger portion defining a distal end wall, a sidewall, and a second interior cavity, the first plunger portion movably disposed within the second interior cavity, the second plunger portion slidably disposed within the reservoir of the internal cartridge, the sealing element coupled to the second plunger portion proximal of the distal end wall of the second plunger portion, the sealing element configured to sealingly couple the second plunger portion to the internal cartridge such that the reservoir is partially defined by the sealing element;
- a needle and a needle sheath, the needle partially disposed within the reservoir, the needle sheath partially disposed within the first interior cavity, the needle sheath prevented from being longitudinally translated relative to the second housing portion when the first housing portion is in the first position, the needle sheath longitudinally translatable relative to the second housing portion when the first housing portion is in the second position;
- a needle cover, the needle sheath including a proximal end and a distal end, the needle including a proximal end and a distal end, the proximal end of the needle being disposed within the reservoir, the distal end of the needle and the distal end of the needle sheath coupled to the needle cover; and
- wherein the first housing portion is configured to be rotated relative to the second housing portion between a first position and a second position, the first plunger portion prevented from being longitudinally translated relative to the second plunger portion when the first housing portion is in the first position, the first plunger portion longitudinally translatable relative to the second plunger portion when the first housing portion is in the second position.

45. The apparatus of claim 44, wherein, when the first housing portion is in the first position, the second plunger portion is disposed within the reservoir such that a circumferential gap is defined between the sidewall of the second plunger portion and an inner surface of the internal cartridge and such that a space is defined between the distal end wall and a distal end of the internal cartridge, the circumferential gap being in fluid communication with the space.

46. The apparatus of claim 44, wherein the second plunger portion comprises a guide extending from the sidewall, the guide disposed between the distal end wall of the second plunger portion and the sealing element, the guide contacting an inner surface of the internal cartridge.

47. The apparatus of claim 44, wherein the needle defines a hole proximate the distal end of the needle, the needle cover being coupled to the needle via a wire threaded through the hole.

48. The apparatus of claim 44, further comprising a catch feature disposed within the internal cartridge, the needle including an engagement portion, the engagement portion configured to engage with the catch feature upon distal translation of the needle relative to the internal cartridge.

49. The apparatus of claim 44, wherein a distance from a distalmost portion of the needle cover to a proximalmost portion of the plunger is less than about three inches when the first housing portion is in the first position, the first plunger portion is partially disposed within the second cavity, and the needle cover is coupled to the distal end of the needle sheath.

50. The apparatus of claim 44, wherein the second plunger portion includes a proximal end, the sealing element being disposed proximate the proximal end of the second plunger portion.

* * * * *